(12) United States Patent
Di Lauro et al.

(10) Patent No.: US 10,806,650 B2
(45) Date of Patent: Oct. 20, 2020

(54) EXTREMITY STABILIZATION APPARATUS

(71) Applicant: VeniSTAT, Inc., Carlsbad, CA (US)

(72) Inventors: Michael Craig Di Lauro, Carlsbad, CA (US); Brian Michael Brenner, Carlsbad, CA (US)

(73) Assignee: VeniSTAT, Inc., Carlsbad, CA (US)

( * ) Notice: Subject to any disclaimer, the term of this patent is extended or adjusted under 35 U.S.C. 154(b) by 0 days.

(21) Appl. No.: 16/233,732

(22) Filed: Dec. 27, 2018

(65) Prior Publication Data
US 2019/0201258 A1 Jul. 4, 2019

Related U.S. Application Data

(60) Provisional application No. 62/695,811, filed on Jul. 9, 2018, provisional application No. 62/695,804, filed
(Continued)

(51) Int. Cl.
*A61G 5/12* (2006.01)
*A61G 13/12* (2006.01)
(Continued)

(52) U.S. Cl.
CPC .............. *A61G 5/125* (2016.11); *A61G 7/075* (2013.01); *A61G 13/101* (2013.01);
(Continued)

(58) Field of Classification Search
CPC .......... A61G 5/12; A61G 5/125; A61G 7/065; A61G 7/075; A61G 13/12; A61G 13/1205; A61G 13/1235; A61G 13/124; A61G 13/128–1295; A61G 5/127; A61G 5/128; A61G 7/0755; A61G 13/1206; A61G 1/04–048; A61M 5/52; A47C 1/022;
(Continued)

(56) References Cited

U.S. PATENT DOCUMENTS 2,119,325 A * 5/1938 Goodhart ................ A61M 5/52
602/16
2,551,617 A 5/1951 Maybert
(Continued)

OTHER PUBLICATIONS

International Search Report and Written Opinion dated Mar. 8, 2019 in PCT No. PCT/US2018/067833.

*Primary Examiner* — Keri J Nelson
*Assistant Examiner* — Michelle J Lee
(74) *Attorney, Agent, or Firm* — Knobbe, Martens, Olson & Bear, LLP

(57) ABSTRACT

An extremity stabilization apparatus and methods for supporting and immobilizing an extremity during venous access. One example of an apparatus includes a cuff having a top surface structured for receiving a limb of a patient, the cuff having a front end and a back end. The surface of the cuff may be c-shaped such that the cuff partially surrounds the extremity received in the cuff. The apparatus further includes a handle having a grip for receiving the hand of a patient, the grip arranged offset from the front end of the cuff, and an assembly coupled to the cuff, the assembly movable between at least a first position and a second position to change the position of the top surface of the cuff, each of the first position and second positions corresponding to a different angle of the top surface of the cuff.

11 Claims, 50 Drawing Sheets

Related U.S. Application Data on Jul. 9, 2018, provisional application No. 62/612,200, filed on Dec. 29, 2017, provisional application No. 62/612,212, filed on Dec. 29, 2017.

(51) Int. Cl.
  *A61G 13/10* (2006.01)
  *A61M 5/52* (2006.01)
  *A61G 7/075* (2006.01)
  *A61G 1/04* (2006.01)

(52) U.S. Cl.
  CPC ....... *A61G 13/124* (2013.01); *A61G 13/1235* (2013.01); *A61M 5/52* (2013.01); *A61G 1/04* (2013.01)

(58) Field of Classification Search
  CPC ....... A47C 1/03–08; A61B 90/60; A61F 5/01; A61F 5/0102; A61F 5/013; A61F 5/0106; A61F 5/0111–0118; A61F 5/0123–0127; A61F 5/04–048; A61F 5/37; A61F 5/3761; A61F 2005/0132–0179; A47B 21/0371; A47B 2021/0314; A47B 2021/0392
  See application file for complete search history.

(56) References Cited

U.S. PATENT DOCUMENTS

| | | | |
|---|---|---|---|
| 2,693,794 A * | 11/1954 | Neville | A61M 5/52 600/499 |
| 3,528,413 A | 9/1970 | Aydt | |
| 3,556,092 A | 1/1971 | Eisenberg | |
| 3,614,085 A | 10/1971 | Cunningham | |
| 3,812,851 A | 5/1974 | Rodriguez | |
| 4,277,102 A | 7/1981 | Aaras et al. | |
| 4,369,774 A | 1/1983 | Robbins | |
| 4,913,393 A | 4/1990 | Wood | |
| 5,135,190 A * | 8/1992 | Wilson | A47B 21/0371 248/118.1 |
| 5,281,001 A | 1/1994 | Bergsten et al. | |
| 5,407,249 A | 4/1995 | Bonutti | |
| 5,713,591 A | 2/1998 | Zarkhin | |
| 5,848,979 A * | 12/1998 | Bonutti | A61F 5/013 601/5 |
| 5,864,902 A | 2/1999 | Rogers | |
| 6,663,055 B2 | 12/2003 | Boucher et al. | |
| 7,055,910 B2 | 6/2006 | Wright | |
| 2002/0121042 A1 | 9/2002 | Macaluso | |
| 2005/0052066 A1 | 3/2005 | Wright | |

\* cited by examiner

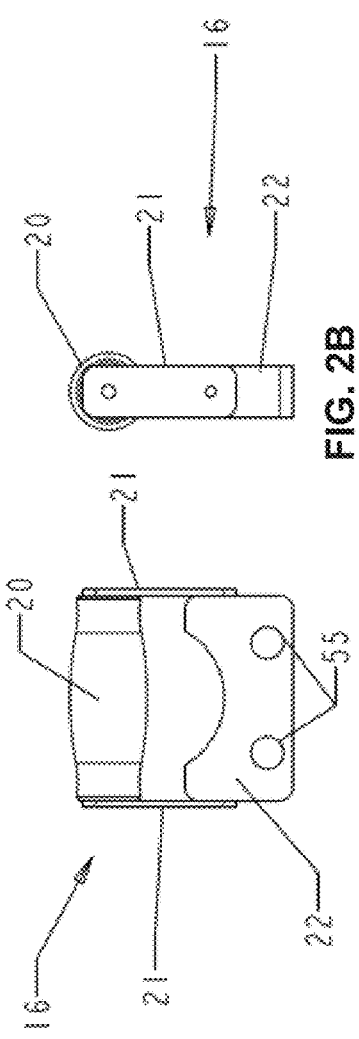
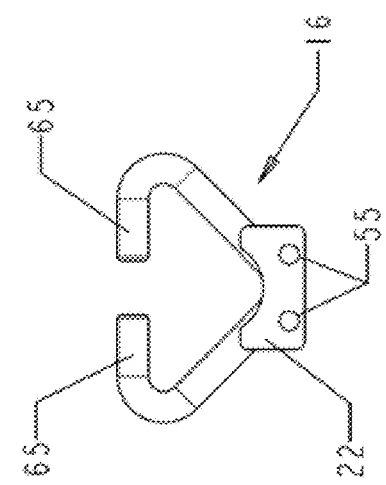
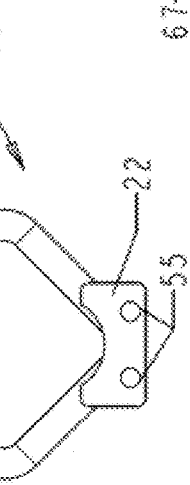
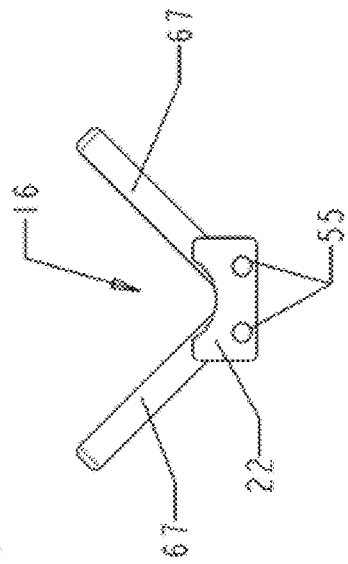

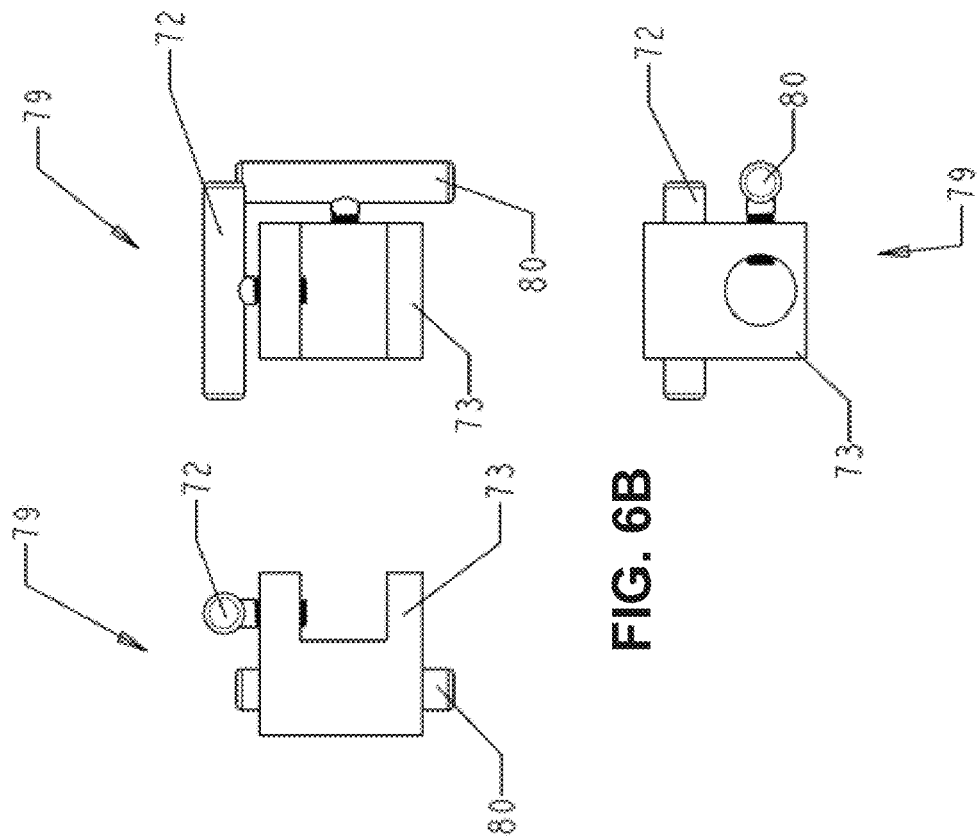
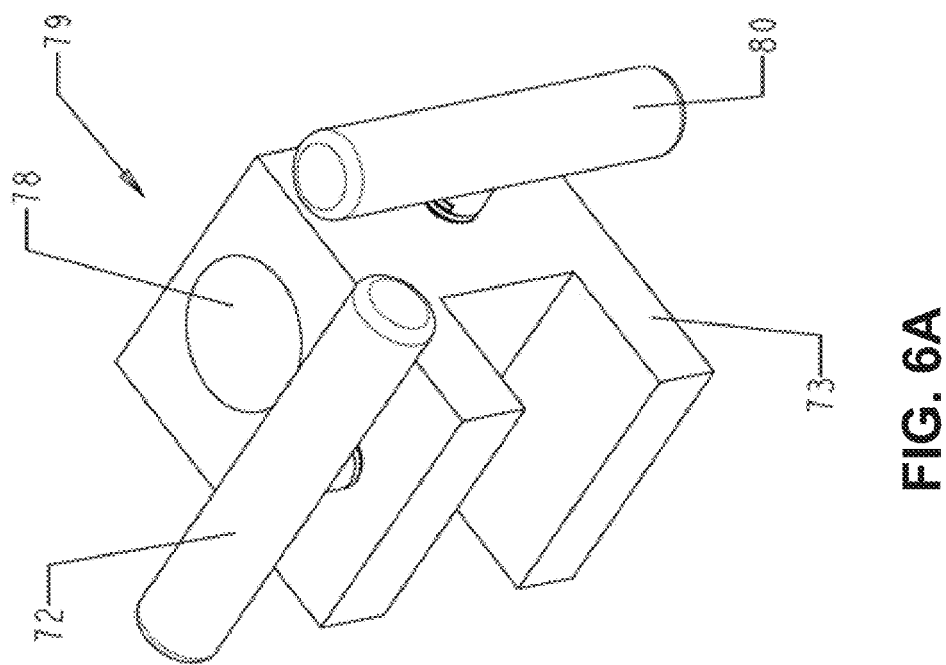
FIG. 6B
FIG. 6A

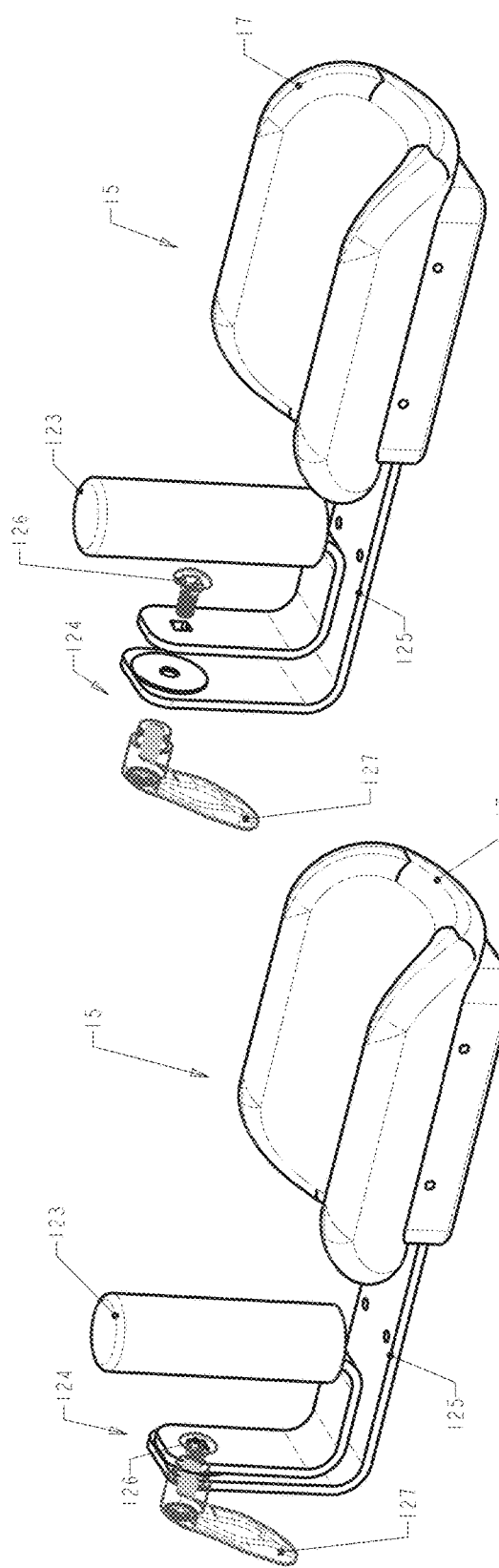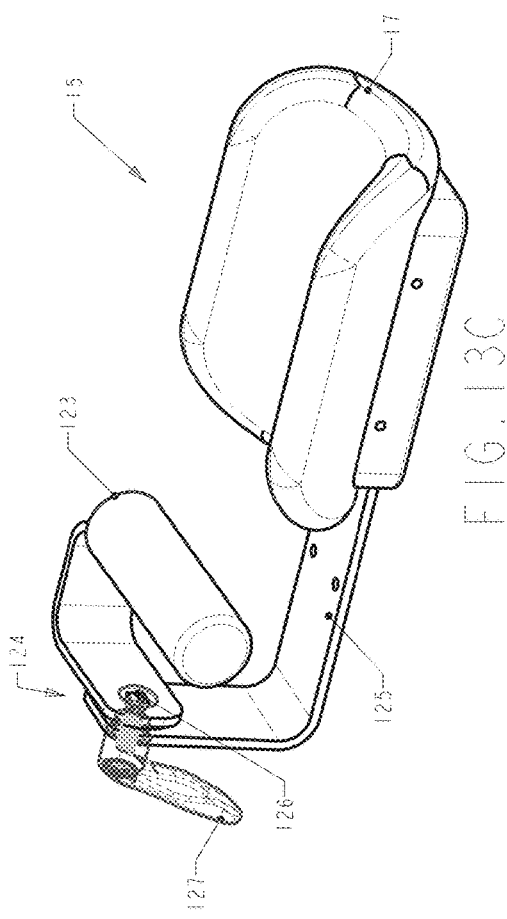

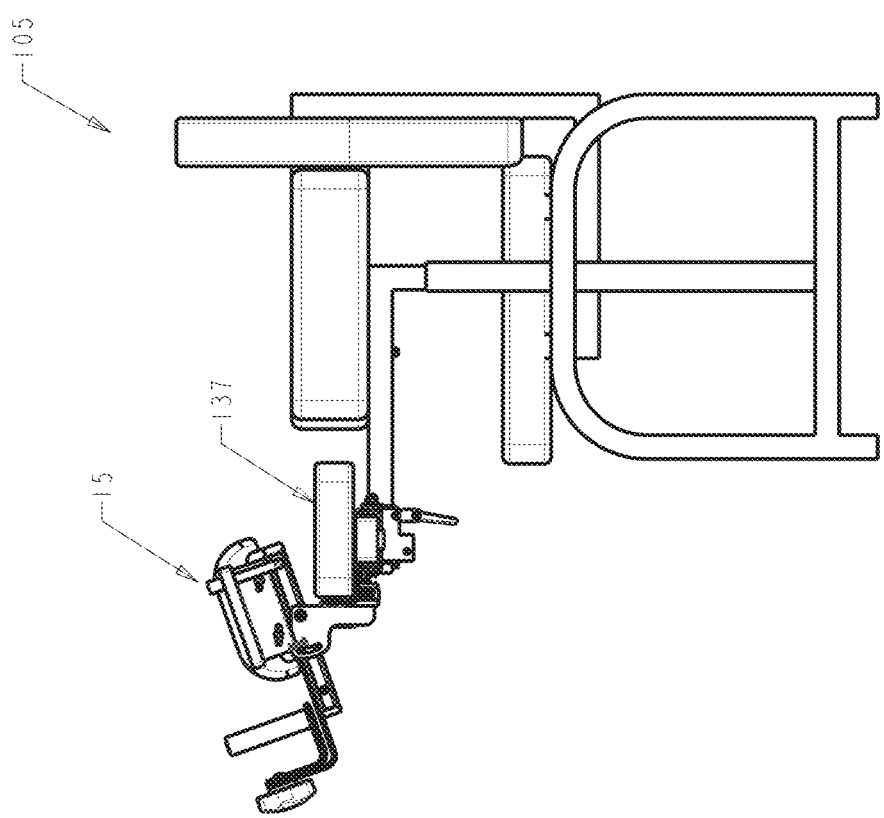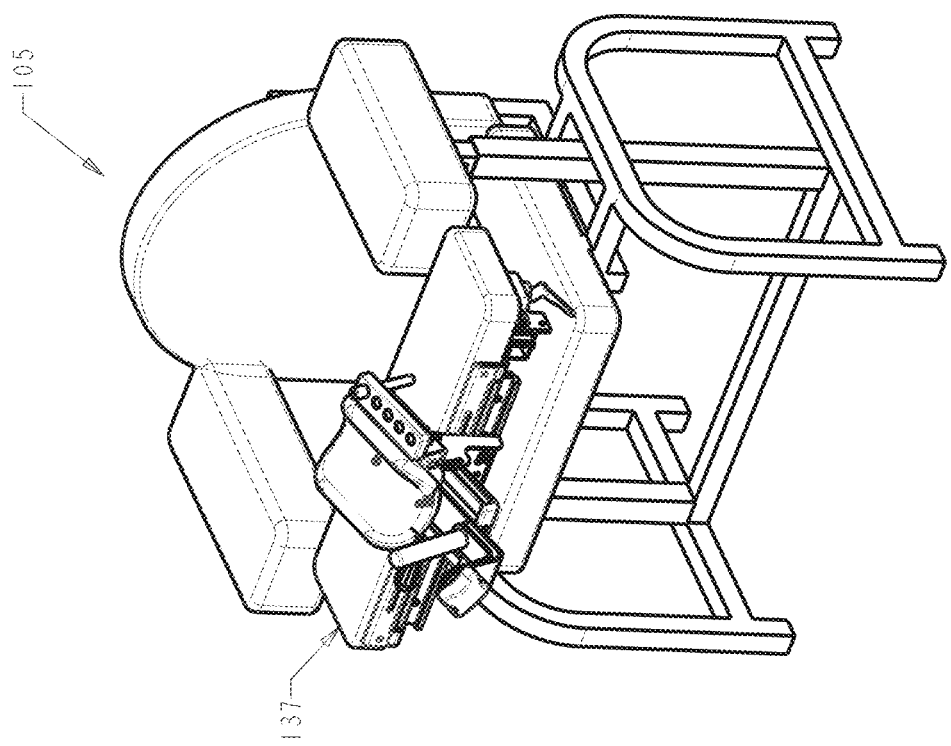
FIG. 15

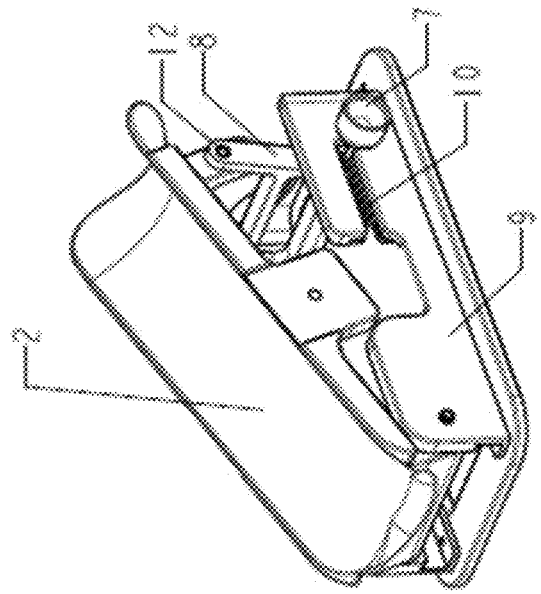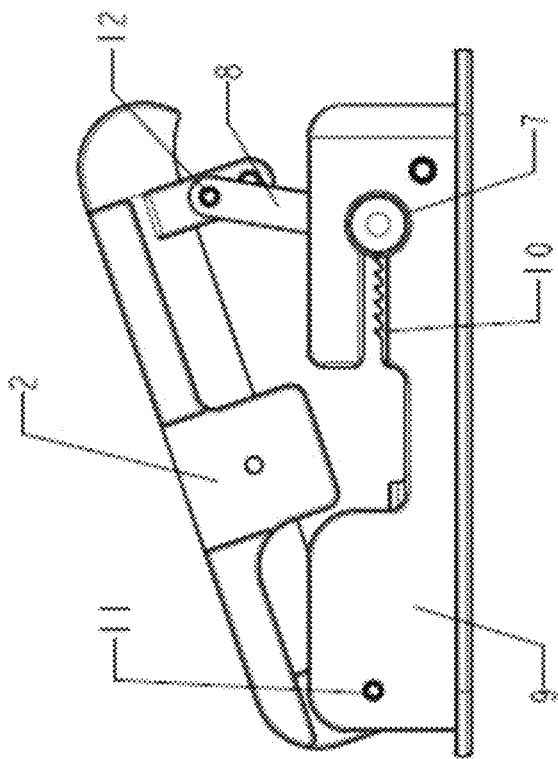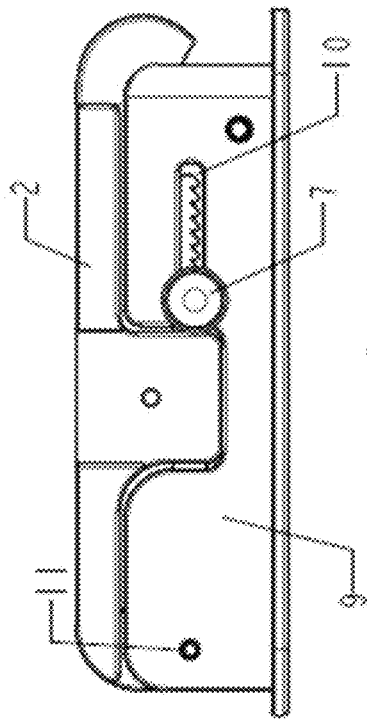
FIG. 26A
FIG. 26B
FIG. 26C

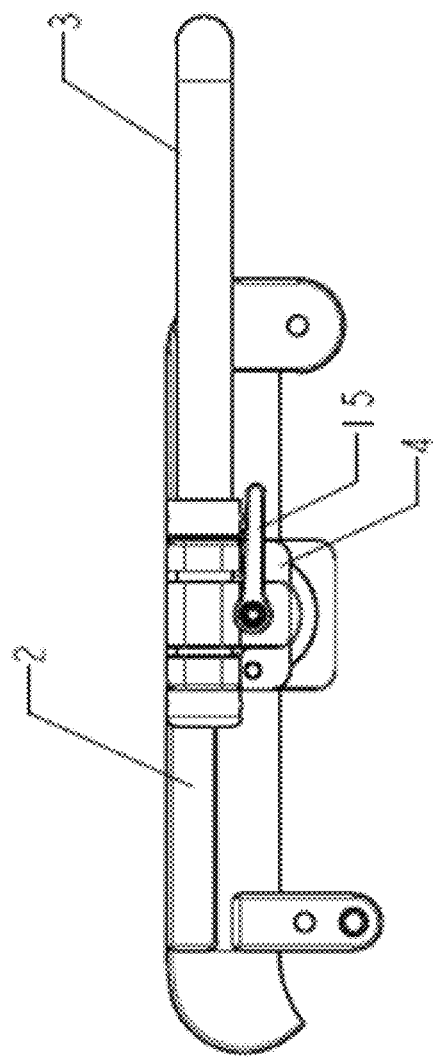
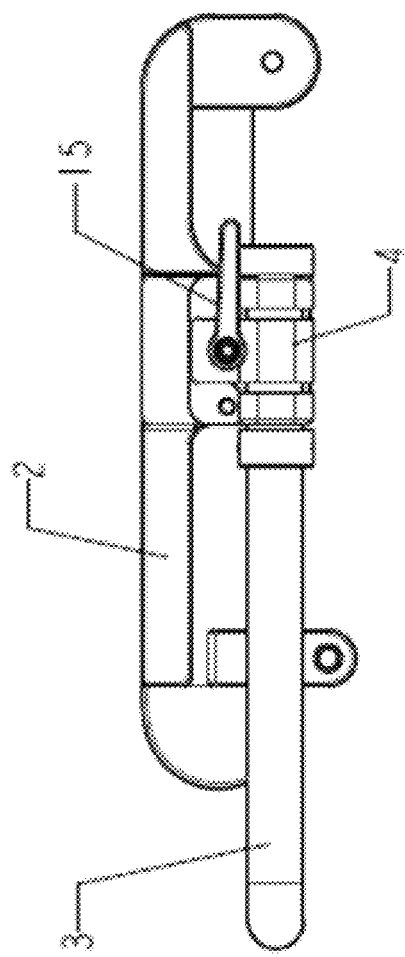
FIG. 28A
FIG. 28B

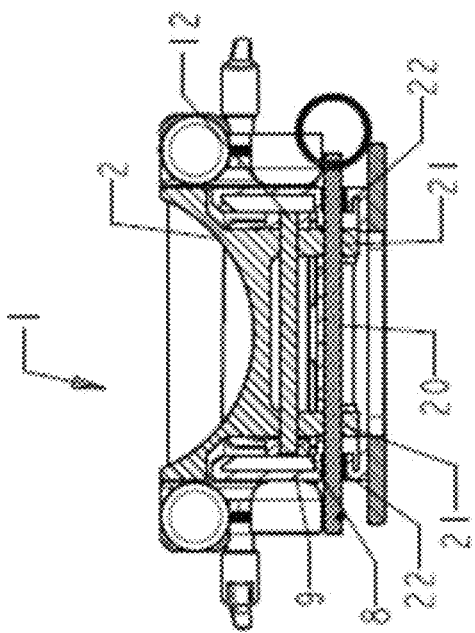
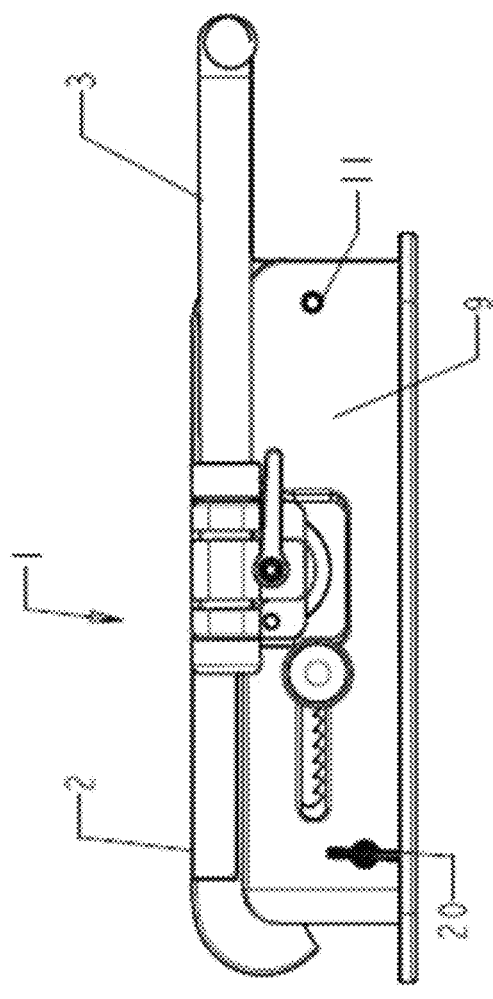
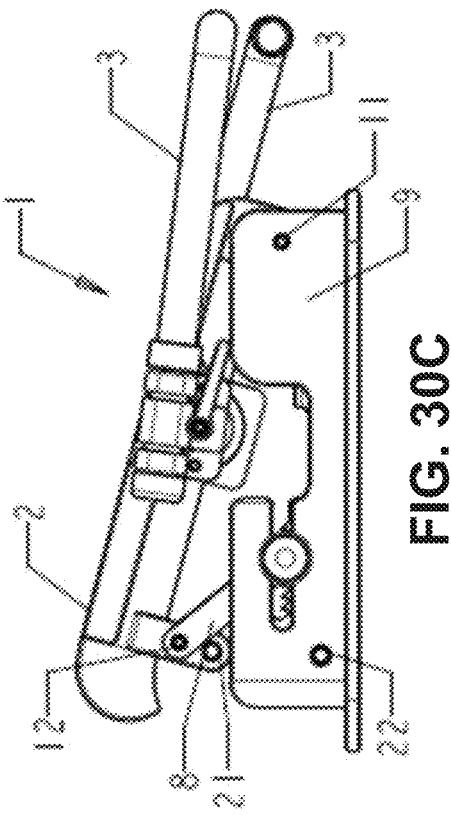
FIG. 30B
FIG. 30D
FIG. 30A
FIG. 30C

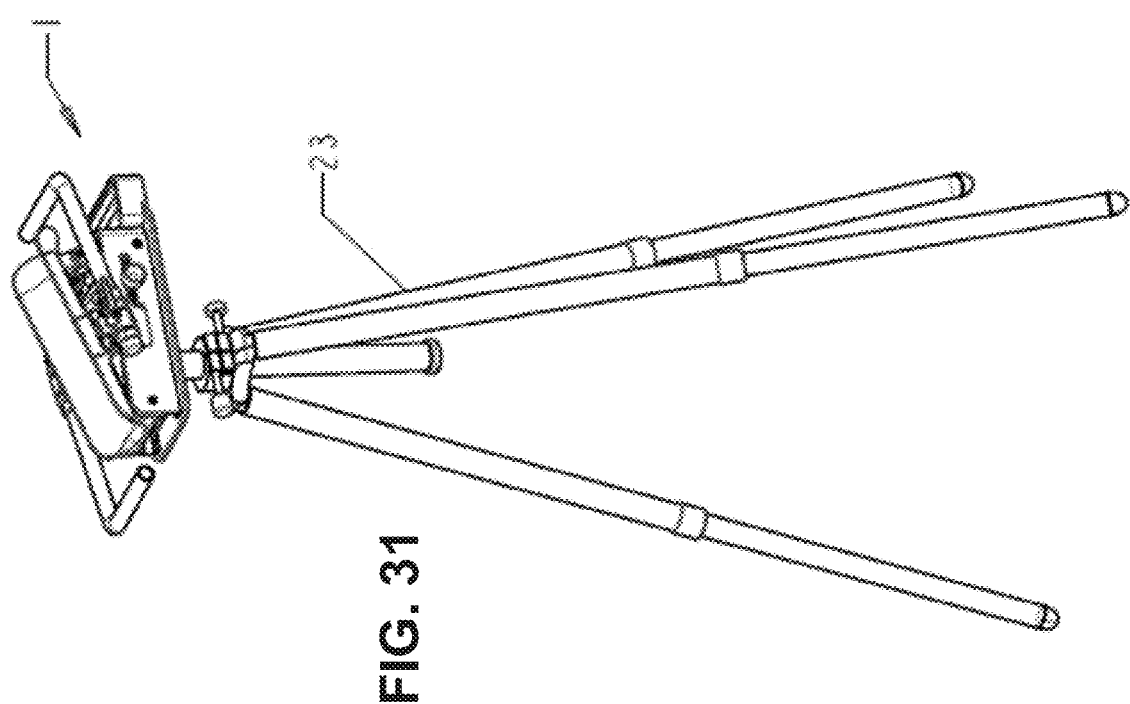

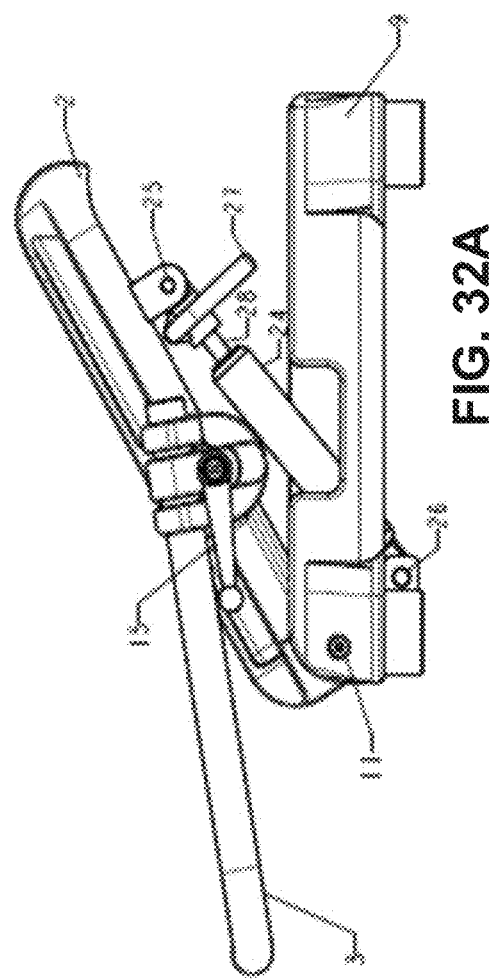
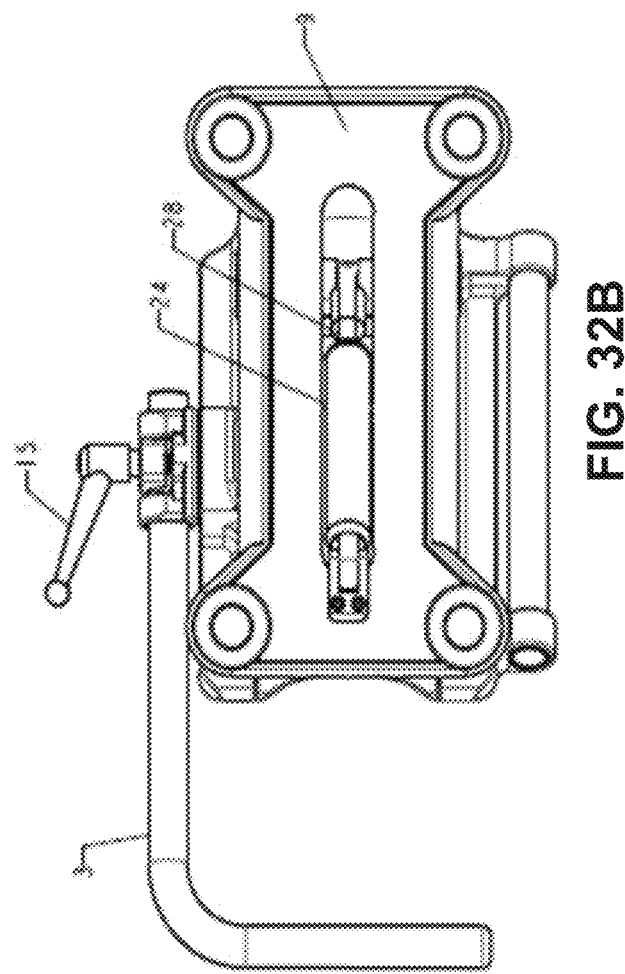
FIG. 32A
FIG. 32B

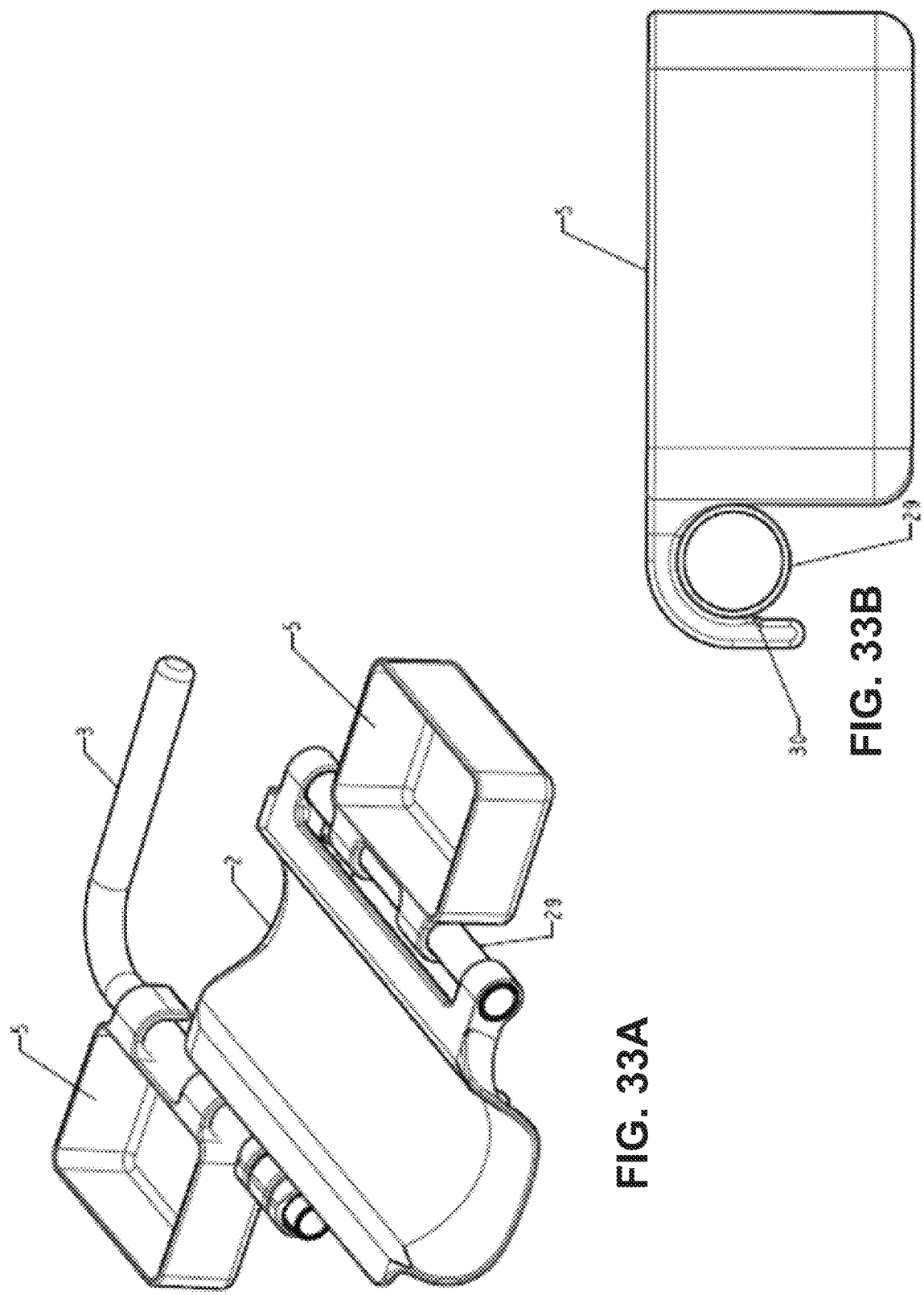

EXTREMITY STABILIZATION APPARATUS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

Various types of ambulatory and medical emergency cots, gurneys, medical beds, medical chairs and wheeled stretchers and the like are utilized during venipuncture or the process of obtaining intravenous access for the purpose of intravenous therapy or for blood sampling of venous blood from a body extremity. Most commonly the body extremity is an arm either in the hand or at the antecubital fossa. In order to avoid injury and ensure proper administration, it is important that the patient's body extremity or limb to remain immobile, controlled, and properly positioned during the procedure. As described herein, the term "crossbar" refers to a support surface configured to support an arm or leg, and is typically generally parallel to the plane defined by the seat of a medical chair. With regards to venous access, current phlebotomy or blood draw chairs are designed to allow the patient to sit upright with an optional foldable crossbar or surface that sits across and in front of the patient and is utilized to support the patients limb during the venipuncture procedure. Other times, the healthcare provider will utilize the left or right arm rests to support the patient's limb during the venipuncture procedure. Although the foldable crossbar and arm rests allow the patient to rest their limb, patients can freely move their arms.

The use of a medical chair applies when a patient visits a central blood collection facility. Other times, when the patients' blood sample is collected outside of a central blood draw facility (e.g., patient residences, nursing homes, etc.,) the health care provider does not have access to a dedicated medical chair to provide a suitable surface to work on in stabilizing the patient's limb during venous blood collection. In the absence of a dedicated medical chair, the healthcare provider is forced to rely on surrounding objects at their immediate disposal to assist in stabilizing the patient's limb (e.g., a desk, a bed, a chair, or a table). Although these objects offer some stability, none prevent patient movement and they are inadequate to properly stabilize a patient's limb during venous access. More specifically, unintentional or abrupt movement of the patient's extremity during venous blood draw creates a hazardous environment for both the patient and the healthcare provider, which can lead to accidental needle sticks or repeated attempts at accessing the patient's vein.

Accordingly, it would be advantageous to have a device designed to address the shortcomings associated with lack of proper limb support described above.

SUMMARY OF THE INVENTION

The systems, methods, and devices of the invention each have several aspects (features), no single aspect of which is solely responsible for its desirable attributes. Without limiting the scope of this invention as expressed by the claims which follow, some of the aspects are described below.

Described herein are adjustable devices that can be rest on a surface, or are fixedly or removably attached to a medical emergency cot, gurney, wheeled stretcher, medical bed, medical chair or the like, that functions to support and immobilize an extremity of a human body (for example, an arm or leg) during venous access. Any of the extremity stabilization devices referred to herein may also be referred to as an apparatus, and these terms are used interchangeably herein unless the context of the disclosure indicates otherwise. As referred to herein, the phrase "patient support surface" shall apply to, but not be limited to, a medical emergency cot, gurney, wheeled stretcher, medical bed, medical chair or the like. Embodiments of the device provide rigid support for a limb and are easily adjustable to support the limb at various angles, for example, relative to a surface a patient is sitting on, or a surface the device sits on or is attached to and support the limb in different rotational positions while providing support for the limb at the various angles. One embodiment of a device described herein may be referred to as an Extremity Stabilization Apparatus and it is designed to stabilize the patient's limb through two points of contact. One (or a first) point of contact supports the position of the patient's arm or extremity, while the other (or a second) point of contact supports the position of the patient's hand. Restricting the position of the patient's arm relative to their hand thereby restricts the patient from bending their elbow or otherwise pulling their arm away during venipuncture.

In some embodiments, the arm support is in the form of an open cuff and the hand support is in the form of a handle. The open cuff includes a support surface that is configured to go be disposed around at least a portion of an arm when the arm is placed in the cuff. In some embodiments, the cuff is an open cuff that includes one or more restraining components that, in cooperation with the cuff, are configured to surround a portion of, or all of, an arm to better hold and restrain the arm from movement. In some embodiments, the cuff is a closed cuff that surrounds the arm. The handle may be rotatably coupled to the cuff and can be locked in any, or a plurality of, desired rotational positions. The rotatably coupled handle and cuff allows the healthcare provider to rotate the patients hand relative to their elbow to allow for antecubital or hand access during venipuncture. In such embodiments, the cuff is removably attached to the Extremity Stabilization Apparatus to allow the healthcare provider to select the appropriate size cuff diameter to substantially match the diameter or curvature of the patient's forearm. This is especially important for pediatrics since the diameter of their forearm is smaller than that of an adult. In certain embodiments, the Extremity Stabilization Apparatus is rotatably coupled to a modular clamp assembly wherein the modular clamp assembly is removably attached to a medical chair, medical bed, table, wheeled stretcher, or the like, with the rotational position adjusted with a single mechanism. The Extremity Stabilization Apparatus may be slideably and rotatably coupled to a rotating post and are both locked into position with one single mechanism allowing the healthcare provider to adjust the extension and tilt of the apparatus at once. Adjusting the extension and tilt at once allows the healthcare provider to adjust the Extremity Stabilization Apparatus to accommodate patients of varying heights and arm reach. Furthermore in some such embodiments, the healthcare provider can rotate the Extremity Stabilization Apparatus to access patients that are bound by a wheelchair and cannot move themselves into the medical chair.

In another embodiment, in the plane substantially parallel to the plane defined by the back rest of the medical chair, an Extremity Stabilization Apparatus is slideably coupled to the medical chair and locked into position with one single mechanism allowing the healthcare provider to choose between the patient's right or left limb for venipuncture. In this embodiment, in the plane substantially parallel to the plane defined by the seat of the medical chair, the Extremity Stabilization Apparatus may be rotatably coupled to the medical chair and can be locked into position with one single mechanism allowing the healthcare provider to open and close the crossbar surface of the medical chair without having to lift it against gravity. In this embodiment the healthcare provider is less likely to develop musculoskeletal injury due to repetitive lifting since they no longer have to lift and lower the crossbar surface for each patient. Furthermore in this embodiment, the healthcare provider can rotate the Extremity Stabilization Apparatus away from the plane parallel to the back rest of the medical chair to access patients that are bound by a wheelchair and cannot move themselves into the medical chair.

In another embodiment, the Extremity Stabilization Apparatus described above is fixedly or removably attached to the bed frame of a medical bed or medical stretcher allowing the healthcare professional the ability to control the patient's limb during venipuncture inside a hospital room or in the back of an ambulance.

In another embodiment the Extremity Stabilization Apparatus described above is fixedly or removably attached to the siderail of a medical bed or medical stretcher allowing the healthcare professional the ability to control the patient's limb during venipuncture inside a hospital room or in the back of an ambulance.

In another embodiment the Extremity Stabilization Apparatus described above is incorporated into a mobile cart that allows the health care professional the ability to control a person's limb by rolling the mobile cart near the patient's limb when a fixedly or removably Extremity Stabilization Apparatus is not available on a patient's medical bed, chair, wheelchair or medical stretcher.

In another embodiment, the apparatus is mobile with a rollable base is fixedly attached to an extension pole assembly that raises and lowers the relative position of the Extremity Stabilization Apparatus depending on the position of the patient. In the preferred embodiment the Extremity Stabilization Apparatus is slideably and rotatably coupled to one end of the extension pole assembly allowing for access to a patient's limb at varying angles inside the boundary defined by a medical bed or wheeled stretcher. In other embodiments the apparatus is fixedly attached to a rigid surface defined by a medical emergency cot, gurney, wheeled stretcher, medical bed, medical chair or the like. Such an apparatus is of simple construction and yet permits a high degree of adjustability.

In certain embodiments, the extension pole assembly is comprised of a base and an extension pole that is slideably coupled to the extension pole base. The distance that the extension pole can travel in and out of the base is controlled by an adjustable handle that compresses against the surface of the extension pole. In the preferred embodiment, the extension pole has a channel to receive the adjustable handle that will restrict rotational movement between the extension pole base and the extension pole. In other embodiments the extension pole has a series of holes to allow for the incremental adjustment of the extension pole through a spring loaded plunger handle. In other embodiments the extension pole is slideably and rotatably coupled to the base and is secured in a desired position by threading a threaded extension collar onto the base extension pole which compresses an internal component onto the extension pole.

In certain embodiments, the rollable assembly can be quickly secured to any rigid surface by positioning a slideably coupled clamp on the top, bottom or both top and bottom of any available rigid surface. Having the means to secure the apparatus to a rigid surface is beneficial to maintaining stability of a patient's limb during Venipuncture. In certain embodiments the rollable assembly can be secured by removing any contact between the wheels of the rollable assembly and the floor. Such a configuration can be achieved by actuating a lowering platform to the floor. In this embodiment, the lowering platform is slideably coupled to the base assembly and has a geared profile to mate with a hand crank pinion to adjust the position.

In certain embodiments, the control arm that connects the cuff and hand assemblies is spherically coupled to the extension pole and secured with a threaded friction handle to allow for a high degree of adjustability. In certain embodiments, the control arm that connects the cuff and hand assemblies is rotatably coupled to the extension pole and secured with a threaded friction handle to allow for adjustability. In a certain embodiments, the control arm is slideably and rotatably coupled to the extension pole and secured with a threaded c-clamp style clamp. In certain preferred embodiments opposite end of the control arm is rotatably coupled to the Extremity Stabilization Apparatus to allow for 360 degree rotation of the Extremity Stabilization Apparatus. This embodiment is beneficial to allow the user to perform Venipuncture on either side of the patient thereby accessing the left or right side of the patient's extremity.

In certain embodiments, the Extremity Stabilization Apparatus is spherically coupled to the control arm and secured with a threaded friction handle to allow for a high degree of adjustability of the Extremity Stabilization Apparatus. In certain embodiments, the handle assembly is slideably and rotatably coupled to a series of Extremity Stabilization Apparatus poles which are fixedly attached to the Extremity Stabilization Apparatus. Having the cuff and the handle assembly free to adjust to any distance relative to each other is beneficial to accommodating patients with limbs of varying length.

The Extremity Stabilization Apparatus poles can be but are not limited to two separate poles. Other embodiments can have one or three Extremity Stabilization Apparatus poles. In other embodiments the Extremity Stabilization Apparatus poles are replaced by a key cut assembly that allows for the handle assembly to be slideably and rotatably coupled to a rail that is fixed attached to the Extremity Stabilization Apparatus. In certain other embodiments the handle assembly is fixedly attached to the Extremity Stabilization Apparatus poles. In this embodiment, the Extremity Stabilization Apparatus poles are slideably coupled to the Extremity Stabilization Apparatus to allow for relative translation between the handle assembly and the Extremity Stabilization Apparatus.

In certain embodiments the handle has a central aperture to allow for the patient to insert their hand into the aperture to grip the top or either side of the inside of the cuff handle during Venipuncture. Having the patient's hand reach in and grip the inside of the handle is beneficial to establish proper limb support and stabilization during antecubital access of the patient's vein during Venipuncture. In other embodiments, the patient can grip the top surface of the handle grip; a position beneficial to hand access of the vein during Venipuncture. In certain embodiments the handle can form a closed or open loop. In certain embodiments the lateral sides of the handle can be angled to allow for the patient to comfortably grip the handle assembly at any desired angle.

In certain embodiments the base of the apparatus can be fixedly attached to a medical emergency cot, gurney, wheeled stretcher, medical bed, medical chair or the like with a modular clamp assembly. In certain embodiments the modular clamp assembly is a c-clamp style clamp to allow it to easily attach to a railed component of a medical emergency cot, gurney, wheeled stretcher, medical bed, medical chair or the like. In this embodiment a handle assembly is slideably and rotatably coupled to Extremity Stabilization Apparatus poles. Also in this embodiment, the Extremity Stabilization Apparatus poles are fixedly attached to a Extremity Stabilization Apparatus that is spherically coupled to a cuff post. Also in this embodiment, the cuff post is slideably and rotatably coupled to the modular clamp assembly which is clamped to a desired location of a railed component of a medical emergency cot, gurney, wheeled stretcher, medical bed, medical chair or the like. This embodiment is beneficial to ambulance cots and medical beds when time is limited and quick assembly of the apparatus is necessary.

In certain embodiments, the modular clamp assembly is cannulated to allow for a cuff post to be inserted into the cannula. In this embodiment the cuff post can be easily attached or removed from the modular clamp assembly. In this embodiment the cuff post may include a ring or a stop that is fixedly attached to the outer surface that controls the depth at which the cuff post is inserted into the cannula. In this embodiment, the cuff post is slideably and rotatably coupled to the modular clamp assembly. In other embodiments, the cuff post can be lowered or raised in and out of the cannula of the modular clamp assembly by tightening threaded handle against the cuff post. In other embodiments, the cuff post can have a series of perforations to receive a plunger attached to the modular clamp assembly to control the rotational and translational position of the cuff post relative to the modular clamp assembly. In other embodiments, the cuff post can have a polygonal shape that can be inserted into similar polygonal shape on the modular clamp assembly.

In other embodiments, the cuff post is fixedly attached to the modular clamp assembly forming one complete modular clamp assembly consisting of a modular clamp, a cuff post that is spherically or rotatably coupled to an Extremity Stabilization Apparatus. In this embodiment the Extremity Stabilization Apparatus is fixedly attached to Extremity Stabilization Apparatus poles with a handle assembly rotatably and slideably coupled to the Extremity Stabilization Apparatus poles.

Other embodiments provide an adjustable device that functions to support and immobilize an extremity of a human body (e.g., a limb) without the use of a medical chair, during venous access. Such devices may be referred to herein as a Mobile Extremity Stabilization Apparatus. In some embodiments device may be removably attached to a stand. The device placed on any flat surface such as a desk, table or bed for the purposes of supporting and immobilizing a patient's extremity during venous access. Embodiments of the device are rigid and easily adjustable. The Mobile Extremity Stabilization Apparatus is designed to stabilize the patient's limb through two points of contact. One point of contact supports the position of the patient's forearm while the other point of contact supports the position of the patient's hand. Restricting the position of the patient's forearm relative to their hand thereby restricts the patient from bending their elbow or otherwise pulling their arm away during venipuncture.

In certain embodiments, the forearm support is in the form of an open cuff and the hand support is in the form of a handle. In this embodiment, the handle is rotatably coupled to the cuff along two separate axes with both axes locked in any desired rotational position with a single mechanism. In one axis of rotation, the rotatably coupled handle and cuff allows the healthcare provider to rotate the patients hand relative to their elbow to allow for antecubital or hand access during venipuncture. In another axis of rotation perpendicular to the axis defined by the open cuff, the handle can rotate to conform to a comfortable bend of the patient's wrist. In certain embodiments, rotation of the handle to the opposite end of the cuff is optional as hand access is achievable on any side of the cuff. In certain embodiments, one or more handles are rotatably coupled to the cuff.

In this embodiment, the cuff of the Mobile Extremity Stabilization Apparatus is rotatably coupled to a base that rests on top of a flat surface. The angle between the cuff and the base can freely increase incrementally along a one directional ratchet. To decrease the angle between the cuff and the base, the ratchet mechanism is manually released. The self-locking rotational coupling between the cuff and base, with increasing angles, allows the healthcare provider to make quick adjustments the cuff to accommodate the proper positioning of a patient's limb without a second step required to lock the angle in place.

In other certain embodiments, the angle of rotation between the cuff and the base is controlled by a pressurized cylinder. More specifically, the cylinder contains a piston element that translates along a single axis. As the internal pressure rises and falls between the cylinder and the piston element, the overall length of the combined cylinder and piston elements increase and decrease as well. A release mechanism releases the internal pressure between the cylinder and the piston elements thereby adjusting the overall length of both elements. Since opposite ends of the pressurized cylinder are connected to base and the cuff, increasing and decreasing length of the pressurized cylinder subsequently decreases and increases the angle between the cuff and the base.

In some embodiments, a removable container, also used as a blood collection tube and supplies holder, is removably attachable to the Mobile Extremity Stabilization Apparatus.

Another innovation is an apparatus for stabilizing an extremity, the apparatus including a cuff having a top surface structured for receiving a limb of a patient, the cuff having a front end and a back end, a handle comprising a grip for receiving the hand of a patient, the grip disposed offset from the front end of the cuff, and an assembly coupled to the cuff, the assembly movable between at least a first position and a second position to change the position of the top surface of the cuff, each of the first position and second positions corresponding to a different angle of the top surface of the cuff.

Embodiments of apparatus described herein may have one or more other aspects (features) in various embodiments of the system, a number of these aspects being noted here. However, various embodiments of such systems may have additional aspects or fewer aspects, and the aspects disclosed herein can be used together in a number of embodiments even if specifically not illustrated or described as being in a certain embodiment, as one of ordinary skill in the art will appreciate. In one aspect, the handle is adjustably coupled to the cuff such that the distance of the offset can be changed.

In another aspect, the handle comprises a distal portion and a proximal portion, the grip disposed on the distal portion, and the apparatus further comprises a clamp coupling the proximal portion of the handle to the cuff, the proximal portion of the handle extending through the clamp, the clamp configured to hold the handle immovable when the clamp is in a locked position and when in an unlocked position, allow the grip to rotate within the clamp around a first axis aligned along the proximal portion of the handle. In another aspect, the clamp is further configured to, when in an unlocked position, allow the proximal portion of the handle to move through the clamp to change the distance of the offset.

In another aspect, the clamp is further rotatably coupled to the cuff such that it can rotate around a second axis perpendicular to a longitudinal axis extending from the front end of the cuff to the back end of the cuff, wherein rotation of the clamp around the second axis also rotates the handle around the second axis. In another aspect, the apparatus further includes a lower support portion coupled to the assembly, and where the assembly comprises a hinge, wherein in a first position the hinge is in an extended configuration to position the back end of the cuff distal from the lower support portion of the apparatus, and in a second position the hinge is in a non-extended configuration to position the back end of the cuff proximal to the lower support portion of the apparatus. In some aspects, the lower support portion comprises at least one foot arranged to support the apparatus and to contact a surface the apparatus is placed on, and wherein the hinge includes at least two linkage members pivotally coupled together, wherein the hinge is coupled between the back end of the cuff and the at least one foot. In another aspect, the apparatus includes two, three, or four feet attached to a lower portion of the apparatus. In another aspect, the top surface of the cuff is curved such that sides of the cuff form a c-shaped surface with an opening facing away from the assembly.

In another aspect, the apparatus may further include a base positioned between the lower portion of the apparatus (e.g., the feet) and the cuff. In various configurations, the base is rotationally coupled to the front end of the cuff and coupled to the back end of the via an assembly, such that the front of the cuff can rotate at the coupling with the base, and the back end of the cuff can be moved relative to the base (e.g., elevated above the base). The base can further include a movable positioning mechanism coupled to the hinge. The base can include a locking structure configured to hold the movable positioning mechanism in a plurality of positions, each position placing the cuff at a different angle relative to the base. In some embodiments, the hinge includes at least two linkage members pivotally coupled together, the hinge coupled between the back end of the cuff and the positioning mechanism. In another aspect, the apparatus further comprises a rotating handle assembly coupled to the handle, the rotating handle assembly configured to rotate the handle in a plane substantially normal to a longitudinal axis of the cuff extending from the back end of the cuff to the front end of the cuff. In another aspect, the rotating handle assembly comprises a locking mechanism to hold the handle in a fixed position. In another aspect, the rotating handle assembly further includes a release lever to unlock the locking mechanism.

In another aspect, the apparatus includes a cuff base having a top portion coupled to the cuff, and a clamp assembly coupled to the cuff base, the clamp assembly configured to translate the cuff base and rotate the cuff base relative to the position of the clamp assembly. In another aspect, the cuff base further comprises a front portion coupled to the handle via the rotating handle assembly, and two sidewalls disposed on opposite sides of the cuff base, each of the two sidewalls including an elongated aperture aligned in a parallel with the longitudinal axis of the cuff, and the clamp assembly comprises a base clamp coupled to the cuff base by at least one member extending through the elongated apertures, the clamp assembly configured such that the cuff base is translatable to a position relative to the clamp assembly and secured in place. In another aspect, the clamp assembly further includes a clamp configured to attach the apparatus to a fixture. In another aspect, the clamp assembly further comprises a member extending from the base clamp into a receiver of a pole clamp, member rotatable in the receiver.

Another innovation is an extremity stabilization apparatus, including means for receiving a limb of a patient, the limb receiving means having a longitudinal axis extending from a back end of the cuff to a front end of the cuff, means for receiving the hand of a patient, the hand receiving means disposed offset at a distance from the front end of the limb receiving means and rotatable in a plane normal to the longitudinal axis of the limb receiving means, and means for changing the angle of the limb receiving means, the angle changing means movable to change the position of the top surface of the limb receiving means. In some embodiments, the apparatus further comprises means for moving the hand receiving means in a plane parallel to the longitudinal axis of the limb receiving means. In some embodiments, the apparatus is attached to a support stand as an option to position the device in such a way that promotes proper support and stabilization of the patient's limb during venous access. In various embodiments, the limb receiving means comprises a cuff, the hand receiving means comprises a handle, and the means for changing the angle of the limb receiving means comprises an assembly coupled to the cuff, the assembly movable between at least a first position and a second position to change the position of a top surface of the cuff, each of the first position and second positions corresponding to a different angle of the top surface of the cuff.

Another embodiment includes a method of holding an extremity of a patient in an extremity holding apparatus, the method including receiving an arm of a patient in a cuff, the cuff having a curved surface with a center portion, side portions of the cuff extending from the center portion, a front portion of the cuff and a back portion of the cuff. The method can further include receiving a hand of the patient on a handle of the apparatus, the handle positioned offset from the front portion of the cuff, and elevating the back portion of the cuff to place the patient's forearm at an angle relative to a base portion of the apparatus.

BRIEF DESCRIPTION OF THE DRAWINGS

The features and advantages of the devices described herein will become more fully apparent from the following description and appended claims, taken in conjunction with the accompanying drawings. These drawings depict only several embodiments in accordance with the disclosure and are not to be considered limiting of its scope. In the drawings, similar reference numbers or symbols may but do not always identify similar components (e.g., unless context of the description for each of the figures dictates otherwise). For example, different embodiments/figures may use a similar reference number to indicate a different component, as they are described in the disclosure; accordingly, the reference numbers should be interpreted based on the description of the particular figure. In some instances, the drawings may not be drawn to scale.

FIGS. 2A and 2B are orthogonal views of an embodiment of the handle assembly of the extremity stabilization apparatus. FIGS. 2C thru 2F are front views of various embodiments of the handle assembly that illustrate the various shapes of the handle of an Extremity Stabilization Apparatus.

FIG. 6A is an isometric view of an embodiment of a modular clamp assembly of an extremity stabilization apparatus.

FIG. 6B are orthogonal views of the embodiment shown in FIG. 6A.

FIGS. 13A-C illustrate an embodiment of the Extremity Stabilization Apparatus that is fixedly attached to a rotating handle assembly. FIG. 13A illustrates one position, and FIG. 13B illustrates a second position. FIG. 13C further illustrates certain components. In this embodiment the axis of rotation of the handle assembly stays fixed relative to the cuff. This allows the patient to place their limb into the cuff, and hold the handle. From there the healthcare provider can rotate the patient's hand to any desired position without the patient's limb coming out of the cuff. This is ideal for different vein access points based on the rotation of the patient's hand.

FIG. 15 is an embodiment of the Extremity Stabilization Apparatus shown in FIG. 14 that is slideably and rotatably coupled to the crossbar member of a chair. This allows for the Extremity Stabilization Apparatus to be translated to the left or right side of the chair based on the preferred limb for therapy. The Extremity Stabilization Apparatus in this embodiment is also slideably and rotatably coupled to the crossbar to accommodate the ideal angle and displacement of the cuff and handle assemblies based on a particular patient's anatomy (short or tall).

FIG. 26A is a side view of an embodiment of the Mobile Extremity Stabilization Apparatus with the extremity receiving cuff rotated (or angled) relative to the cuff base.

FIG. 26B is a side view of the Mobile Extremity Stabilization Apparatus with no rotation (or angle) between the extremity receiving cuff and the cuff base.

FIG. 26C is an isometric view of the embodiment shown in FIG. 26A.

FIG. 28A is a side view of an embodiment of the extremity receiving cuff and the handle.

FIG. 28B is side view of the embodiment shown in FIG. 28A with the handle rotated relative to the extremity receiving cuff.

FIG. 30A is a side view of an embodiment of the Mobile Extremity Stabilization Apparatus.

FIG. 30B is a side, sectional view of the embodiment shown in FIG. 30A.

FIG. 30C is a side view of the embodiment shown in FIG. 30A with the extremity receiving cuff rotated relative to the cuff base.

FIG. 30D is a side view of an embodiment of the locking pin.

FIG. 31 is an isometric view of an embodiment of the Mobile Extremity Stabilization Apparatus attached to a removable stand.

FIG. 32A is a side view of an embodiment of the Mobile Extremity Stabilization Apparatus containing a pressurized cylinder configured to provide force to change the angle between the cuff and the base.

FIG. 32B is a bottom view of the embodiment shown in FIG. 32A.

FIG. 33A is an isometric view of embodiments of containers removably attached to extremity receiving cuff.

FIG. 33B is a detailed side view of the removable container attached to the cuff attachment tube of the extremity receiving cuff.

DETAILED DESCRIPTION OF CERTAIN INVENTIVE ASPECTS

The following detailed description is directed to certain specific embodiments of the invention. However, the invention can be embodied in a multitude of different ways. It should be apparent that the aspects herein may be embodied in a wide variety of forms and that any specific structure, function, or both being disclosed herein is merely representative of one or more embodiments of the invention. An aspect disclosed herein may be implemented independently of any other aspects and that two or more of these aspects may be combined in various ways. For example, different embodiments of a device (e.g., a limb stabilization device) may be implemented using any number of the aspects/features disclosed herein. In addition, such a device may be implemented or such a method may be practiced using other structure, functionality, or structure and functionality in addition to, or other than one or more of the aspects set forth herein.

Figure 1:
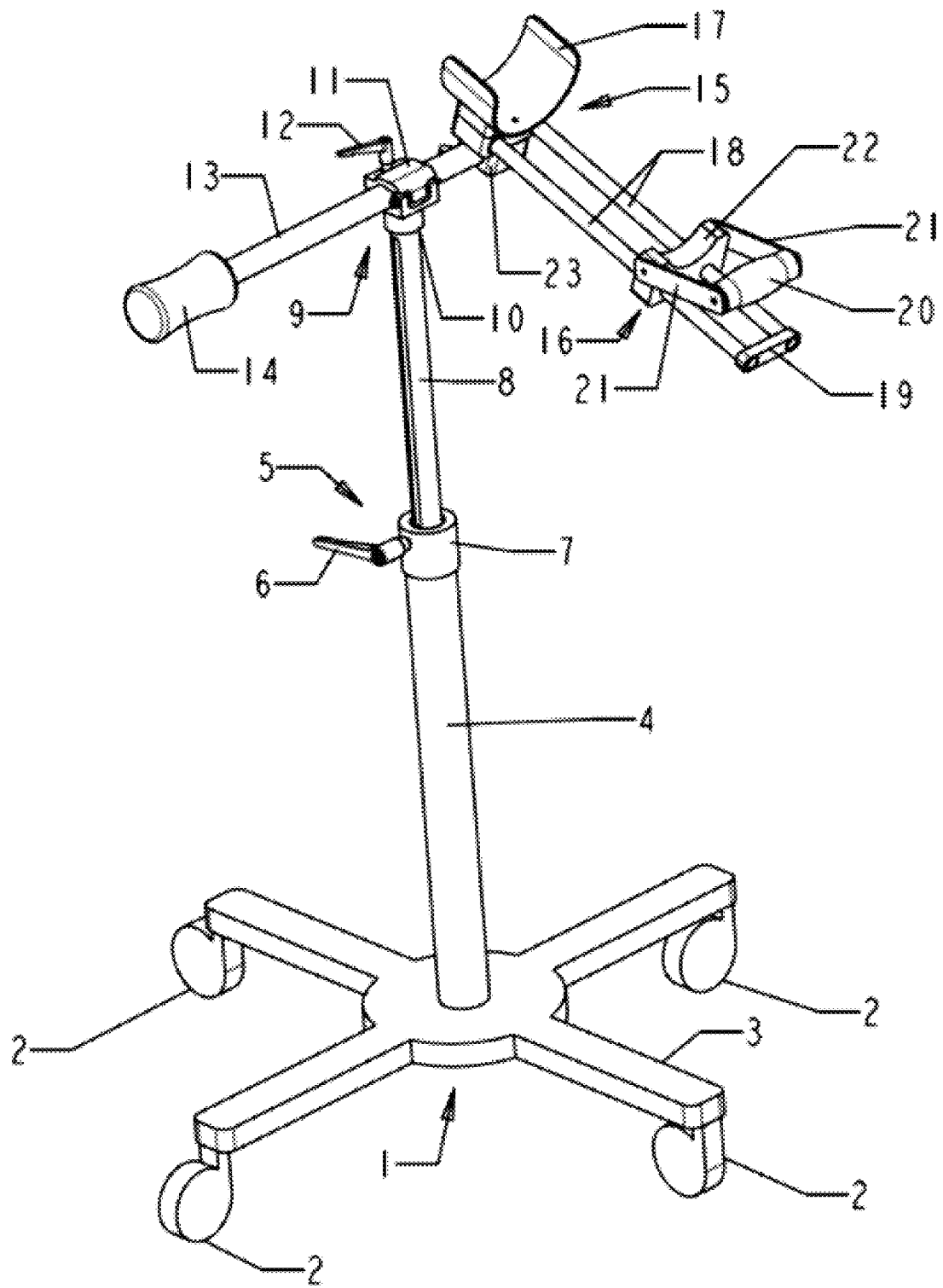
FIG. 1 is an isometric view of portable extremity stabilization apparatus.

FIG. 1 is an illustrated isometric view of an embodiment of the rollable limb stabilization apparatus with a rollable base assembly 1 that is rotatably attached to a series of rollable casters 2. The rollable base assembly 1 in the shown embodiment is fixedly attached to a base extension pole 4. The base extension pole 4 is cannulated to allow for a smaller diameter pole or extension pole 8 to be received through the open portion of the base extension pole 4. In such an embodiment, a threaded coupler 7 connects the base extension pole 4 to the extension pole 8. The threaded coupler 7 is fixedly attached to the base extension pole 4. An extension pole locking handle 6 is threaded at one end and threads into a threaded hole of the threaded coupler 7. Advancement of the extension pole locking handle 6 contacts a surface of the extension pole 8 to hold the extension length. Unthreading the extension pole locking handle 6 from the threaded coupler 7 allows for up and down translational movement of the extension pole 8. In the shown embodiment a fixed receiving end 10 is fixedly attached to the proximal end of the extension pole 8. Rotatably coupled to the fixed receiving end 10 is the rotating receiving end 11 forming an embodiment of the control arm clamp assembly 9. The control arm clamp assembly 9 controls the linear and rotational movement of the control arm 13. The control arm clamp assembly 9 is comprised of a fixed receiving end 10 and a rotating receiving end 11. Both receiving ends are rotatably coupled to one another forming a C shape. The shown control arm handle 12 threads into a female end of the control arm clamp assembly 9 such as a C-Clamp style clamping design. On one end of the control arm 13 is a handle or grip 14 that is fixedly attached to the one end of the control arm 13 and is contoured to fit within a hand.

As used in this disclosure, the "grip" is a broad term referring to the portion of a handle that receives the hand of a patient. In some embodiments, the grip comprises a certain portion of the handle. In other embodiments, the grip may include a component or a material attached to the handle that receives the hand of a patient. The handle, and the grip, may be, for example, metal, a plastic, or a composite material. In some embodiments, the grip include a material other than the handle (e.g., leather, foam, rubber, vinyl or the like). The grip may be advantageously made from a non-porous material for easier sterilization.

Also provided in this embodiment is a rotational means for the Extremity Stabilization Apparatus 15 to rotate about the control arm 13. In such embodiment the Extremity Stabilization Apparatus 15 is rotatably coupled to the control arm 13 by a Extremity Stabilization Apparatus friction clamp 23 that is fixedly attached to the control arm 13. One end of the Extremity Stabilization Apparatus friction clamp 23 is fixedly attached to the control arm 13 with the other rotational end fixedly attached to an extremity receiving cuff 17. In the shown embodiment, the Extremity Stabilization Apparatus friction clamp 23 and the extremity receiving cuff 17 are rotatably coupled such that compression of the two elements locks the rotation of the Extremity Stabilization Apparatus 15 in reference to the plane defined by the control arm 13 and the extension pole 8. Fixedly attached to the extremity receiving cuff 17 are a series of two Extremity Stabilization Apparatus pole(s) 18. The opposite end of the Extremity Stabilization Apparatus poles 18 are secured together and fixedly attached into a receiving end of the cuff pole connector 19. In such an embodiment the grip mount 22 is slideably coupled to the two Extremity Stabilization Apparatus poles(s) 18 to allow for translational movement of the grip mount 22 relative to the position of the extremity receiving cuff 17. In the embodiment shown, the Extremity Stabilization Apparatus handle 20 is fixedly attached to the grip mount 22 on both ends by a handle connector 21. The assembly of the grip mount 22, the handle connector(s) 21 and the grip mount 22 forms the handle assembly 16. An advantage of the shown embodiment is such that the handle assembly 16 is slideably coupled to the extremity receiving cuff 17 to accommodate extremities of varying length. This variability is critical for two reasons. The first reason allows for the proper placement of the distal area of the patient's extremity into the cuff 17 while allowing for the patients hand to comfortably pass through the receiving end defined by the handle assembly 16 and grip the Extremity Stabilization Apparatus handle 20. The second reason allows for the same proper placement of the patient's extremity in the extremity receiving cuff 17 relative to the placement of the hand onto the top of grip mount 22 should the patient's extremity be rotated one hundred and eighty degrees relative to the placement of their extremity referenced in the first reason.

FIGS. 2A, 2B, 2C, 2D, 2E and 2F are different embodiments of the handle assembly 16 shown in FIG. 1 with varying open and closed designs for the showing alternative variations of the Extremity Stabilization Apparatus handle 20 depicted in FIG. 1.

Figure 3A:
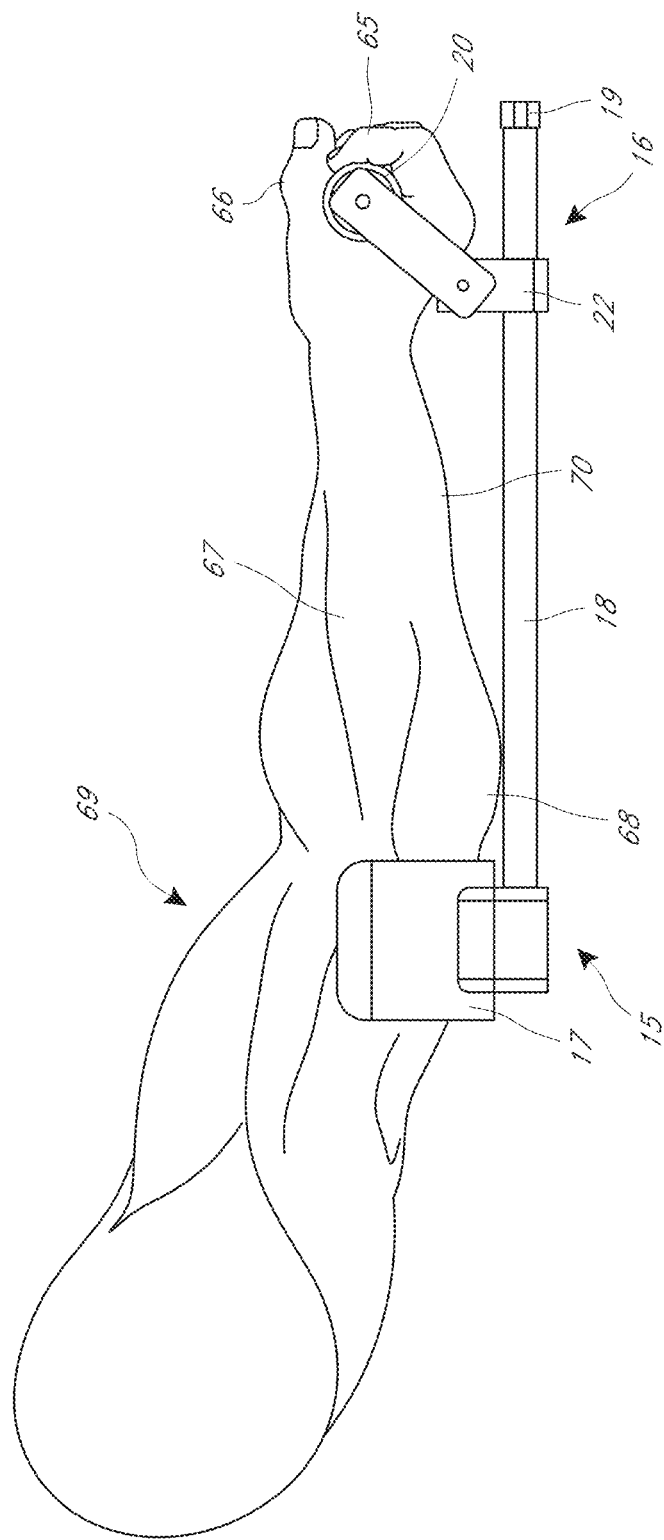
FIG. 3A is a side view of embodiment of the handle assembly slideably coupled to the Extremity Stabilization Apparatus that illustrates the stabilization of a patient's extremity promoting antecubital access during Venipuncture.
Figure 3B:
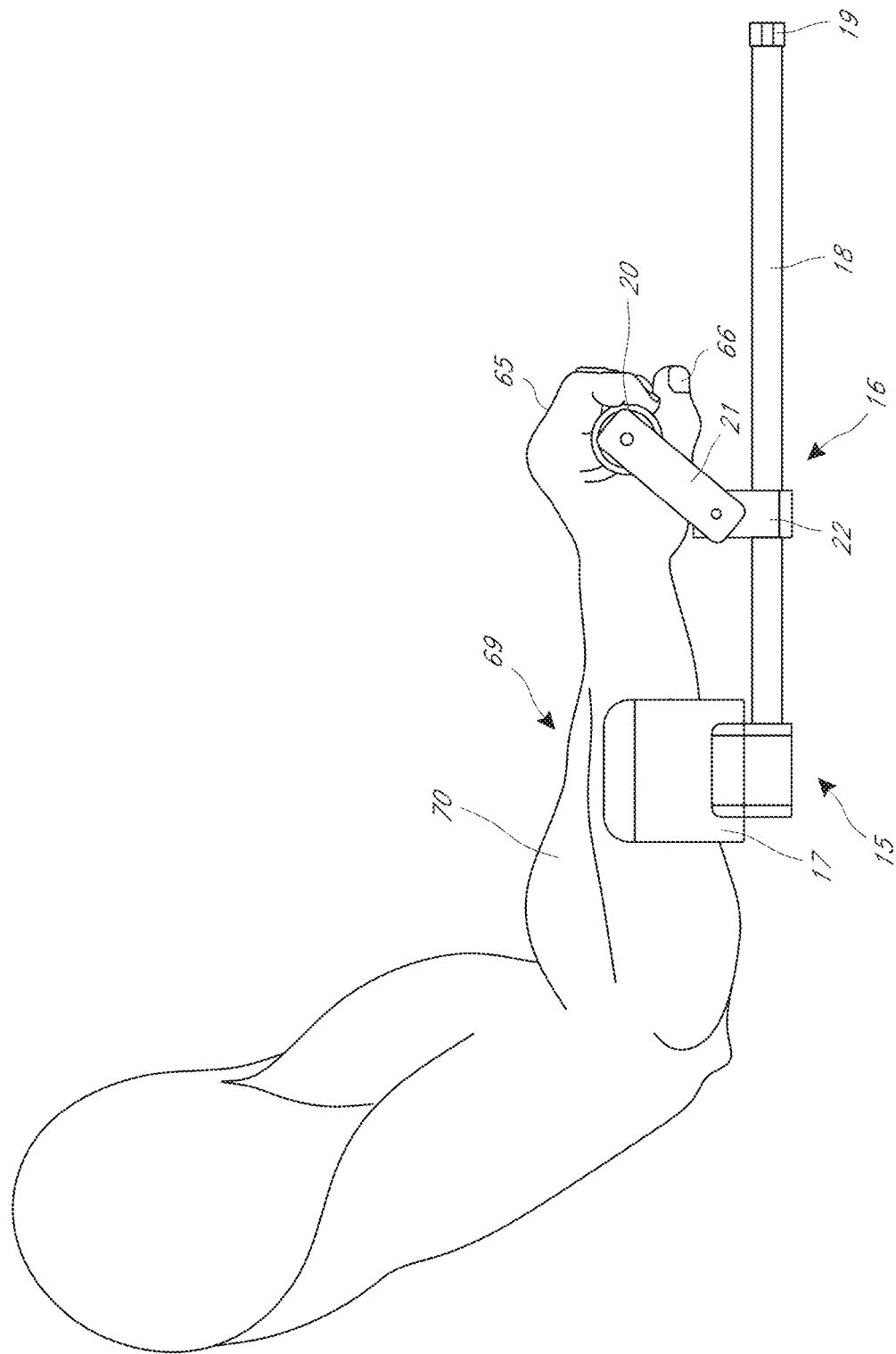
FIG. 3B is a side view of embodiment of the handle assembly slideably coupled to the Extremity Stabilization Apparatus that illustrates the stabilization of a patient's extremity rotated, relative to FIG. 3A, promoting hand access during Venipuncture.

FIGS. 3A and 3B are side views of the Extremity Stabilization Apparatus 15 and the handle assembly 16 as shown in FIG. 1. The embodiments shown in FIGS. 3A and 3B, illustrate the patients extremity 69 disposed within the contoured receiving end of the extremity receiving cuff 17 and also within the aperture created by the handle assembly 16. FIG. 3A is an embodiment of the present invention whereby the patient's elbow 68 is defined between the Extremity Stabilization Apparatus 15 and the handle assembly 16. In the embodiment shown the patients extremity 69 is hyper-extended allowing antecubital access to the anterior side of the patient's forearm 67 during Venipuncture. The patient's elbow 68 is located between the Extremity Stabilization Apparatus 15 and the handle assembly as shown in FIG. 3A to promote the desired hyper-extension of the patient's extremity 69 to allow for antecubital access during Venipuncture. In the embodiment shown in FIG. 3A, the top of the patient's hand 65 extends within the aperture defined by the handle assembly 15 to allow the patient to comfortably grip the Extremity Stabilization Apparatus handle 20 in the palm of their hand, thereby keeping the anterior side of the patient's forearm 67 stabilized and exposed during Venipuncture.

FIG. 3B illustrates an embodiment with the patient's extremity 69 is disposed within the Extremity Stabilization Apparatus 15 and the handle assembly 16 with the top of the patient's hand 65 rests on top of the Extremity Stabilization Apparatus handle 20 to promote distal hand access for Venipuncture. In the embodiment shown in FIG. 3B, the patient's hand can comfortably grip the Extremity Stabilization Apparatus handle 15 in the palm of their hand, thereby keeping the top of the patient's hand 65 stabilized and exposed for Venipuncture to be performed on the top of the patient's hand 65.

Figure 4:
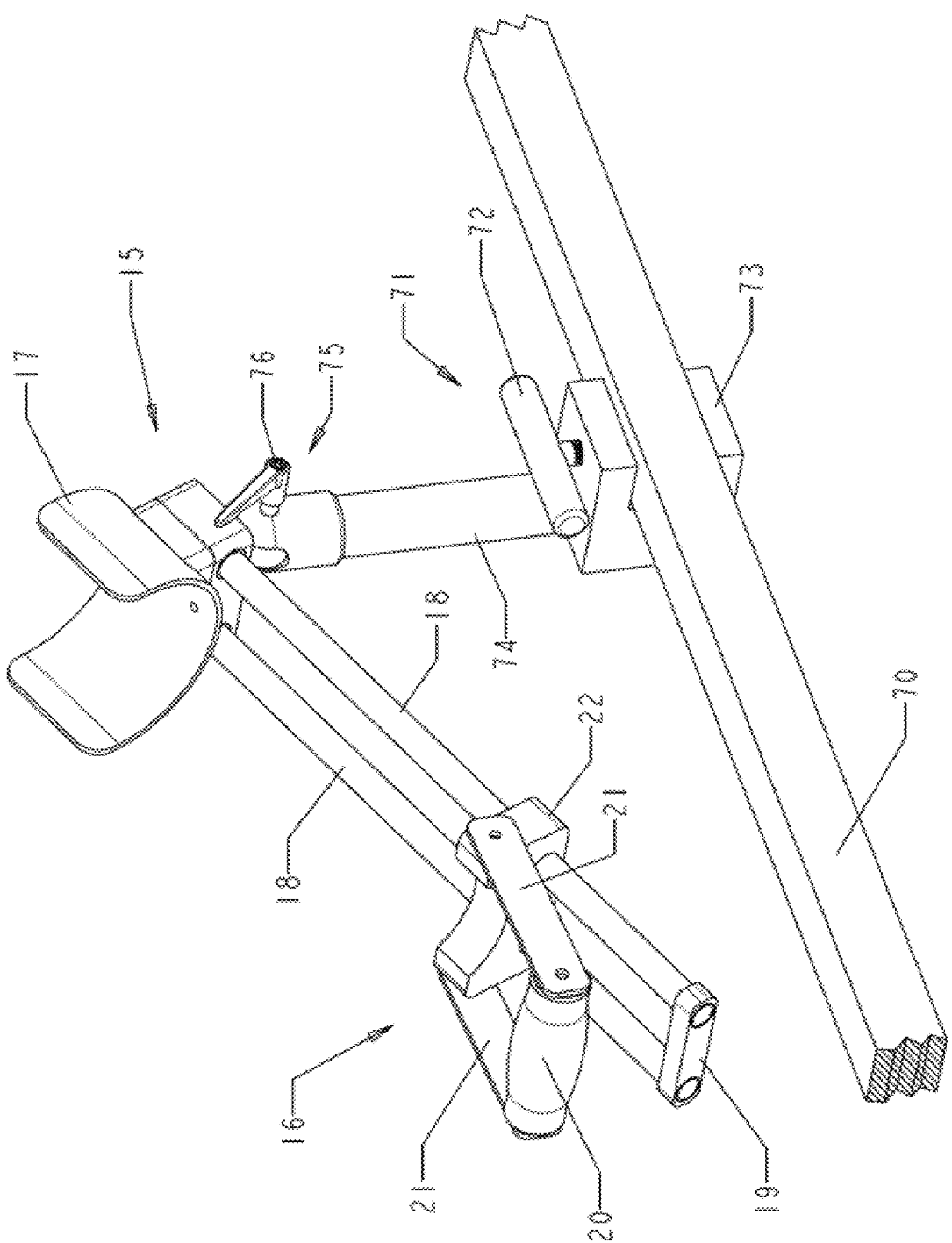
FIG. 4 is an isometric view of an embodiment of an extremity stabilization apparatus fixedly attached to a frame component of a medical bed.

FIG. 4 is an isometric view of an embodiment of the Extremity Stabilization Apparatus 15 and the handle assembly 16 as shown in FIG. 1, together spherically coupled to a fixed clamp assembly 71. In the embodiment shown, the spherical ball joint assembly 75 is locked into any desired position by a threaded joint locking handle 76 to allow for spherical rotation of the Extremity Stabilization Apparatus 15 about a cuff post 74. In the embodiment show, the cuff post 74 is fixedly attached to a fixed clamp assembly 71. In the embodiment shown, the fixed clamp assembly 71 can be fixedly attached at any desired location on a patient bed or chair frame 70. In the embodiment shown, a threaded clamp handle 72 threads into the female receiving end of the clamp 73 until it contacts the surface of a patient bed or chair frame 70.

Figure 5:
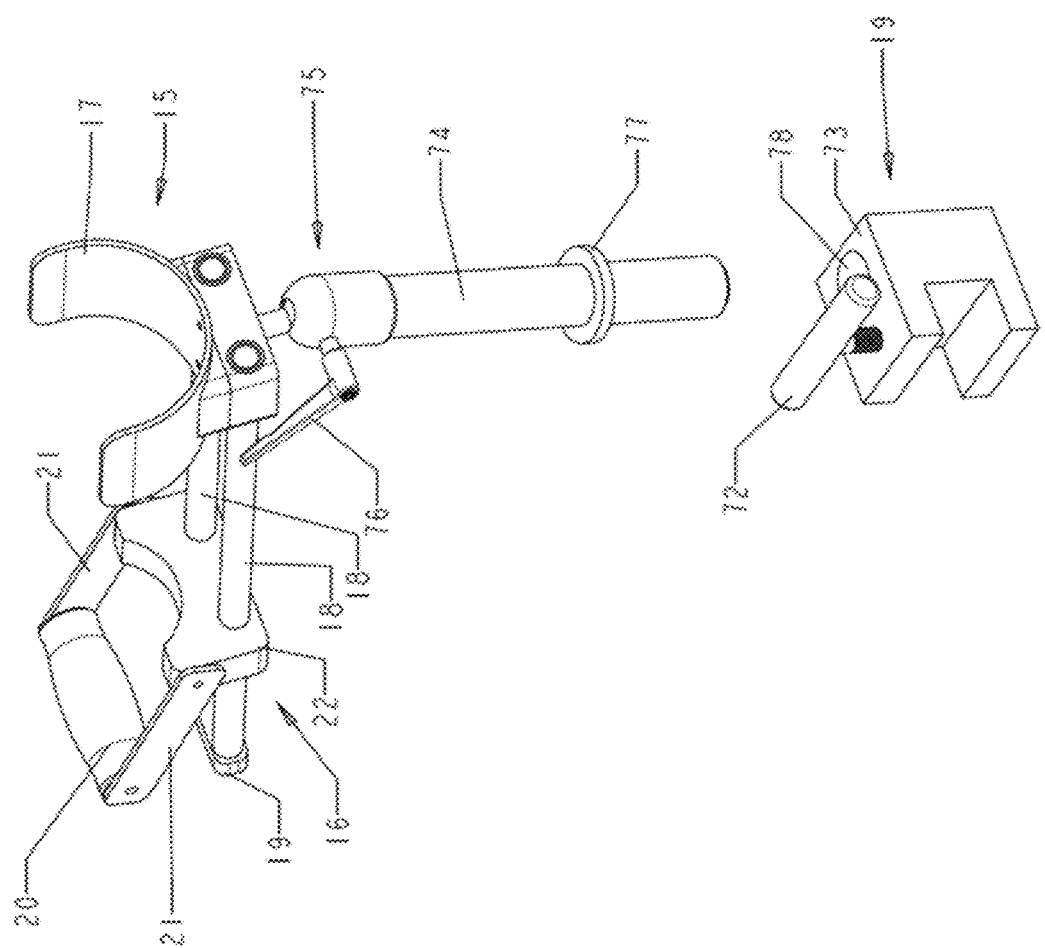
FIG. 5 is an exploded isometric view of an embodiment of an extremity stabilization apparatus removably coupled to a modular clamp assembly.

FIG. 5 is an exploded isometric view of the assembly shown in FIG. 4 with a modular mode of assembly between the cuff post 74 and the fixed clamp assembly 71. In the embodiment shown, the cuff post 74 can be inserted into a female receiving cannula 78 of the modular clamp assembly 79 until the top surface of the modular clamp assembly 79 is in contact with a stop 77, fixedly attached to the cuff post 74. In the embodiment shown, the outer diameter of the stop 77 is larger than the female receiving cannula 78 of the modular clamp assembly 79. Once assembled, the cuff post 74 is rotatably coupled to the modular clamp assembly 79.

FIG. 6A is an isometric view of an embodiment of the modular clamp assembly 79 shown in FIG. 5. In FIG. 6A, the embodiment shown has a second locking handle 80 that is threadably coupled to female receiving end of the clamp 73 such that it enters the channel defined by the female receiving cannula 78 to lock the rotational and translational position of the cuff post 74. FIG. 6B are orthogonal views of the embodiment shown in FIG. 6A.

Figure 7:
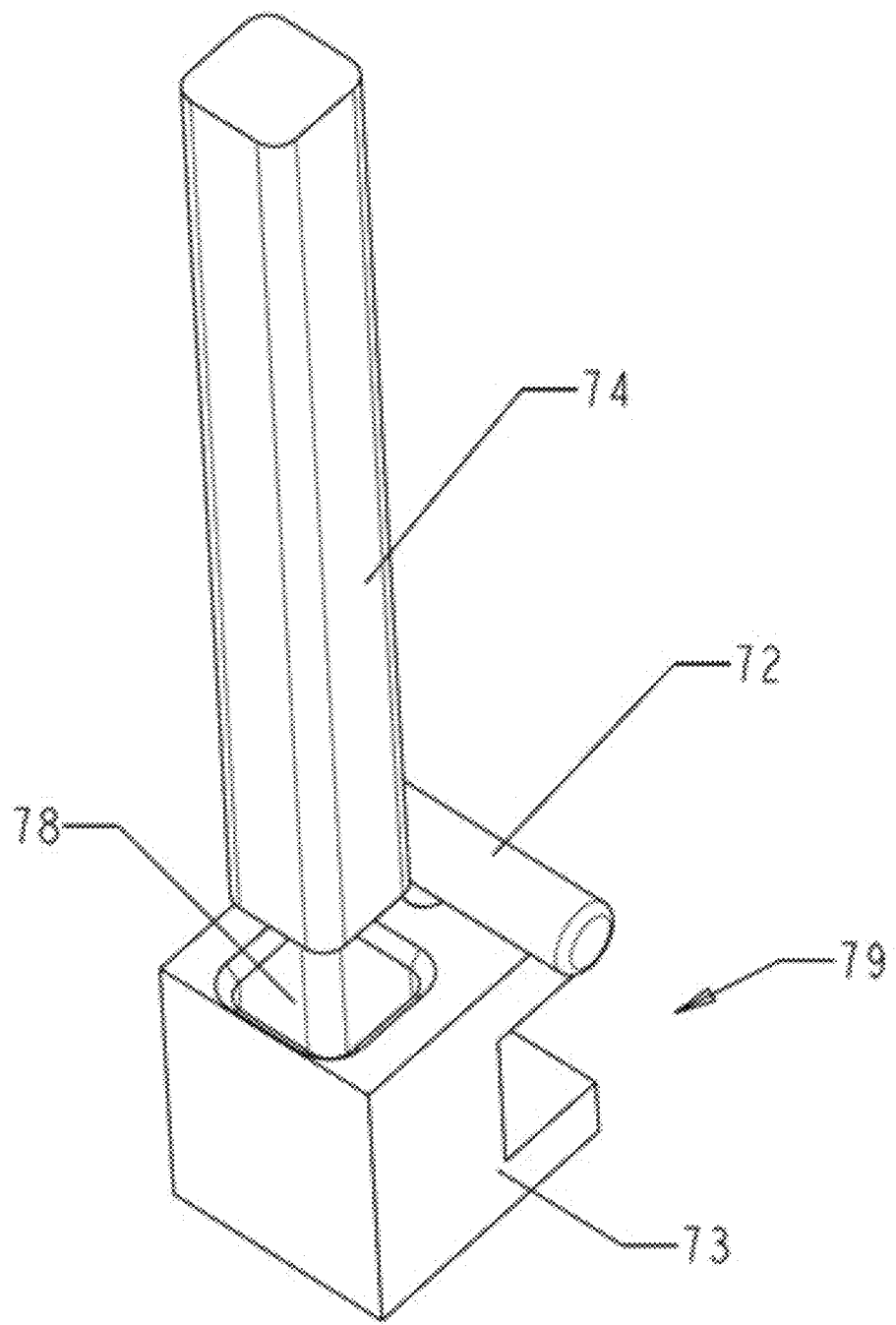
FIG. 7 is an exploded isometric view of an embodiment of a cuff post of an extremity stabilization apparatus removably coupled to a modular clamp assembly.

FIG. 7 is an isometric exploded view of an embodiment of the modular clamp assembly 79 in FIG. 5. In the embodiment shown, the cuff post 74 has a polygonal shape that is slideably the female receiving cannula 78 of a slightly larger polygonal shape.

Figure 8:
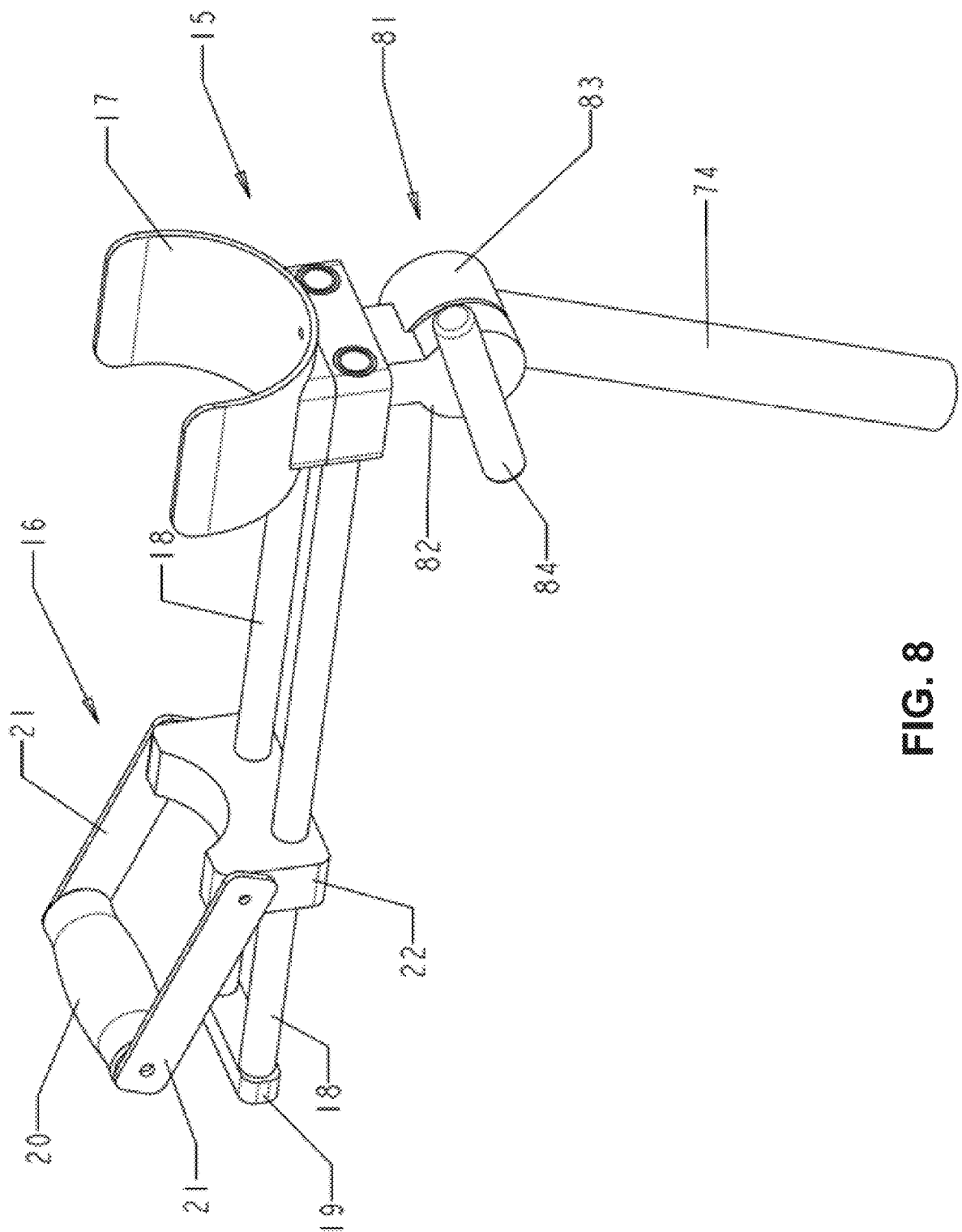
FIG. 8 is an isometric view of an embodiment of the hand assembly and Extremity Stabilization Apparatus rotatably coupled to a rotational Extremity Stabilization Apparatus.

FIG. 8 is an isometric view of an embodiment of the modular Extremity Stabilization Apparatus 15 and handle assembly 16 shown in FIG. 5 with a rotational Extremity Stabilization Apparatus 81. In the embodiment shown, the extremity receiving cuff 17 is fixedly attached to a rotational end 82. The rotational end 82 is rotatably coupled to the cuff post rotational end 83. In the embodiment shown, the relative rotation of the rotational end 82 and the cuff post rotational end 83 is locked into position by tightening the surface of one against the other by a threaded handle 84.

Figure 9:
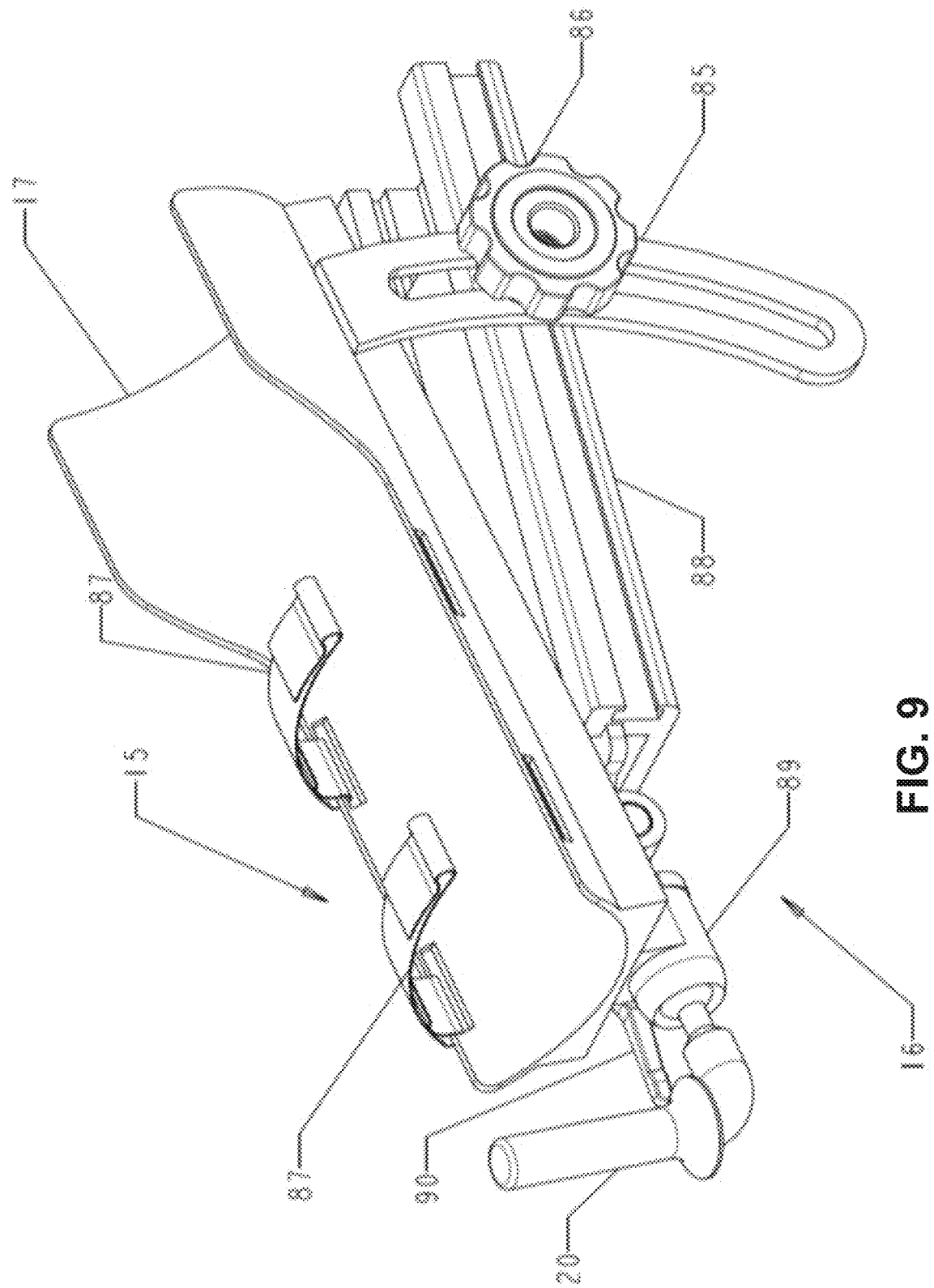
FIG. 9 is an isometric view of an embodiment of the cuff that is spherically attached to the hand assembly with the cuff also rotatably and slideably attached to a base altogether comprising the Extremity Stabilization Apparatus.

FIG. 9 is an isometric view of a particular embodiment of the modular Extremity Stabilization Apparatus 15 and handle assembly 16. In this embodiment, the extremity receiving cuff 17 has optional cuff straps 87 attached at one or more points. The Extremity Stabilization Apparatus 15 is both slideably and rotatably coupled to the sliding base 88 with both the rotational and sliding movements locked into place at once by tightening the tilt rail knob 86. The tilt rail 85 if fixedly attached to the modular Extremity Stabilization Apparatus 15 allowing the tilt rail 85 to rotate in any desired position. The handle assembly 16 is fixedly attached to the extremity receiving cuff 17 combined to create the modular Extremity Stabilization Apparatus 15. The Extremity Stabilization Apparatus handle 20 is spherically attached to the spherical coupler 89 of the handle assembly and locked into any desired position with the spherical coupler handle 90.

Figure 10:
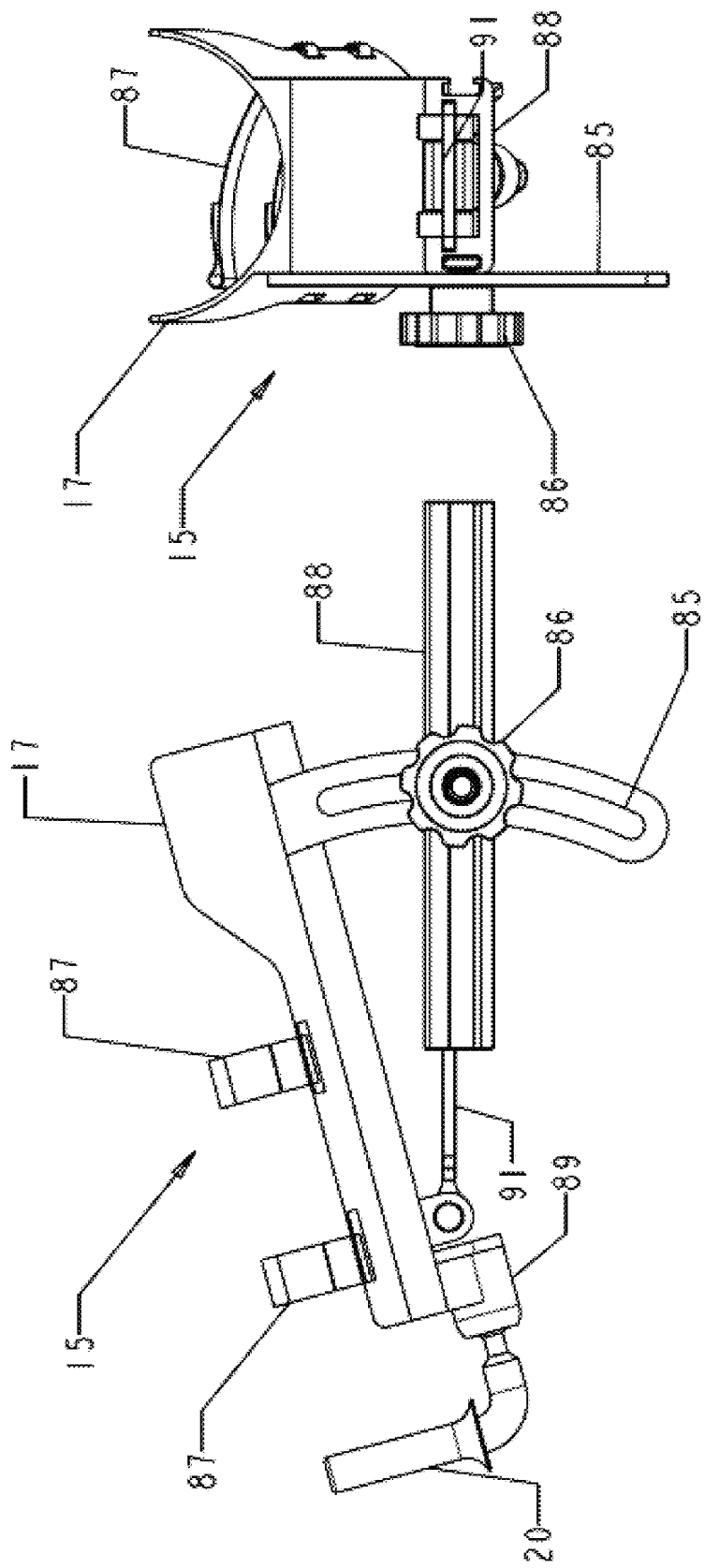
FIG. 10 shows back and side views of the embodiment shown in FIG. 9.

FIG. 10 is a side and back view of an embodiment of the modular Extremity Stabilization Apparatus 15 with handle assembly 16 shown in FIG. 5. In this embodiment, the extremity receiving cuff 17 is rotatably coupled to the rotating rail 91 with rotation of the extremity receiving cuff 17 locked in any desired position by tilt rail knob 86. The rotating rail 91 is also slideably coupled to the sliding base 88 and locked into position by tightening the tilt rail knob 86. Tightening of the tilt rail knob 86 compresses the tilt rail 85 against the side of the sliding base 88. The tilt rail knob 86 controls both the rotation of the extremity receiving cuff 17 relative to the sliding base 88 and also controls the linear position of the extremity receiving cuff 17 relative to the sliding base 88.

Figure 11:
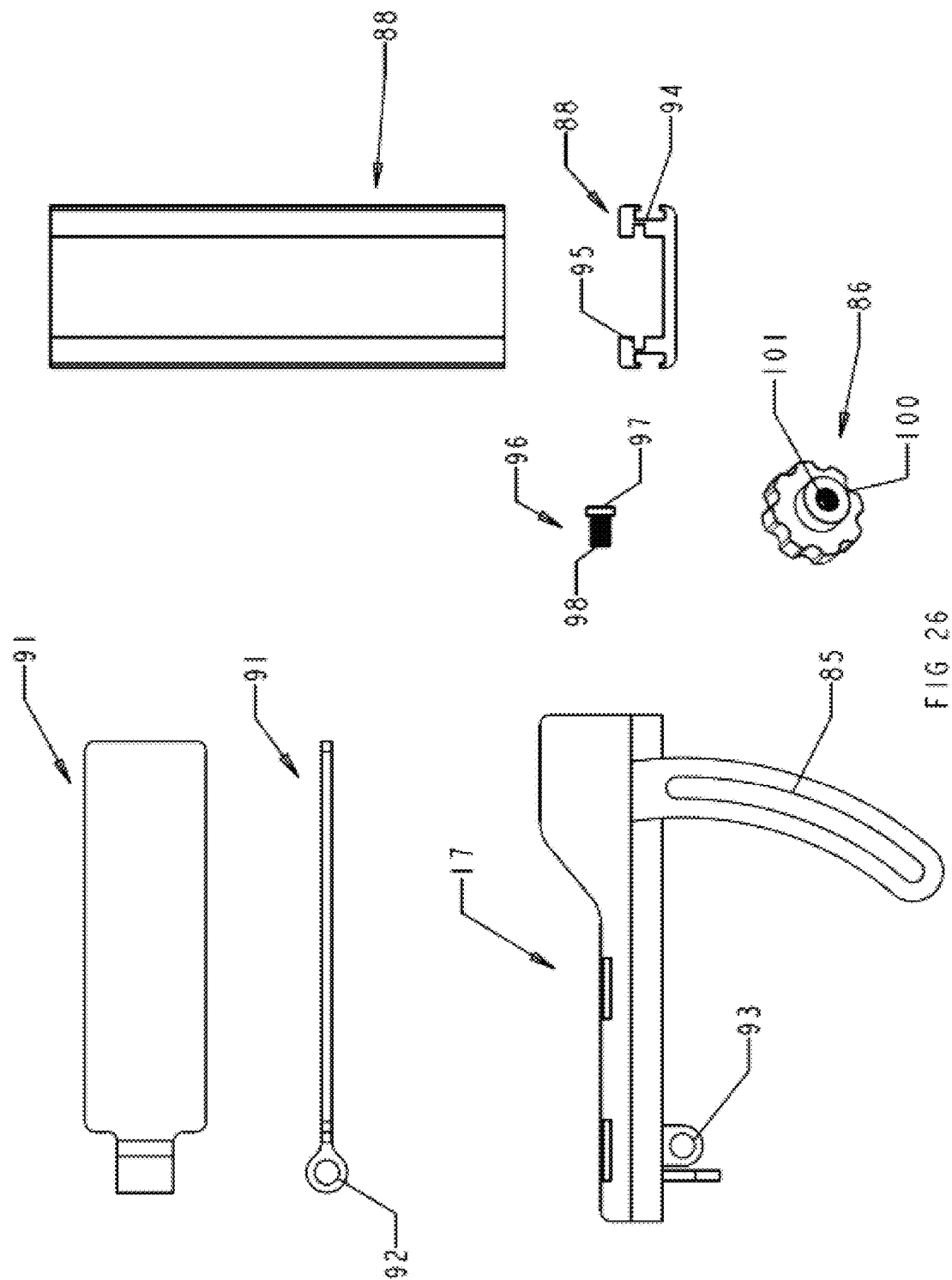
FIG. 11 are various views of various components of the Extremity Stabilization Apparatus shown in FIG. 9.

FIG. 11 shows various views of the components of the modular Extremity Stabilization Apparatus 15 shown in FIG. 9. The rotating rail 91 is rotatably coupled to the extremity receiving cuff 17 and connected between the rotating rail hinge 92 and the cuff hinge 93. The tilt rail knob 86 threads onto roller thread 98 of the threaded roller 96. The roller flange 97 is linearly coupled to the sliding base 88 and translates throughout the t slot 95 created on both sides of the sliding base 88 with the roller thread 98 protruding through the open end of the t slot 94 and protruding through the tilt rail 85. The rotating rail 91 is slideably coupled to the sliding base 88 and is disposed within the rail slots 95 of the sliding base 88.

Figure 12:
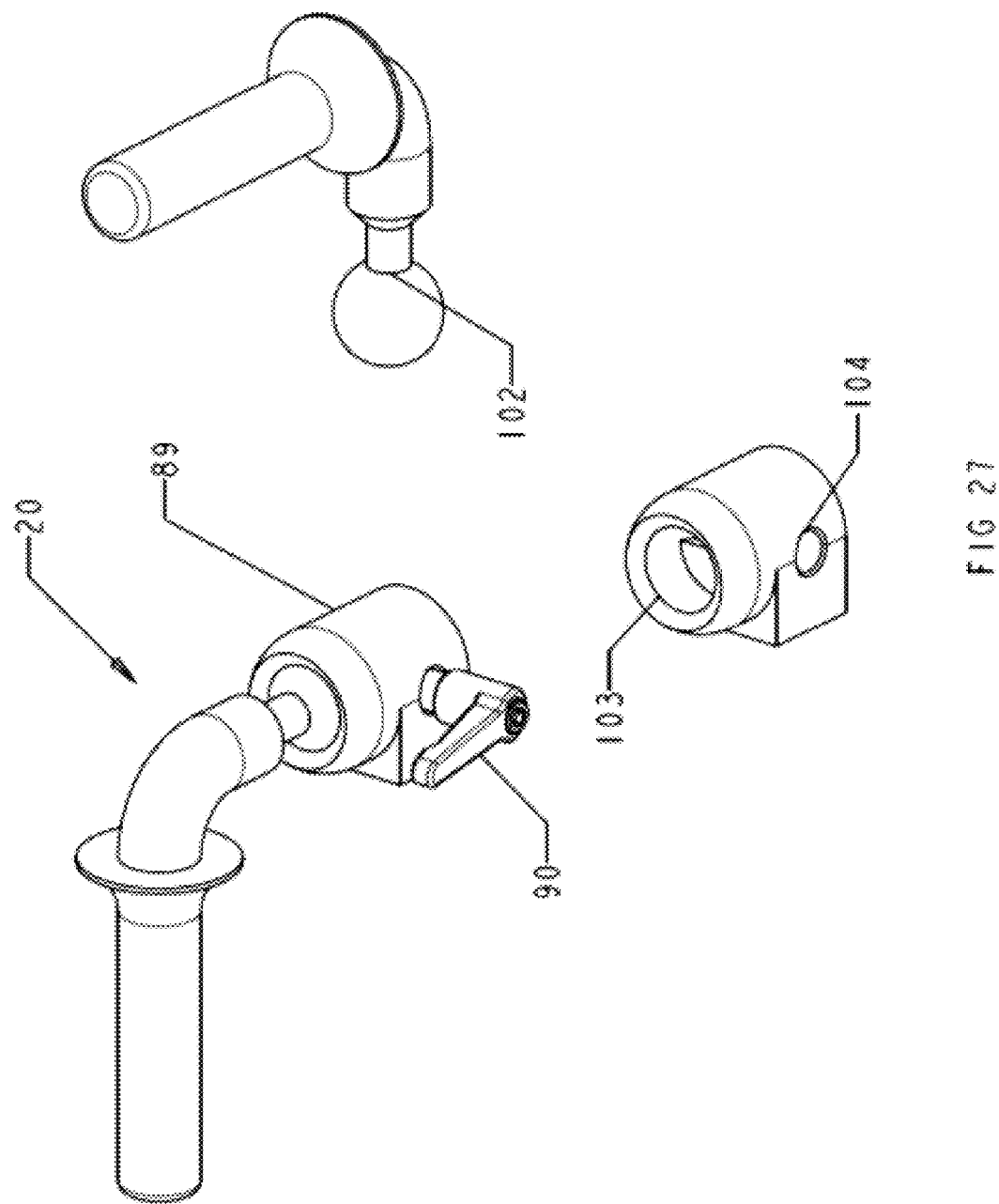
FIG. 12 are various views of components of the spherically coupled hand assembly shown in FIG. 9.

FIG. 12 is an isometric view of the Extremity Stabilization Apparatus handle 20 of the embodiment of the modular Extremity Stabilization Apparatus 15 shown in FIG. 9. The Extremity Stabilization Apparatus handle 20 is spherically coupled to the spherical coupler 89 and locked into position with the spherical coupler handle 90. The spherical head 102 of the Extremity Stabilization Apparatus handle 20 is disposed within the spherical coupler cavity 103 of the spherical coupler 89. The spherical coupler handle 90 threads into the threaded hole 104 of the spherical coupler. As the spherical coupler handle 90 advances, it contacts the surface of the spherical head 102 thereby locking the position.

FIG. 13A is an isometric view of an embodiment of the Extremity Stabilization Apparatus 15. In this particular embodiment the extremity receiving cuff 17 is fixedly attached to the rotating cuff linkage 125, whereby the rotating cuff linkage 125 is rotatably coupled to the rotating handle 123. The rotating handle 123 is free to rotate 360 degrees. The rotational position of the rotating handle 123 is locked by threading the rotating handle knob 127 to the rotating handle screw 126, whereby the advancement of the rotating handle knob 127 compresses the rotating handle 123 to the rotating handle linkage 125, together forming the rotating handle assembly 124.

FIG. 13B is an isometric, exploded view of the Extremity Stabilization Apparatus 15 embodiment shown in FIG. 13A. FIG. 13C is an isometric view of the Extremity Stabilization Apparatus 15 embodiment shown in FIG. 13A, illustrating the rotation of the rotating handle 123 relative to the Extremity Stabilization Apparatus 15.

Figure 14A:
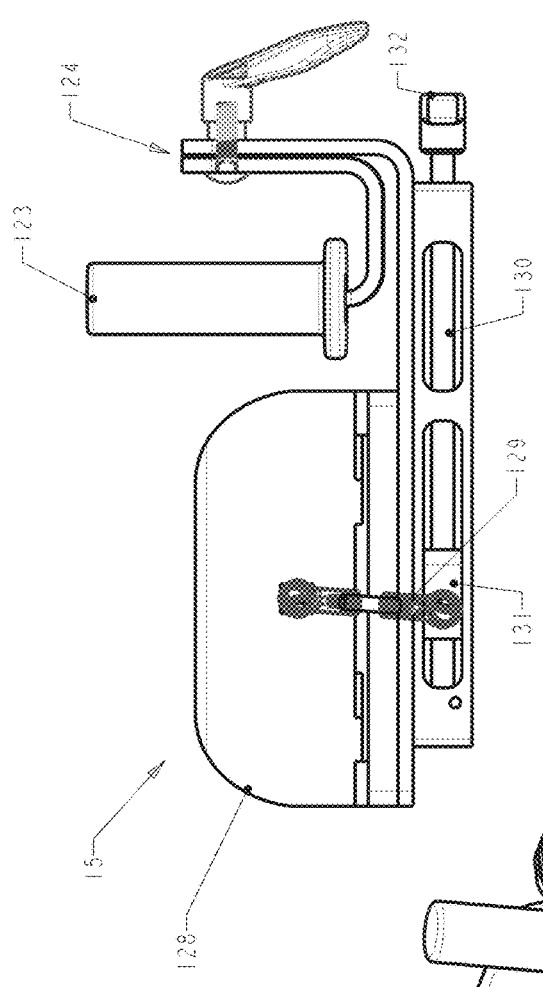
FIGS. 14A-E illustrate is an embodiment of the Extremity Stabilization Apparatus shown in FIG. 13 with the addition of a cuff adjustment that changes the shape of the cuff. This allows for the relative size and shape of the cuff to be adjusted to fit different patient anatomies both large and small.
Figure 14B:
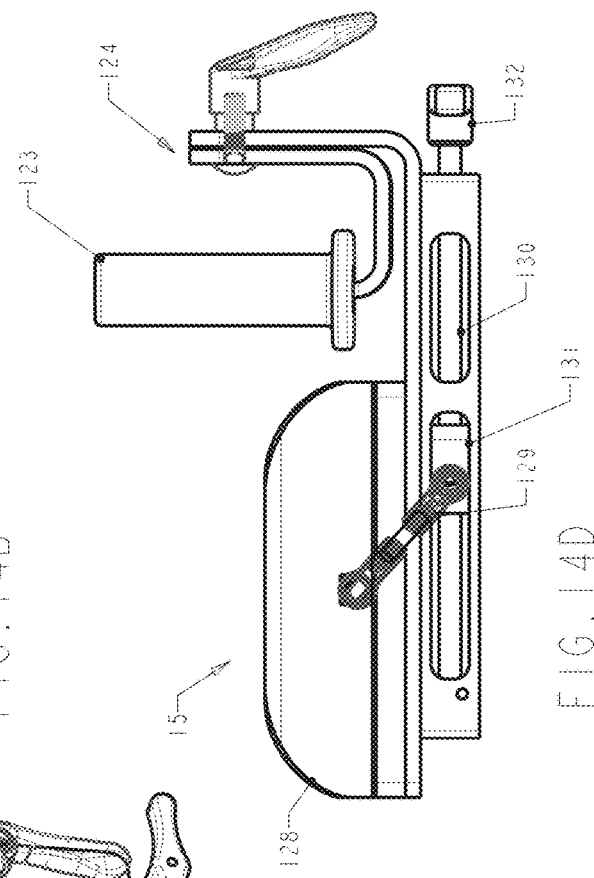
Figure 14C:
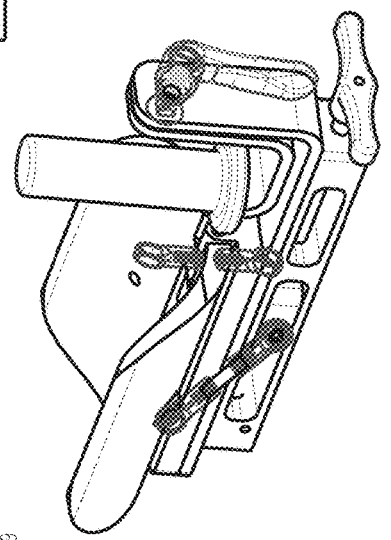
Figure 14D:
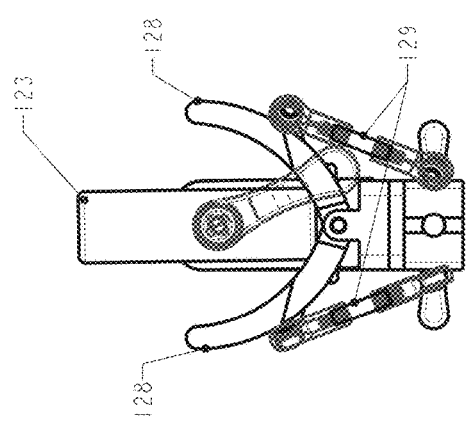
Figure 14E:
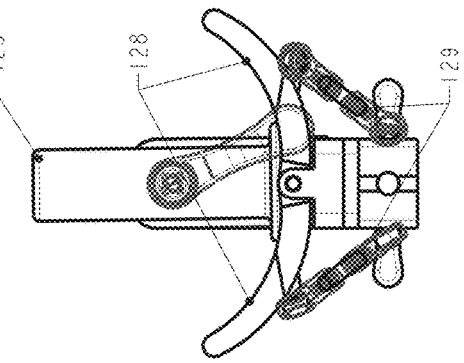

FIGS. 14A-14B are embodiments of the Extremity Stabilization Apparatus 15 shown in FIG. 13A whereby the extremity receiving cuff 17 is split into two halves allowing both halves to open and close. FIG. 14A is a back view of the Extremity Stabilization Apparatus 15 whereby two adjustable cuffs 128 are hingedly attached together, their rotational position controlled by an adjustable cuff connector 129. The adjustable cuff connector 129 is rotatably coupled to the adjustable cuff 128 at one end and to the lead screw carriage 131 at the other end. As the adjustable cuff lead screw 130 rotates, the lead screw carriage translates allowing the connected adjustable cuffs 128 to open and close. The rotation of the adjustable cuff lead screw 130 is fixedly attached to an adjustable cuff handle. FIG. 14B is a projected side view of FIG. 14A, illustrating the position of the lead screw carriage 131 to the angulation or rotation of the adjustable cuff 128. This would be considered the "closed" position of the adjustable cuffs 128. Alternatively, FIGS. 14C and 38d are similar projected views, however they illustrate the position of the lead screw carriage 131 relative to the rotation of the adjustable cuff 128. This would be considered the "open" position of the adjustable cuffs 128. FIG. 14E is an isometric view of the Extremity Stabilization Apparatus 15 embodiment show in FIGS. 14A thru 14D.

FIG. 15A is an isometric view of an embodiment of the Extremity Stabilization Apparatus 15 slideably attached to the crossbar 137 of a chair 105. FIG. 15B is a side view of FIG. 15A.

Figure 16:
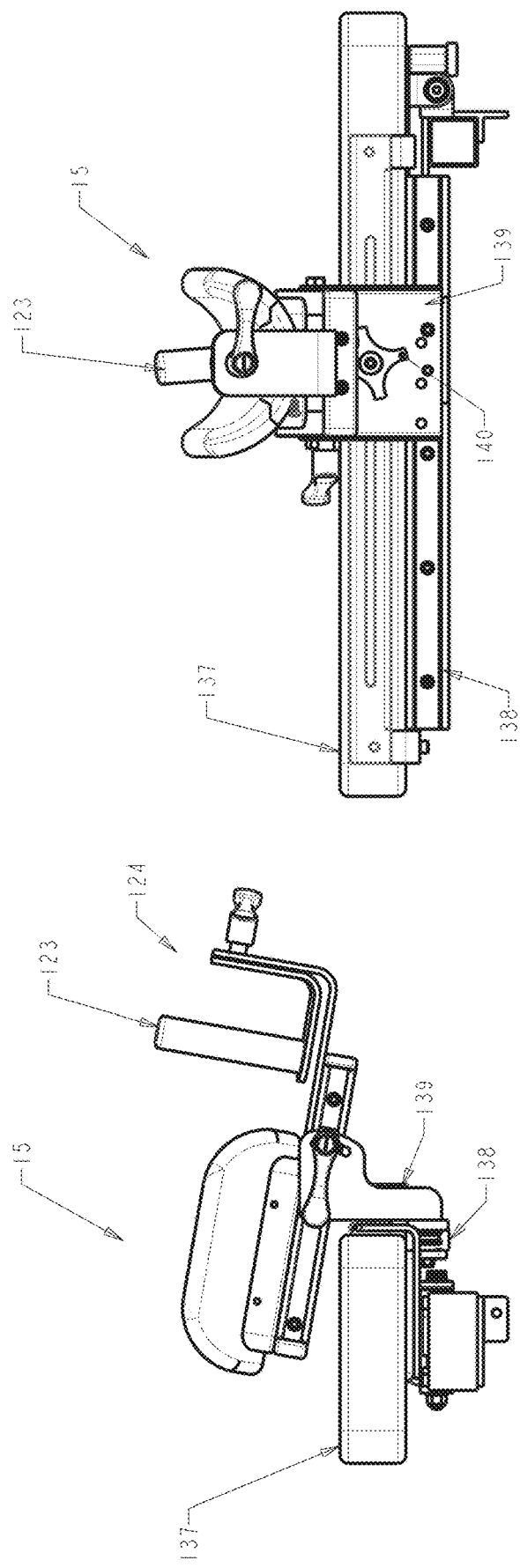
FIG. 16 is a more detailed illustration of the Extremity Stabilization Apparatus embodiment shown in FIG. 15 as it is slideably coupled to the crossbar of the chair.

FIG. 16A is a side view of the embodiment of the Extremity Stabilization Apparatus 15 shown in FIG. 15A. The Extremity Stabilization Apparatus 15 is both slideably and rotatably attached to the extremity stabilization apparatus hinge 139. In this embodiment, the extremity stabilization apparatus hinge 139 is slideably attached to the crossbar guide rail 138. The crossbar slide knob 140 locks the sliding position of the Extremity Stabilization Apparatus 15 relative to the crossbar. FIG. 16B is a front view of FIG. 16a.

Figure 17:
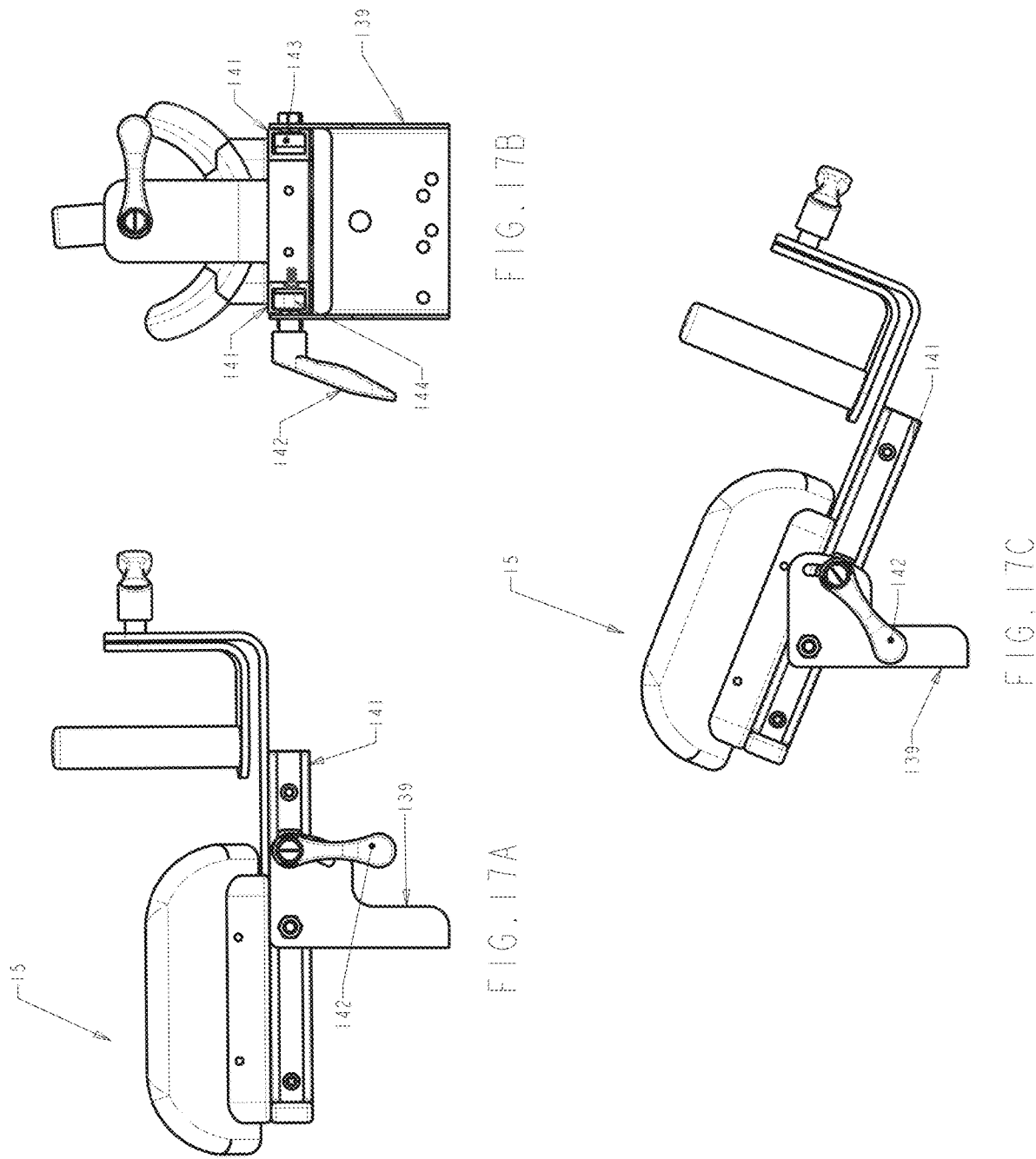
FIGS. 17A-C are more detailed illustrations of the Extremity Stabilization Apparatus embodiment shown in FIG. 15 and how it may be both slideably and rotatably coupled to the crossbar.

FIG. 17A is a side view of the embodiment of the Extremity Stabilization Apparatus 15 shown in FIG. 15A. FIG. 17B is a side view of FIG. 15A. In this embodiment the Extremity Stabilization Apparatus 15 has two cuff rails 141 fixedly attached to either side of the Extremity Stabilization Apparatus 15. The cuff rails 141 is slideably and rotatably coupled to the cuff rail bearing 143 on both sides of the cuff rails 141. The cuff rail bearing 143 is fixedly attached to the extremity stabilization apparatus hinge 139. The cuff rail 141 is also slideably coupled to a cuff rail follower 144. The cuff rail follower 144 is attached to the cuff rail knob 142. Tightening of the cuff rail knob 142 to the cuff rail follower 144 clamps the cuff rail 144 to the extremity stabilization apparatus hinge 139 therefore locking the translational and rotational position of the Extremity Stabilization Apparatus 15. FIG. 17C is an isometric view of the embodiment shown in FIG. 17A.

Figure 18:
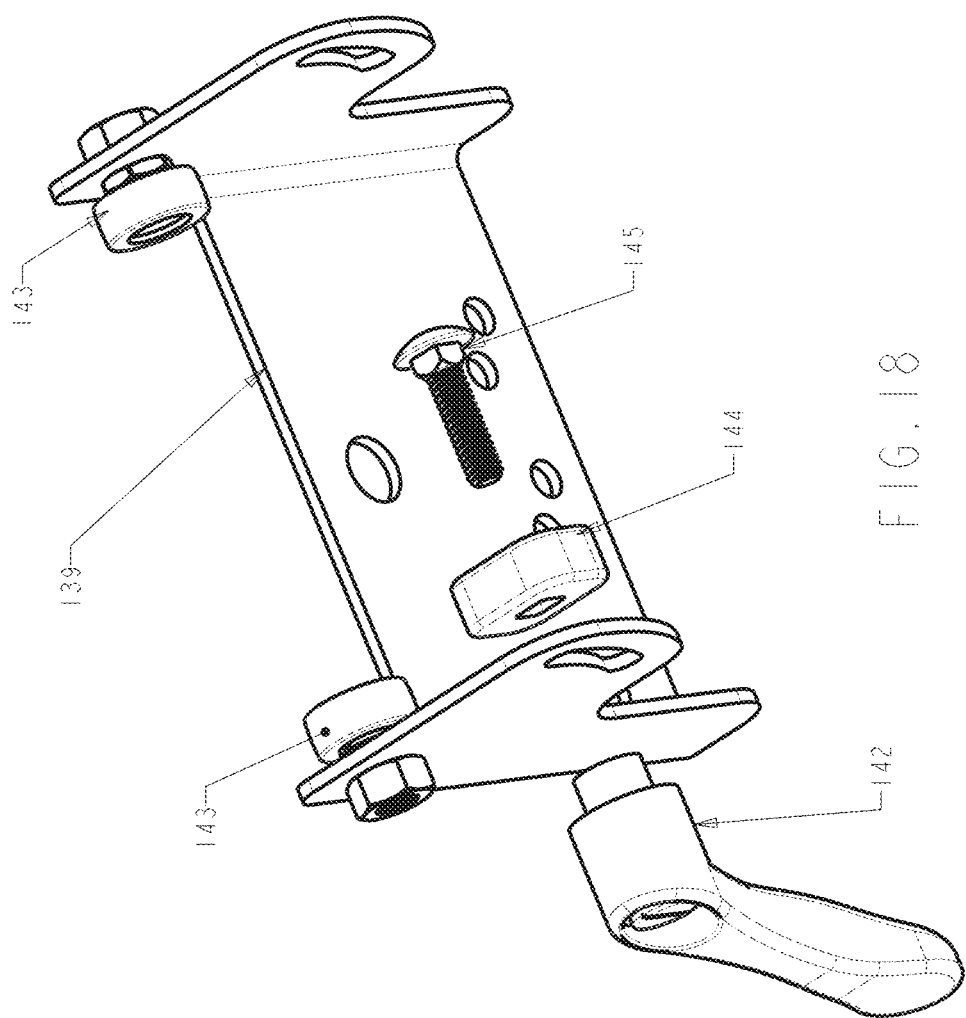
FIG. 18 illustrates details of the locking assembly of the embodiment shown in FIG. 17.

FIG. 18 is an isometric view of the cuff rail knob 142, cuff rail bearings 143, cuff rail follower 144 and extremity stabilization apparatus hinge 139 assembly shown in FIGS. 17A thru 17C. Additionally shown is the cuff rail follower screw 145 that is threadably coupled to the cuff rail knob

142. As the cuff rail knob 142 is tightened onto the cuff rail follower screw 145, it pulls the cuff rail follower 144 into the crossbar guide rail 138, which in turn locks the translational and rotational position of the cross bar guide rail 138 to the extremity stabilization apparatus hinge 139.

Figure 19B:
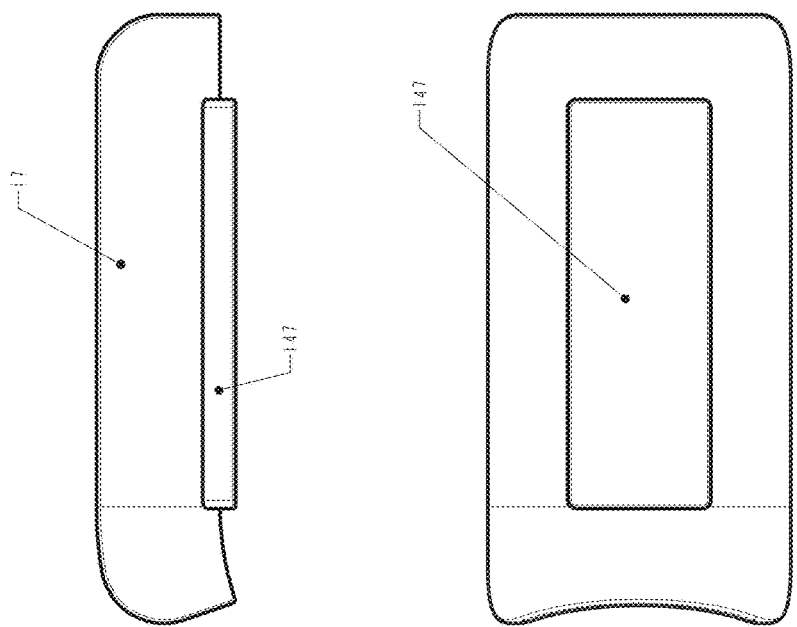
FIG. 19B is a detailed view of an embodiment of the Extremity Receiving Cuff, illustrating the modular features inherent to the design.
Figure 19A:
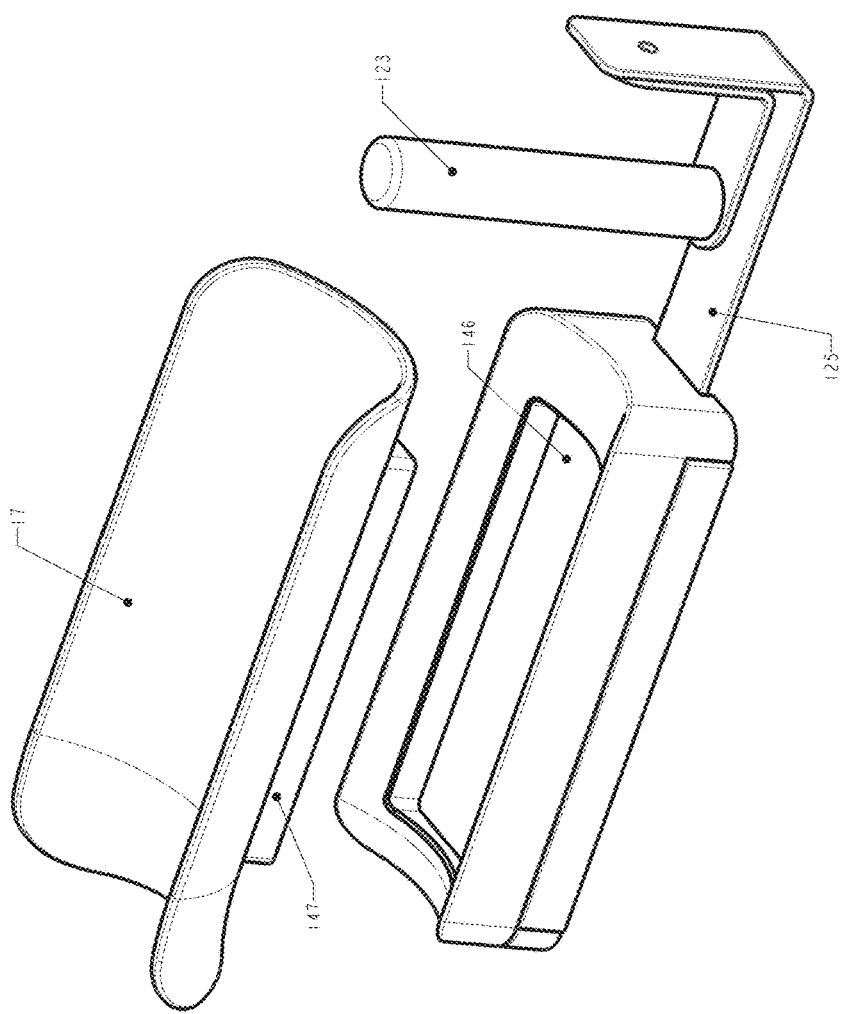
FIG. 19A is an embodiment of the Extremity Receiving Cuff of the Extremity Stabilization Apparatus illustrating the modularity of the Extremity Receiving Cuff.

FIG. 19A is an exploded or disassembled isometric view of the extremity receiving cuff 17 and the cuff receiving surface 146 of the Extremity Stabilization Apparatus 15. The plurality of surfaces defined by the female boundary of the cuff receiving surface 146 are oriented in such a way to allow for the male boundary of undercarriage of the extremity receiving cuff 17, referred to as the cuff alignment surface 147, to fit together in a modular fashion. FIG. 19B is a side and bottom view of the extremity receiving cuff 17, illustrating the shape of the protruding cuff alignment surface 146 that is designed to fit within a slightly larger female surface of exact shape referred to as the cuff receiving surface 146.

Figure 20:
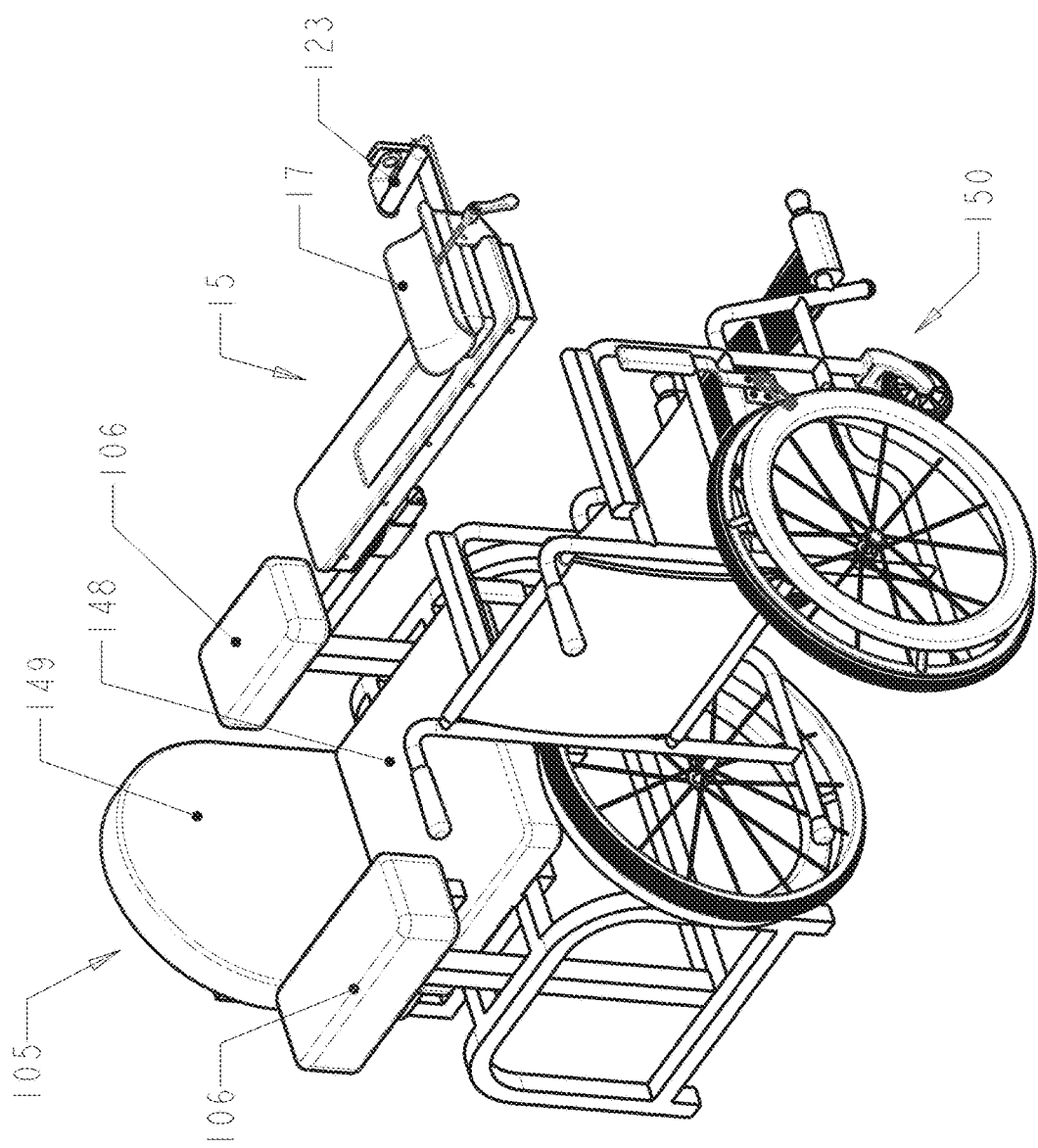
FIG. 20 is an isometric view illustrating an embodiment of the Extremity Stabilization Apparatus 15, wherein the crossbar member of the chair is rotatably coupled to the chair.

FIG. 20 is an isometric view illustrating the Extremity Stabilization Apparatus 15. A ninety degree angle of rotation between the chair arm 106 and the Extremity Stabilization Apparatus 15 is such that it allows for a wheelchair 150 to be positioned behind the rotating handle assembly 124. The relative position between the wheelchair 150 and the rotating handle assembly 124 is such that it allows the healthcare provider to perform venipuncture using the Extremity Stabilization Apparatus 15 on a patient disposed in a wheelchair 150.

Figure 21B:
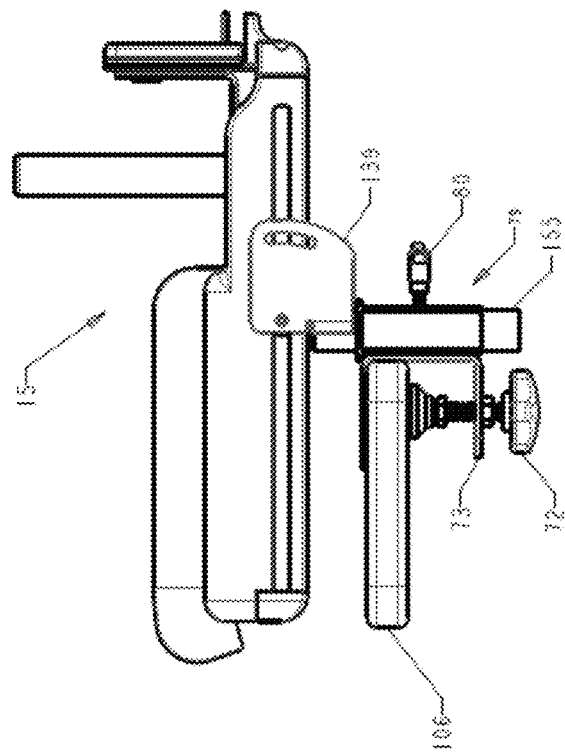
FIG. 21B is a side view of the embodiment shown in FIG. 21A.
Figure 21A:
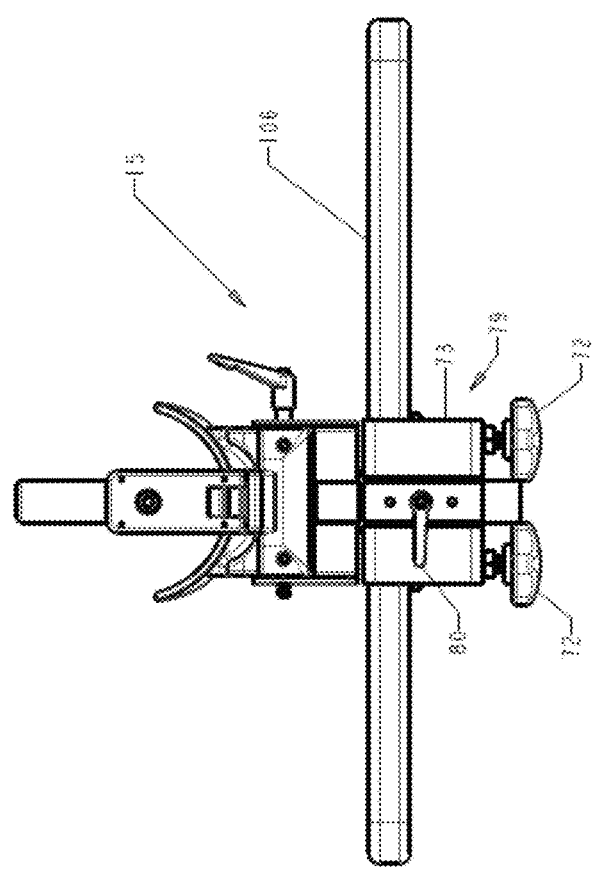
FIG. 21A is a front view of the Extremity Stabilization Apparatus rotatably coupled an embodiment of the modular clamp assembly shown in FIG. 6A, removably attached to a chair arm.

FIG. 21A is a front view of the Extremity Stabilization Apparatus 15 rotatably coupled an embodiment of the modular clamp assembly 79 shown in FIG. 6A, removably attached to a chair arm 106. In this embodiment, a rotating post 155 is fixedly attached to the extremity stabilization apparatus hinge 139 and rotatably coupled to the modular clamp assembly 79. FIG. 21B is a side view of the embodiment shown in FIG. 21A.

Figure 22B:
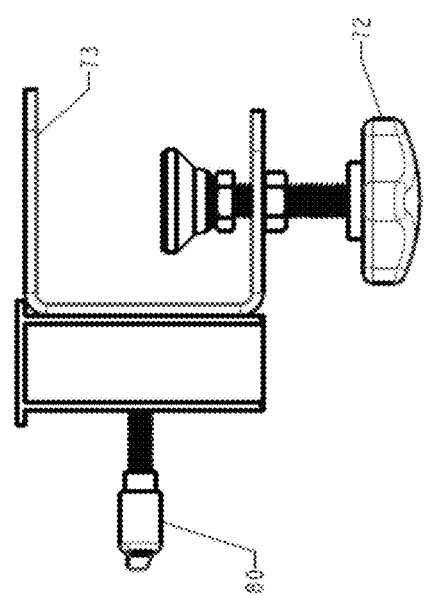
FIG. 22B is side view of an embodiment of the modular clamp assembly shown in FIGS. 21A and 21B.
Figure 22C:
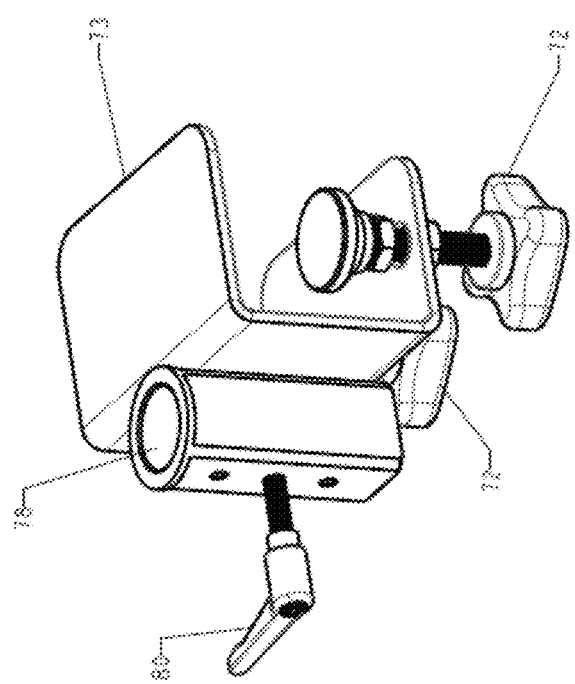
FIG. 22C is an isometric view of the modular clamp assembly shown in FIG. 22B.
Figure 22A:
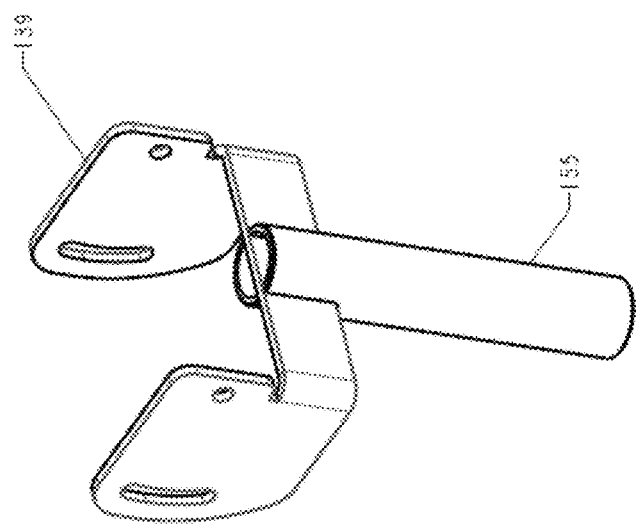
FIG. 22A is an isometric view of an embodiment of the extremity stabilization apparatus hinge fixedly attached to a rotating post.

FIG. 22A is an isometric view of an embodiment of the extremity stabilization apparatus hinge 139 shown in FIG. 18 that is fixedly attached to a rotating post 155 with the outside diameter of the rotating post 155 being smaller than the inside diameter of the female receiving cannula 78 of the modular clamp assembly 79 shown in FIG. 22B. In this embodiment, the second locking handle 80 is threadably coupled to the modular clamp assembly 79 such that the threaded end of the second locking handle 80 can advance into the diameter defined by the female receiving cannula 78 thereby locking the rotational position of the rotating post 155. The C-Shape of the modular clamp assembly shown in FIG. 22B fits around the surface of a medical chair, table, bed or the like. In this embodiment, threaded clamp handles 72 are threadably coupled to the modular clamp assembly 79. Advancement of the threaded clamp handles 72 increases the clamping force on the surface of a medical chair, table, bed or the like. FIG. 22C is an isometric view of the modular clamp assembly 79 shown in FIG. 22B.

Figure 23B:
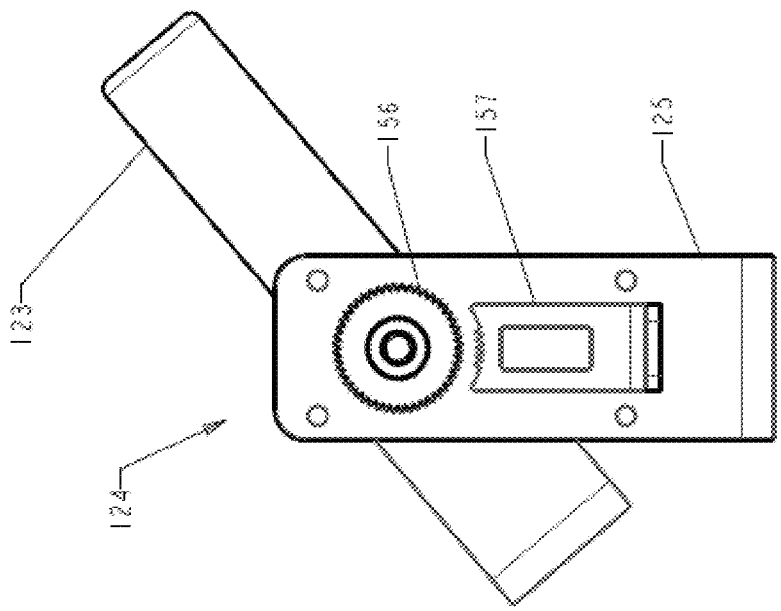
FIG. 23B is a front view of the embodiment shown in FIG. 23A.
Figure 23A:
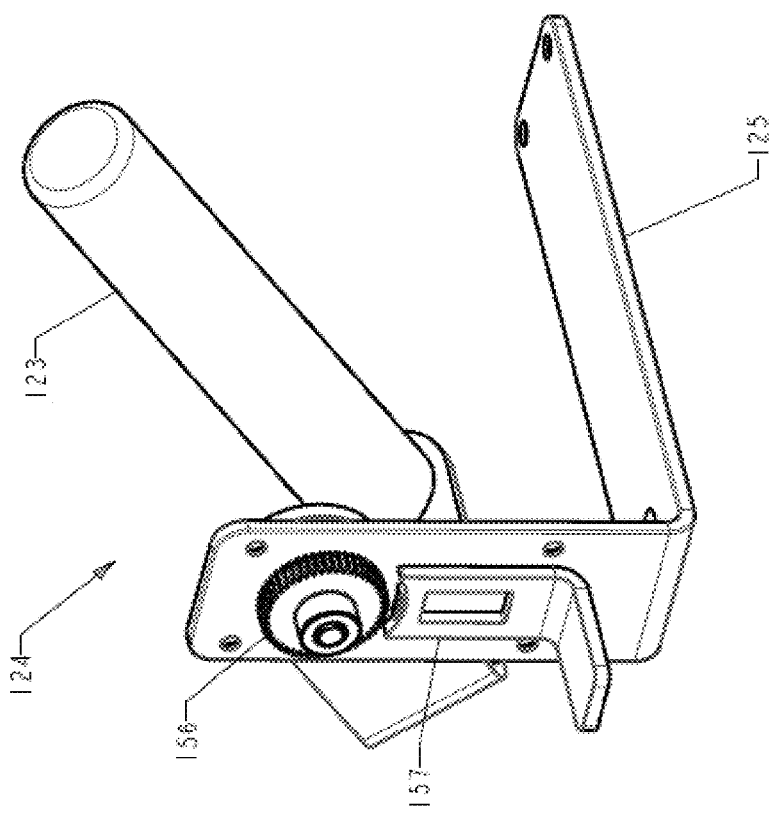
FIG. 23A is an isometric view of an embodiment the rotating handle assembly.

FIG. 23A is an isometric view of an embodiment the rotating handle assembly 124 shown in FIGS. 13A thru 13C. In this embodiment, the rotating handle 123 is both fixedly attached to a rotating handle gear 156 and rotatably coupled to the rotating handle linkage arm 125. Further in this embodiment, the geared tooth profile of the rotating handle gear 156 matches the geared tooth profile of the of the rotating handle pawl 157. Further in this embodiment, the rotating handle pawl 157 is slideably coupled to the rotating handle linkage arm 125 wherein the translation of the rotating handle pawl 157 away from the rotating handle gear 156 allows the rotating handle 123 to freely rotate. Conversely, meshing the rotating handle pawl 157 with the rotating handle gear 156, stops rotation of the rotating handle 123. FIG. 23B is a front view of the embodiment shown in FIG. 23A.

Figure 24:
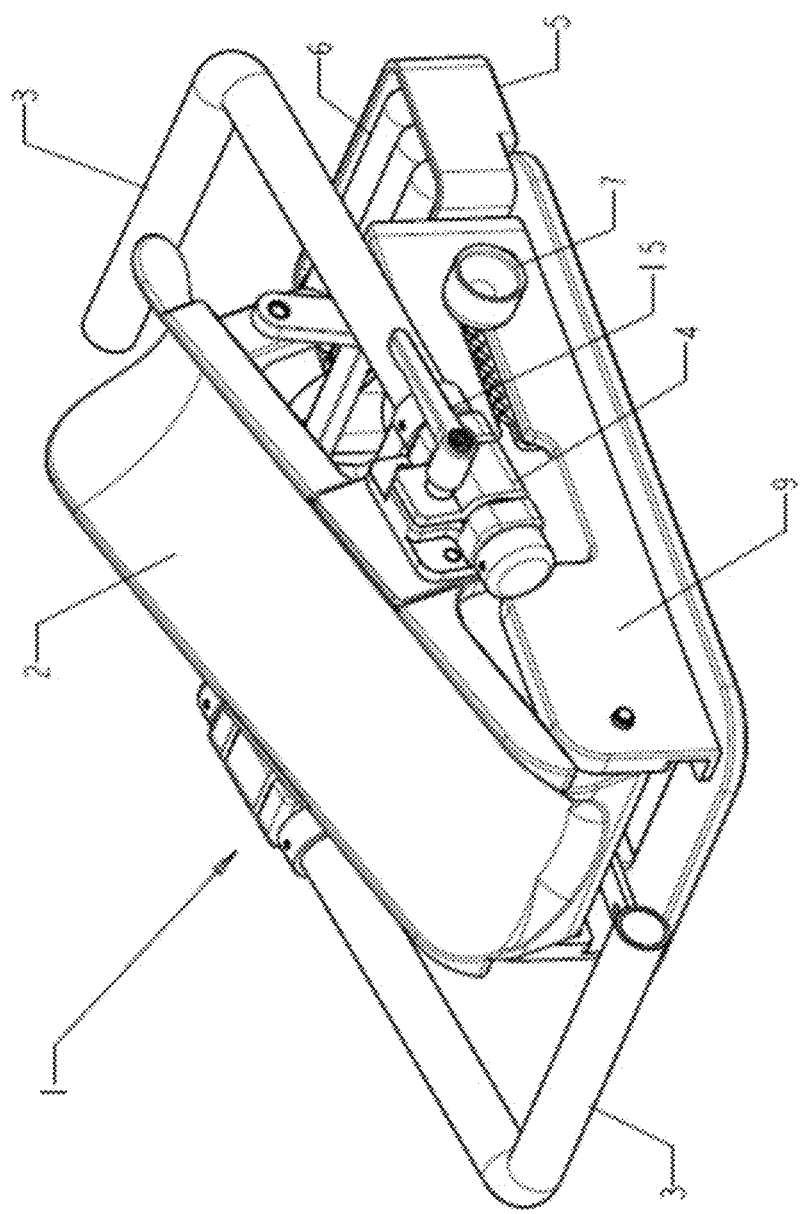
FIG. 24 is an isometric view of another embodiment of an apparatus configured to support a limb, sometimes referred to herein as the Mobile Extremity Stabilization Apparatus.

FIG. 24 is an isometric view of another embodiment of a Mobile Extremity Stabilization Apparatus.

Figure 25C:
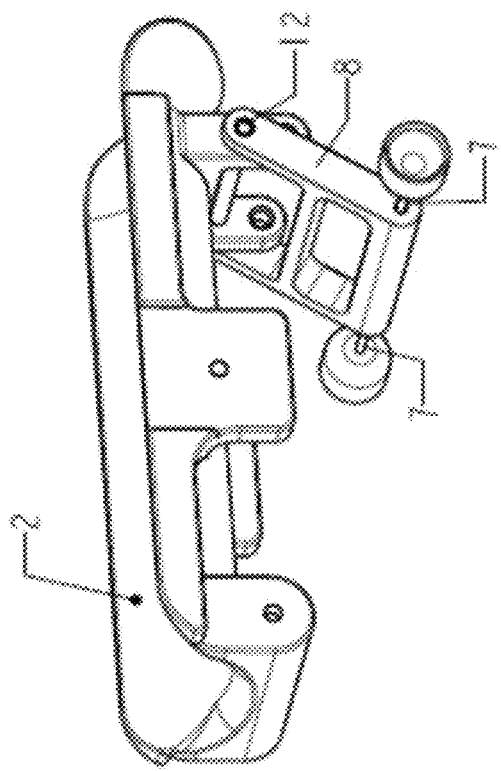
FIG. 25C is an isometric view of the extremity receiving cuff and cuff linkage assembly.
Figure 25A:
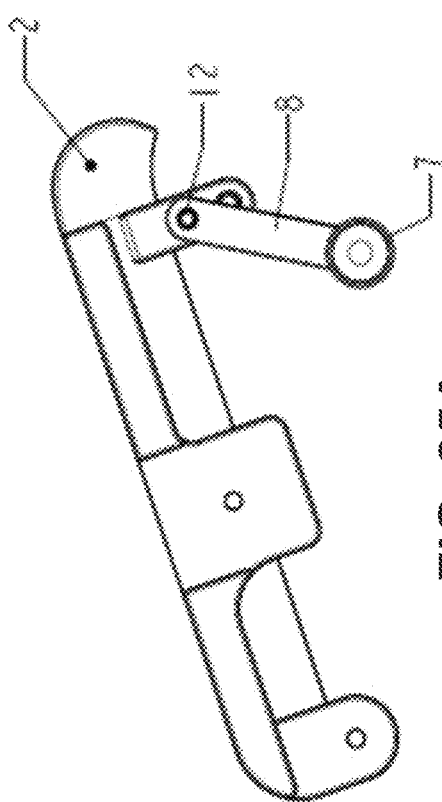
FIG. 25A is a side view of an embodiment of the extremity receiving cuff and cuff linkage assembly.
Figure 25B:
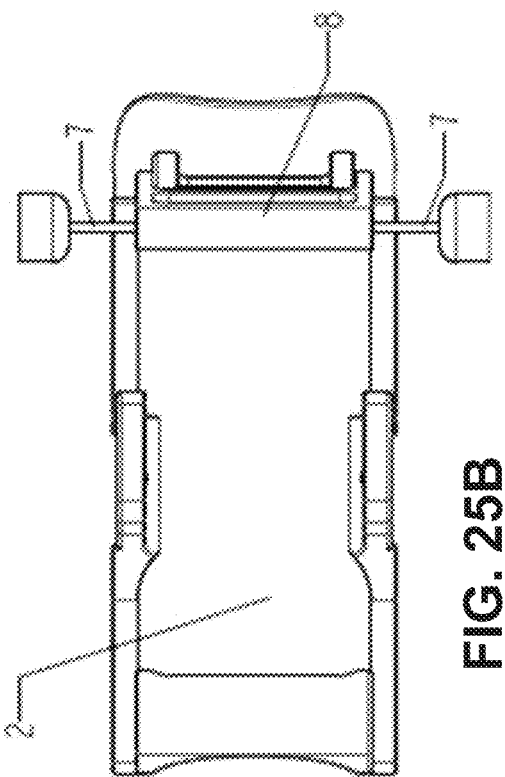
FIG. 25B is a bottom view of the extremity receiving cuff and cuff linkage assembly that operates to position the cuff at various angles relative to a surface supporting the apparatus.

FIG. 25A is a side view of the extremity receiving cuff 2, rotatably coupled to a cuff linkage 8. A solid round cuff linkage hinge pin 12 extends through a hollow bore on one end of the cuff linkage 8 and also through a second bore on one end of the extremity receiving cuff 2 forming the rotational coupling between both elements. A cuff linkage rack pin 7 is fixedly attached to the cuff linkage 8 at the opposite end relative to the hollow bore described above. In this embodiment, the cuff linkage rack pin 7 is fixedly attached on opposite sides of the cuff linkage 8. FIG. 25B is a bottom view of the embodiment shown in FIG. 25A. FIG. 25C is an isometric view of the embodiment shown in FIG. 24A.

FIG. 26A is a side view of the embodiment shown in FIG. 25A, rotatably coupled to the cuff base 9. A solid round cuff hinge pin 11 extends through a hollow bore one end of the cuff base 9 and also through a second bore on the extremity receiving cuff 2, on the side opposite the connection between the extremity receiving cuff 2 and the cuff linkage 8. In this preferred embodiment, the angle between the extremity receiving cuff 2 and the cuff base 9 can freely increase incrementally along a one directional ratchet defined by the gear rack 10. As the angle between the extremity receiving cuff 2 and the cuff base 9 increases, the rotatably coupled cuff linkage 8 translates along the surface defined by the ratchet teeth of the gear rack 10. In other embodiments, the extremity receiving cuff 2 and the cuff base are rotatably coupled without a cuff linkage 8. In other such embodiments, the rotation between the extremity receiving cuff 2 and the cuff base is controlled by clamping the two components together about their joined axis of rotation or through an internal ratcheting mechanism.

FIG. 26B is a side view of the embodiment shown in FIG. 26A whereby angle between extremity receiving cuff 2 and the cuff base 9 is less than that shown in FIG. 26A. As a result of the decrease in angle between the extremity receiving cuff 2 and the cuff base 9, the position of the cuff linkage rack pin 7 has changed. FIG. 26C is an isometric view of the embodiment shown in FIG. 26A.

Figure 27A:
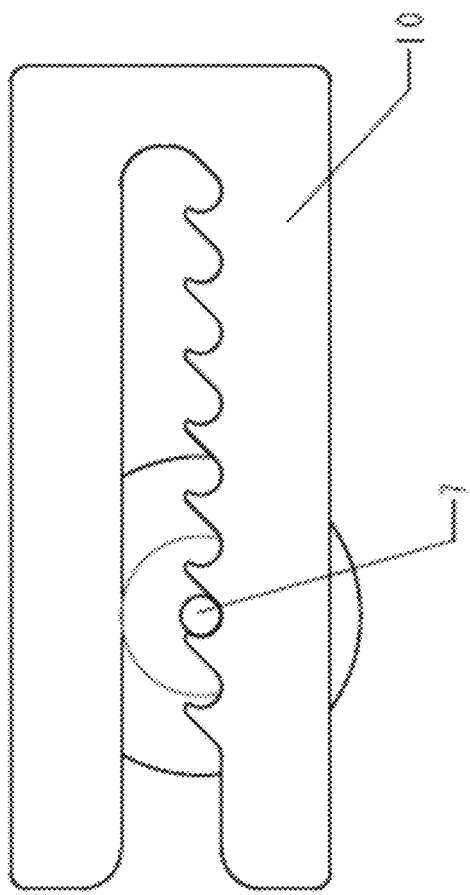
FIG. 27A is a side view of an embodiment of the cuff linkage rack pin and the gear rack.

FIG. 27A is a side view of the cuff linkage rack pin 7 and the gear rack 170. In this embodiment, the diameter of the protruding boss of the cuff linkage rack pin 7 shown in FIG. 25B is such that it is less than the profile of the tooth of the gear rack 10. In this embodiment, the cuff linkage rack pin 7 acts similar to a pawl against the gear teeth of the gear rack 10.

Figure 27B:
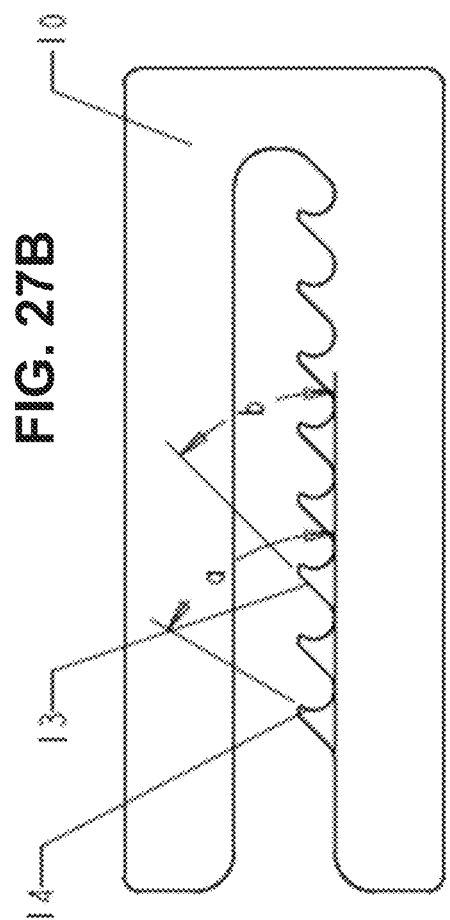
FIG. 27B is a side view of the gear rack shown in FIG. 27A.

FIG. 27B is a side view of the gear rack 10. The one directional ratchet of the gear rack 10 is defined by the gear rack leading surface 13 and the gear rack trailing surface 14. As the cuff linkage rack pin 7 moves along the surface of the gear rack 10 teeth, it contacts both the gear rack leading surface 13 and the gear rack trailing surface 14. In the embodiment shown the angle of the gear rack leading surface 13 is (a) and the angle of the gear rack trailing surface 14 is (b). Angle (a) is less than ninety degrees, therefore the cuff linkage rack pin 7 can freely translate along the gear rack leading surface 13. Angle (b) is also less than ninety degrees, therefore the cuff linkage rack pin 7 is held from translating in the reverse direction. The orientation of the gear rack leading surface 13, gear rack trailing surface 14 and the extremity receiving cuff 2 is such that increasing the angle between the extremity receiving cuff 2 and the cuff base 9 allows for free translation along the gear rack leading surface 13. In this embodiment, to decrease the angle between the extremity cuff 2 and the cuff base 9, the cuff linkage rack pin 7 is lifted away from the teeth of the gear rack 10.

FIG. 28A is a side view of the extremity receiving cuff 2 and the handle 3. In this embodiment, the handle 3 is rotatably coupled to the extremity receiving cuff 2 with rotation about an axis perpendicular to the side of the extremity receiving cuff 2. In this embodiment, the cylindrical handle 3 is disposed within the slightly larger inner bore of the rotating pole clamp 14 allowing the handle 3 to rotate about a second axis defined by the inner bore 17 of the rotating pole clamp 14. In the embodiment shown, the rotation of the handle 3 about both axes, defined above, is locked in place by the pole clamp handle 15. FIG. 28B is a side view of the embodiment shown in FIG. 28A whereby the handle has rotated relative to the embodiment in FIG. 28A, about the axis perpendicular to side of the extremity receiving cuff 2.

Figure 29C:
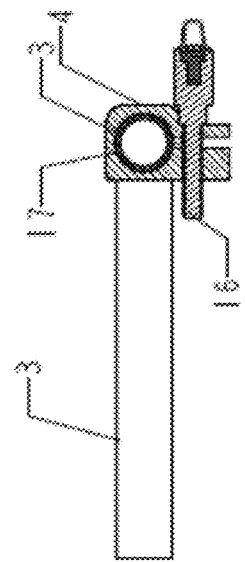
FIG. 29C is a side view of the cuff.
Figure 29D:
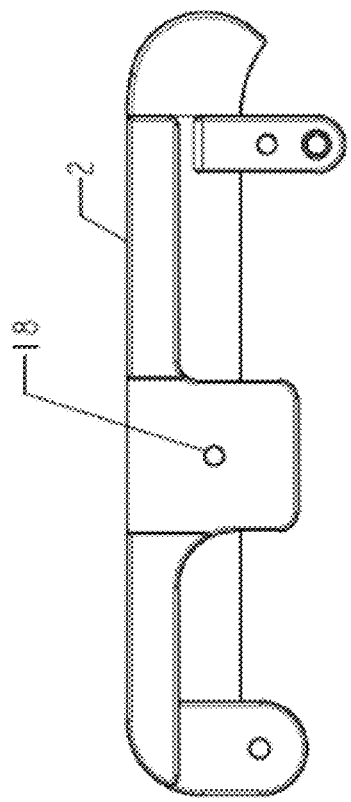
FIG. 29D is a sectional view of the embodiments shown in FIG. 28A.
Figure 29A:
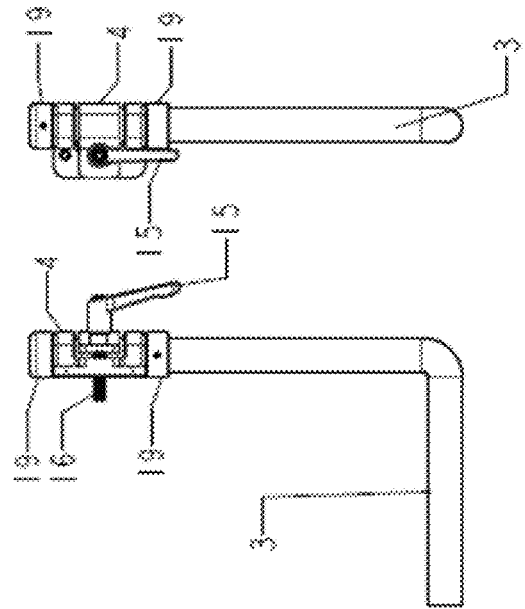
FIG. 29A is a top and side view of an embodiment of the handle and rotating pole clamp.

FIG. 29A is a top and side view of the handle 3 and rotating pole clamp 4 embodiment shown in FIGS. 28A and 28B. In this embodiment, the pole clamp handle 15 is comprised of a threaded tip 16 that extends through axis of rotation defined by the inner bore of the rotating pole clamp 4. In this embodiment, the rotating pole clamp 4 is a C-shaped clamp. The C-Shape of the inner bore of the rotating pole clamp 4, clamps down upon the cylindrical surface of the handle as the threaded tip 16 of the pole clamp handle 15 is advanced into the female receiving cuff threaded bore 18, shown in FIG. 29C. The clamping of the C-Shape inner bore of the rotating pole clamp 4, restricts the rotation of the handle 3 about the axis defined by the inner bore of the rotating pole clamp 4. Also shown in this embodiment are the two pole rings 19 on opposite ends of the rotating pole clamp 4. The pole rings 19 are rigidly attached to the handle 3 with an outer diameter greater than that of the diameter defined by the inner bore of the rotating pole clamp 4. The pole ring(s) 19 restrict the linear motion along the axis defined by the inner bore of the rotating pole clamp 4, without restricting the rotation of the handle 3 about the axis defined by the inner bore of the rotating pole clamp 4.

Figure 29B:
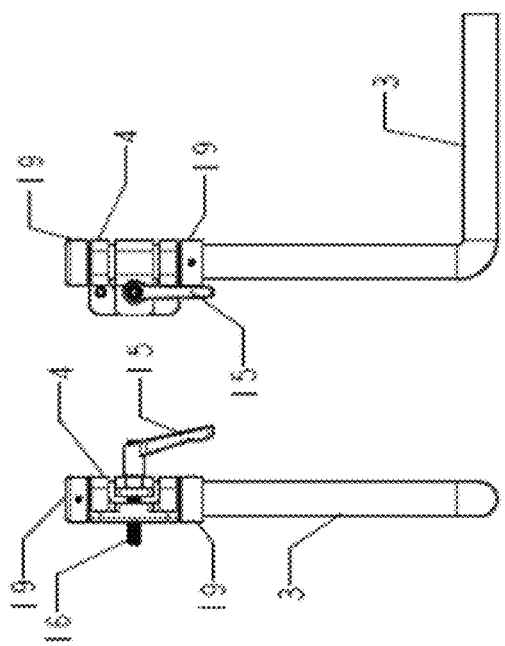
FIG. 29B is a top and side view of the embodiment shown in FIG. 29A with the handle rotated relative to the rotating pole clamp.

FIG. 29B is a top and side view of the embodiment shown in FIG. 29A whereby the handle 3 has rotated relative to the embodiment shown in 29A, about the axis defined by the inner bore of the rotating pole clamp 4. FIG. 29C is a side view of the extremity receiving cuff 2. In this embodiment the cuff threaded bore 18 is shown. As the threaded tip 16 of the pole clamp handle 15 advances into the cuff threaded bore 18, the rotating pole clamp 4 compresses against the side of the extremity receiving cuff 2 thereby restricting the rotation of the handle 3 about the axis defined by side perpendicular to the extremity receiving cuff 2. Simultaneously, as the threaded tip 16 of the pole clamp handle 15 advances into the cuff threaded bore 18, the inner bore of the rotating pole clamp 4 clamps down upon the cylindrically shaped handle 3. FIG. 29D is a sectional view of the embodiment shown in FIG. 28A. In this view the inner bore of the rotating pole clamp 4 is shown and referred to as the pole clamp bore 17.

FIG. 30A is a side view of an embodiment of the Mobile Extremity Stabilization Apparatus 1. In this embodiment, a locking pin 20 is inserted through the cuff base 9 and the cuff linkage 8 thereby restricting any rotation between the extremity receiving cuff 2 and the cuff base 9. FIG. 30B is a sectional front view of the embodiment shown in FIG. 30A. FIG. 30C is a side view of the embodiment shown in FIG. 30A whereby the extremity receiving cuff 2 has rotated relative to the cuff base 9. The locking pin 20 is inserted through first a cuff base receiving bore 22 then through the cuff receiving bore 21 only when the extremity receiving cuff 2 is rotated relative to the cuff base 9 such that both the cuff base receiving bore 22 and the cuff receiving bore 21 are axially aligned. FIG. 30D is a side view of the locking pin 20. In this embodiment the locking pin 20 is cylindrical in shape and has a diameter less than the diameter of the cuff receiving bore 21 and the cuff base receiving bore 22.

FIG. 31 is an isometric view of the Mobile Extremity Stabilization Apparatus 161 removably attached to a removable stand 23.

FIG. 32A is a side view of an embodiment the Mobile Extremity Stabilization Apparatus 1. In this embodiment, the rotation between the extremity receiving cuff 2 and the cuff base 9 is controlled by a pressurized cylinder 24 containing an internal cylinder piston 28. The internal cylinder piston 28 translates along the axis defined by the pressurized cylinder 24. The pressurized cylinder 24 is rotatably coupled to the cuff base 9 about the cuff base hinge 26. The internal cylinder piston 28 is rotatably coupled to the extremity receiving cuff 2 about the extremity receiving cuff hinge 25. The pressurized cylinder release handle 27 controls the relative translation between the internal cylinder piston 28 and the pressurized cylinder 24 whereby the relative translation results in increasing and decreasing angles formed between the extremity receiving cuff 2 and the cuff base 9. FIG. 32B is a bottom view of the embodiment shown in FIG. 32A.

FIG. 33A is an isometric view of the removable container 5 and the extremity receiving cuff 2. In this embodiment, the removable container 5 is removably attached to the handle 3, which is rotatably coupled to the extremity receiving cuff 2. In this embodiment, a cuff attachment tube 29 is fixedly attached to the extremity receiving cuff 2 opposite the side of the handle 163. The outer diameter of the handle 3 and the cuff attachment tube 29 are the same, allowing the removable container 5 to be removably attached to either the cuff attachment tube 29 or the handle 3. FIG. 33B is a detailed side view of the removable container 5, removably attached to the cuff attachment tube 29. In this view the connection between the removable container 5 and the cuff attachment tube 29 is secured by the removable container clip 20 whereby the inner diameter defined by the removable container clip 20 is less than the outer diameter of the handle 3 or cuff attachment tube 29. In this embodiment the material of construction of the removable container is such that the removable container clip 20 can elastically deflect about the outer diameter of the cuff attachment tube 29 or the handle 3 to allow the removable container 5 to be secured to the cuff attachment tube 29 or handle 3.

Figure 34:
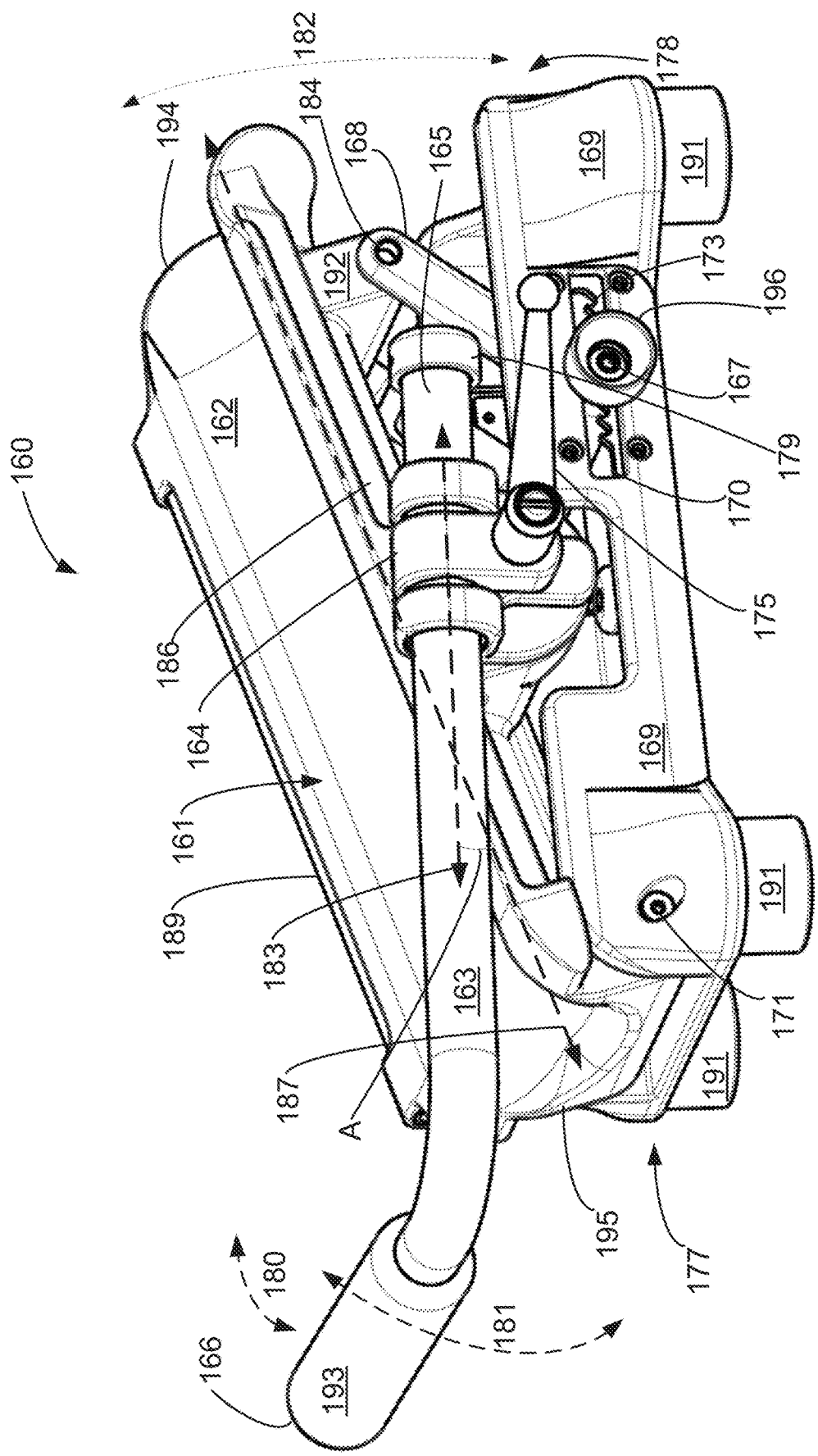
FIG. 34 is a perspective view of another embodiment of an apparatus for stabilizing an extremity.

FIG. 34 is a perspective view of another embodiment of an apparatus 160 for stabilizing an extremity. In this example, the apparatus 160 includes a cuff 162 coupled to a base 169 with means to raise and lower an elevating end 194 of the cuff 162 at the back 178 of the base 169. The cuff 162 includes a cuff surface 161 that supports a limb placed thereon, that is, the limb is to be supported is placed on cuff surface 161. The cuff 162 has a longitudinal axis 187 that runs from the front 177 of the cuff 162 to the back 178 of the cuff 162. The cuff 162 also includes a cuff base 186 coupled to the side of the cuff 162 opposite of the cuff surface 161, the cuff base including structure that supports the cuff 162 moves correspondingly with the cuff 162 (e.g., when the cuff is elevated). The elevating end 194 of the cuff 162 may be raised and lowered vertically (e.g., relative to the orientation of the figure) along the directional arrow 182. The cuff 162 may be elevated and held in an elevated position using an elevation assembly. In this example, the elevation assembly includes the positioning member 196, a bracket 192 coupled to the cuff 162 and extending from the underside of the cuff 162, cuff linkage 168 pivotally couple to the bracket 192 and coupled to the positioning mechanism 196, and gear rack 170 on which the positioning mechanism 190 may be moved and held at a certain place by teeth 173 to position the cuff 162 at a certain elevation angle. The cuff 162 is also coupled to the base 169 at a rotational end 195 at the front 177 of the base 169 by a cuff hinge pin 171, which extends through a portion of the base 169 and the cuff 162, and allows the rotating end 195 of the cuff to rotate around the cuff hinge pin 171. A plurality of feet 191 are attached to the bottom of the base 169.

The apparatus 160 also includes a handle 163 coupled to a portion of the cuff 162 (e.g., the cuff base 186) and configured to move in conjunction with the cuff 162, as the cuff 162 is raised and lowered. The handle 163 may have a circular cross-section, as shown here, or may be shaped differently, e.g., have other cross-sectional shapes. A circular cross-section is advantageous for allowing the rotation of the handle 163 in clamp 164. The handle 163 may include a grip 193 at the distal end 166 of the handle 163. The grip 193 may surround a portion of the handle 163. In some embodiments, the grip 193 fits over a portion of the handle 163, e.g., at the distal and of the handle 163. The grip 193 may be formed from a rigid material, or from a material that may be slightly deformed under the application of force, e.g., a patient's hand squeezing the grip 193, such that the grip 193 is comfortable for a patient to grasp. In some examples, the grip 193 may be formed from the same material as the handle 163 and not be a separate component of the handle 163. That is, the grip may be the portion of the handle 163 that is at the front end 177 of the apparatus that is configured to receive a patient's hand when the patient's forearm is supported by the cuff 162.

The handle 163 is coupled to the cuff 162 via the clamp 164, which in this example is attached to the cuff base 186, such that the clamp 164 moves with the elevating end 194 of the cuff 162 is moved away from the base 169. The clamp 164 is configured to tighten around the handle 163 using clamp handle 175 to hold the handle 163 in a desired position. In some embodiments, a pole ring 179 is arranged on the proximal end 165 of the handle 163. The pole ring 179 has a larger diameter than the handle 163, preventing the distal end of the handle 163 from passing through the clamp 164.

The handle 163 and correspondingly the grip 193 coupled to the apparatus in a configuration to move in three different directions to allow fitting to any size patient in any position. First, the handle 163 moves through the clamp 163 along a longitudinal direction 183 when the clamp 164 is loosened (e.g., by turning handle 175 in a counter-clockwise direction) such that the grip 193 may be positioned at varying distances relative to the cuff 162. Second, the handle 163 may move along directional curve 181 when the clamp 164 is loosened, the directional curve 181 being in a generally vertical plane with respect to the orientation of FIG. 34 such that the handle 163 can be vertically raised and lowered. Finally, handle 163 may move along the directional curve 180 when the clamp 164 is loosened, such that the distal end 166 of the handle 163 can be rotated (e.g., around a handle longitudinal axis 183) to be placed in a horizontal or vertical position, or any position in-between on either side of a vertical position, or be rotated past a horizontal position to any position. Then the longitudinal axis 183 of the handle 163 is aligned parallel with the longitudinal axis 187 of the cuff, the grip 193 may be rotated in a plane that is normal to, or substantially normal to, the longitudinal axis 187. When the handle 193 is moved along directional curve 181 such that the longitudinal axis 183 is at an angle A with the longitudinal axis 187 and rotated around longitudinal axis 183, the rotation of the grip 193 is in a plane that is at the angle A to the longitudinal axis 187. This allows, for example, the same apparatus to be easily used for holding a left arm or the right arm of a patient, contacting the arm at two places, the forearm (by the cuff) and the hand (by the grip/handle).

In this embodiment, the cuff 162 is coupled to the base 169 at the elevating end 194 via a cuff linkage 168 and a bracket 192, connected to form hinge 184. The cuff linkage 168 is coupled to the positioning member 196 by a cuff linkage pin 167. The positioning member 196 is configured to move forward towards the front 177 of the apparatus and backwards towards the back 178 of the apparatus by lifting the positioning member 196 to disengage it from the teeth 173, and moving it in the desired direction to elevate the cuff 162 (e.g., backward) or to lower the cuff 162 (e.g., forward). The cuff linkage 168 may be positioned along the gear rack 170, the teeth 173 of the gear rack 170 holding the positioning member 196 in one of a plurality of positions, these structures being similar to corresponding components in the embodiments illustrated in FIGS. 24-27. In some embodiments, and as further described in reference to FIG. 35, the apparatus includes an attachment pole 189. In some embodiments, the attachment pole 189 is disposed on the opposite side of the cuff 162 as the clamp 164. The attachment pole 189 may be used to attach a container to, for example, container 5 illustrated in FIG. 33A.

In an example of operation, an arm of a patient is placed in the cuff 162, resting on the surface of the cuff 161. The patient's hand grasps the grip 193. The position of the grip 193 and the handle 163 may be moved along the directional arrows 180, 181, 183 to place the arm and secure the arm in a preferred position for the particular task being performed (e.g., taking a blood sample. The clamp 164 is operationally functional to allow the positioning of the grip 193 and the handle 163 and lock the desired position in place. The cuff 162 may also be raised along directional arrow 182 to provide the desired incline of the arm for the task. Once the apparatus is adjusted, so long as the patient rests their arm on the cuff 162 and holds the grip 192, the position of the arm is maintained.

Figure 35:
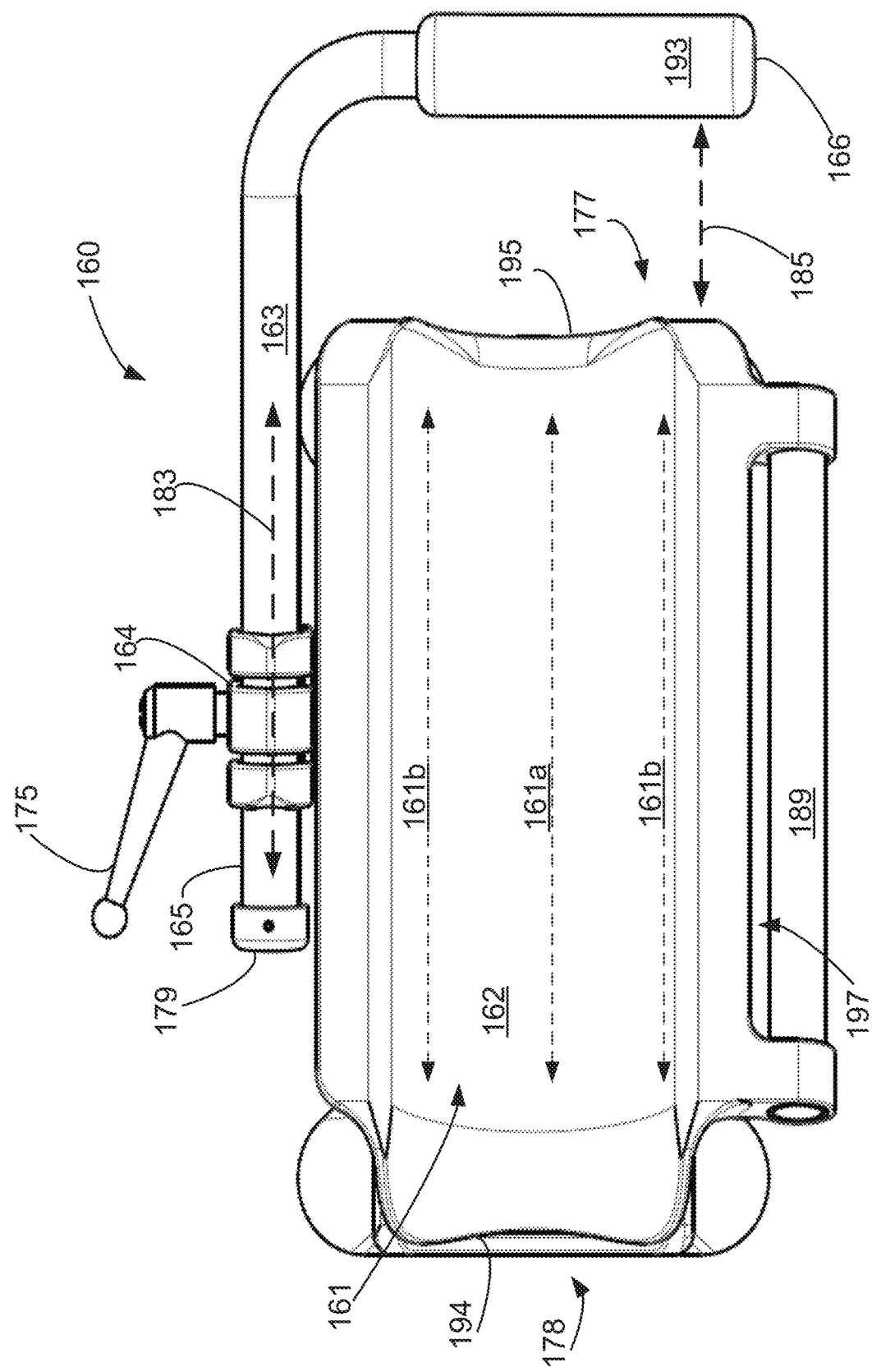
FIG. 35 is a top plan view of the apparatus of FIG. 34.

FIG. 35 is a top plan view of the apparatus 160 of FIG. 34. In this view, the cuff attachment pole 189 is illustrated as running along a portion of the side of the cuff 162, and offset from the cuff 162 by an aperture 197 that separates the pole 189 from the cuff 162. The aperture 197 allows a container 5 (FIG. 33A) to be attached to the pole 189, attachment structure of the container 5 fitting around the pole 189 and at least partially in the aperture 197.

In some examples, the cuff surface 161 of this embodiment, and of the other embodiments described herein, may have a curved cross-sectional shape (e.g., sometimes referred to as being c-shaped or u-shape). For example, the cuff surface 161 may be lower in a middle portion 161a and higher on the sides 161b, such that an extremity placed onto the cuff surface 161 is more securely held in place and it contacts a larger portion of the cuff surface 161 than if the cuff surface 161 was flat. The cuff surface 161 may be formed of a rigid non-porous material (e.g., plastic, metal, composite) for durability and ease of cleaning. In some embodiments, the cuff surface 161 is formed of a deformable material (e.g., foam covered by vinyl) to increase patient comfort during use.

The handle 163 can be moved along the directional line 183 to position the grip 193 at varying distances 185 from the front 177 of the apparatus 160 to accommodate patients of different sizes.

Figure 36:
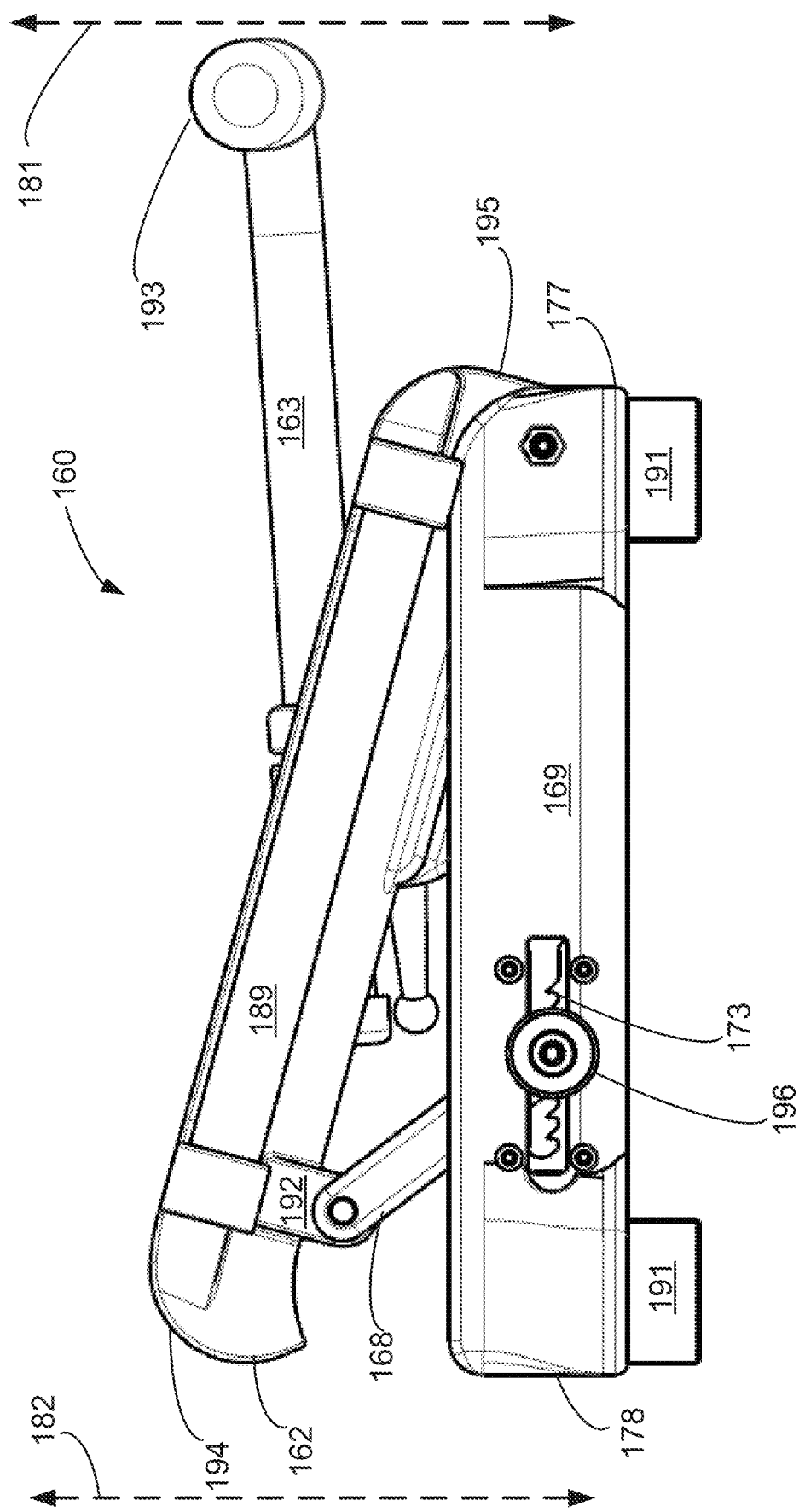
FIG. 36 is a right side elevation view of the apparatus of FIG. 34.

FIG. 36 is a right side elevation view of the embodiment of the apparatus 160 illustrated in FIG. 34. This view illustrates that the handle 163 and the grip 193 can be raised and lowered vertically 181 (relative to the orientation of the apparatus as illustrated) as one of the positioning options for the handle 163 and grip 193. This view also illustrates that the elevating end 194 of the cuff 162 can be raised and lowered vertically 182, e.g., by moving the positioning member 196 to engage different gear teeth 173. A set of the gear teeth 173 are attached on both sides of the base 169. As illustrated in FIGS. 34 and 36, the positioning member 193 extends across the base 169 such that it can be operated from either side of the base 169 to raise and lower the cuff 162.

Figure 37:
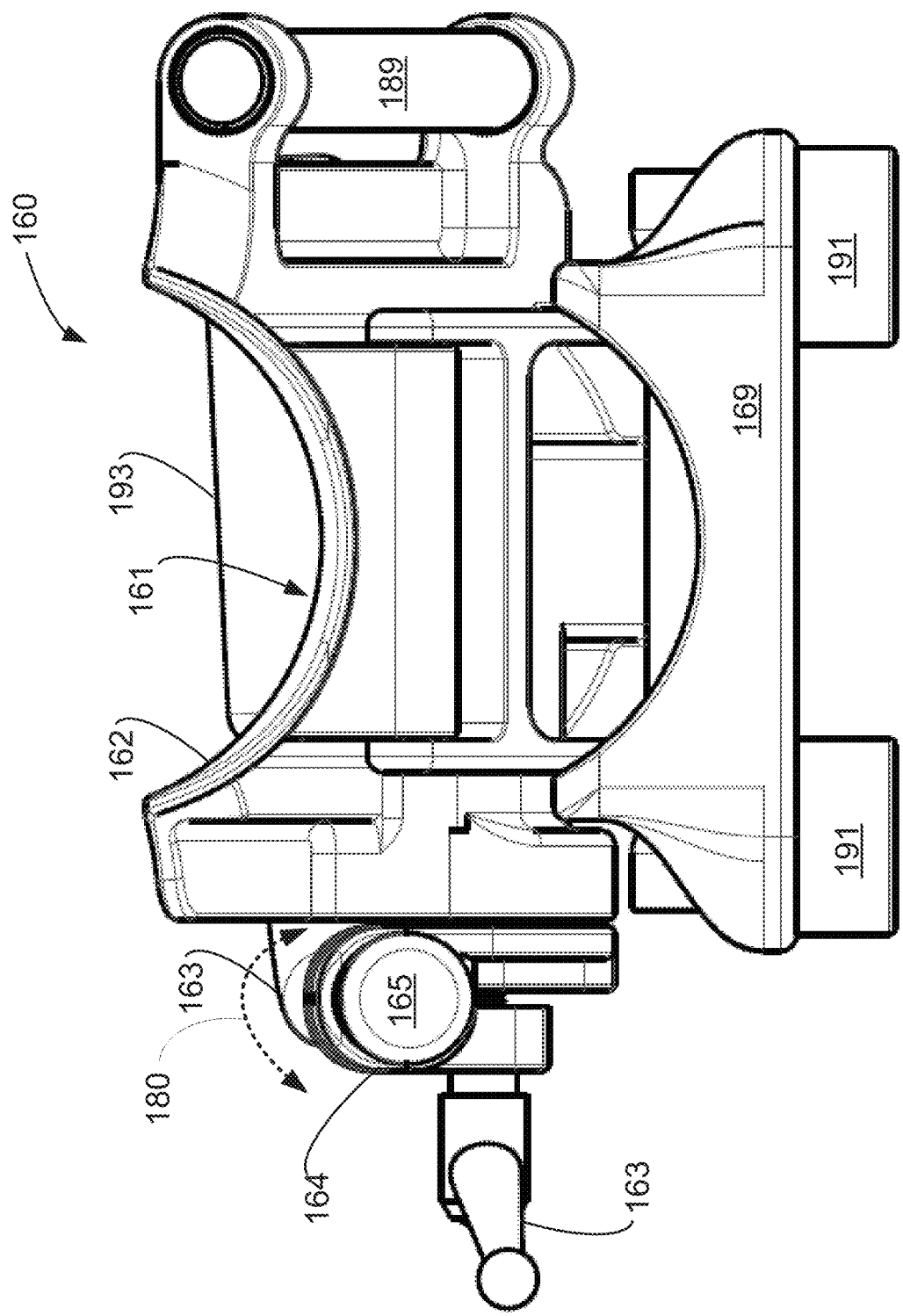
FIG. 37 is a back elevation view of the apparatus of FIG. 34.

FIG. 37 is a back elevation view of the apparatus of FIG. 34, showing the base 169 supported by the feet 191 which are arranged at opposite sides of the base 169. The u-shaped curve of the cuff surface 161 can also be seen in this view. FIG. 37 also illustrates one of the positional aspects of the handle 163. As illustrated in FIG. 37, the handle 163 extends through the pole clamp 164, the end 165 of the handle 163 being visible from this back elevation view. The pole clamp 164 and the handle 163 are configured such that the handle 163 can rotate in the direction of the motion arrow 180, that is, around the longitudinal axis 183 of the handle 163 going through the pole clamp 164, when the pole clamp 164 is sufficiently open to allow such rotation. When the grip 193 is positioned as desired for a particular patient, the handle 163 of the pole clamp 164 can be turned to tighten the pole clamp around the handle 163 and hold it in the desired position.

Figure 38:
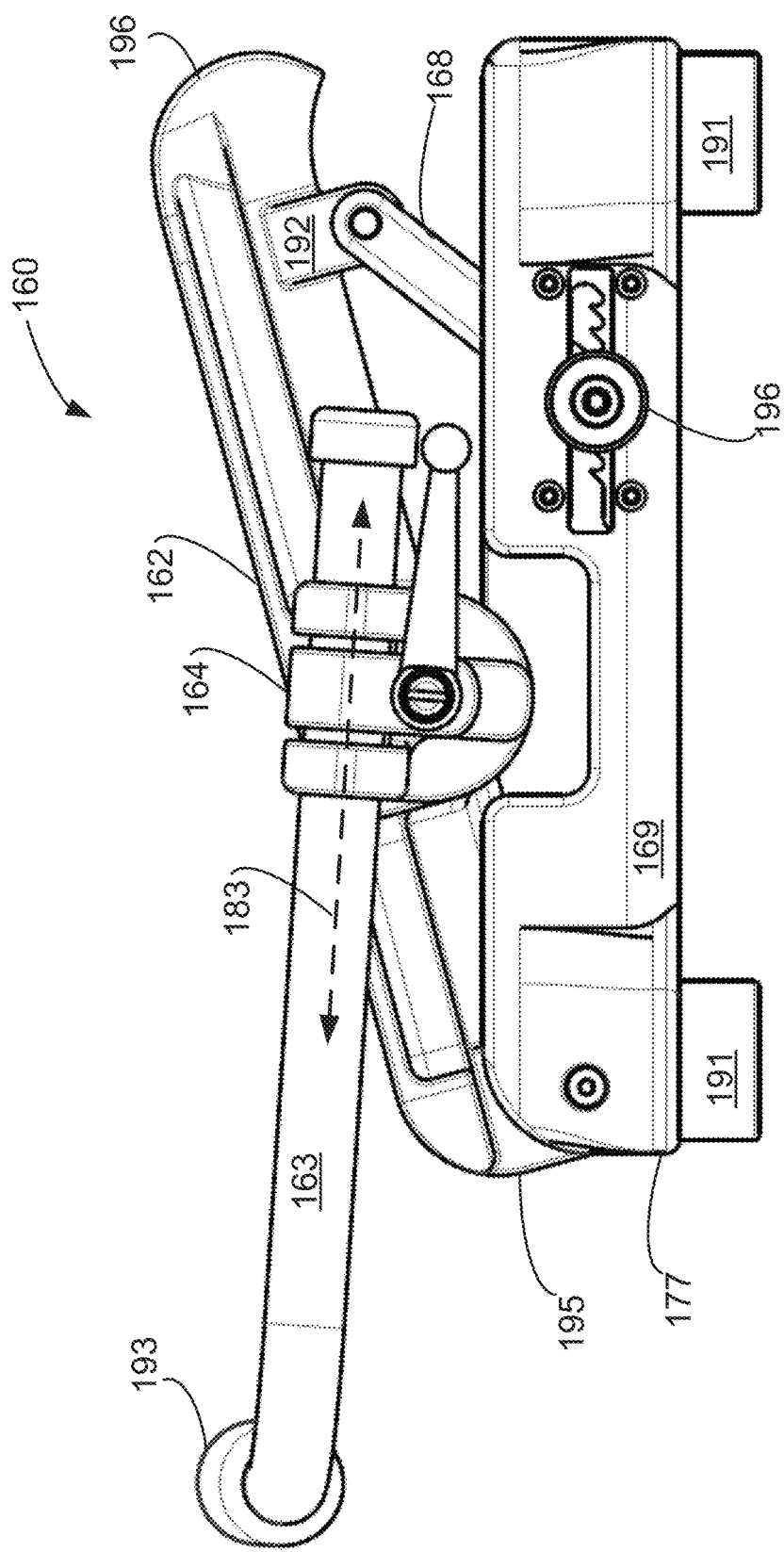
FIG. 38 is a left side elevation view of the apparatus of FIG. 34.

FIG. 38 is a left side elevation view of the apparatus 160 of FIG. 34, illustrating another aspect of the components described above.

Figure 39:
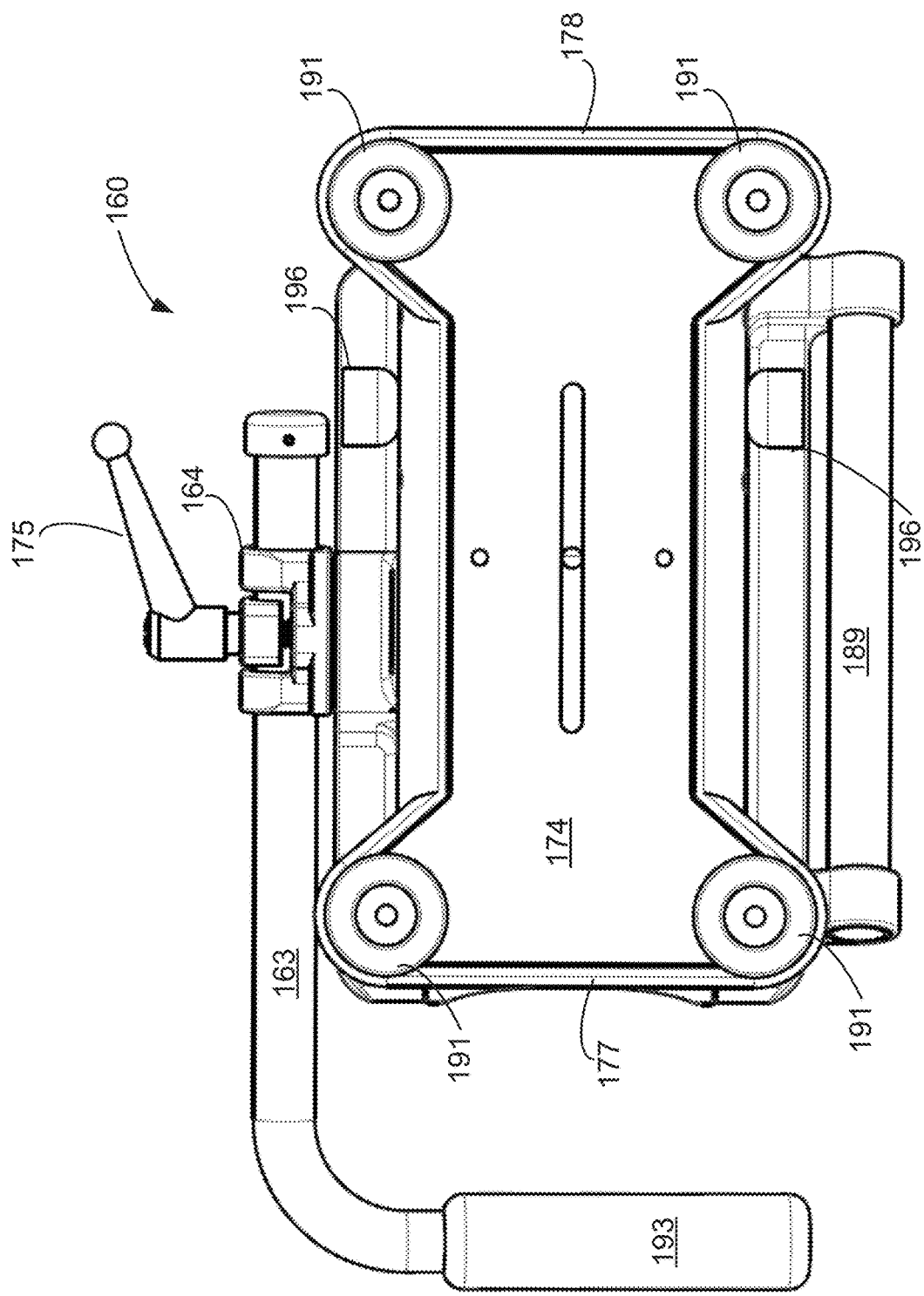
FIG. 39 is a bottom elevation view of the apparatus of FIG. 34.

FIG. 39 is a bottom elevation view of the apparatus 160 of FIG. 34. This view shows a bottom surface 174 of the lower portion of the base 169, and the four feet 191 arranged on the corners of the bottom surface 174. FIG. 39 also further illustrates the handle clamp 164, which can tighten around the handle 163 with the clamp handle 175 is tightened (e.g., rotated in a clockwise direction) forcing surfaces of the clamp to tightly press against the handle 163.

Figure 40:
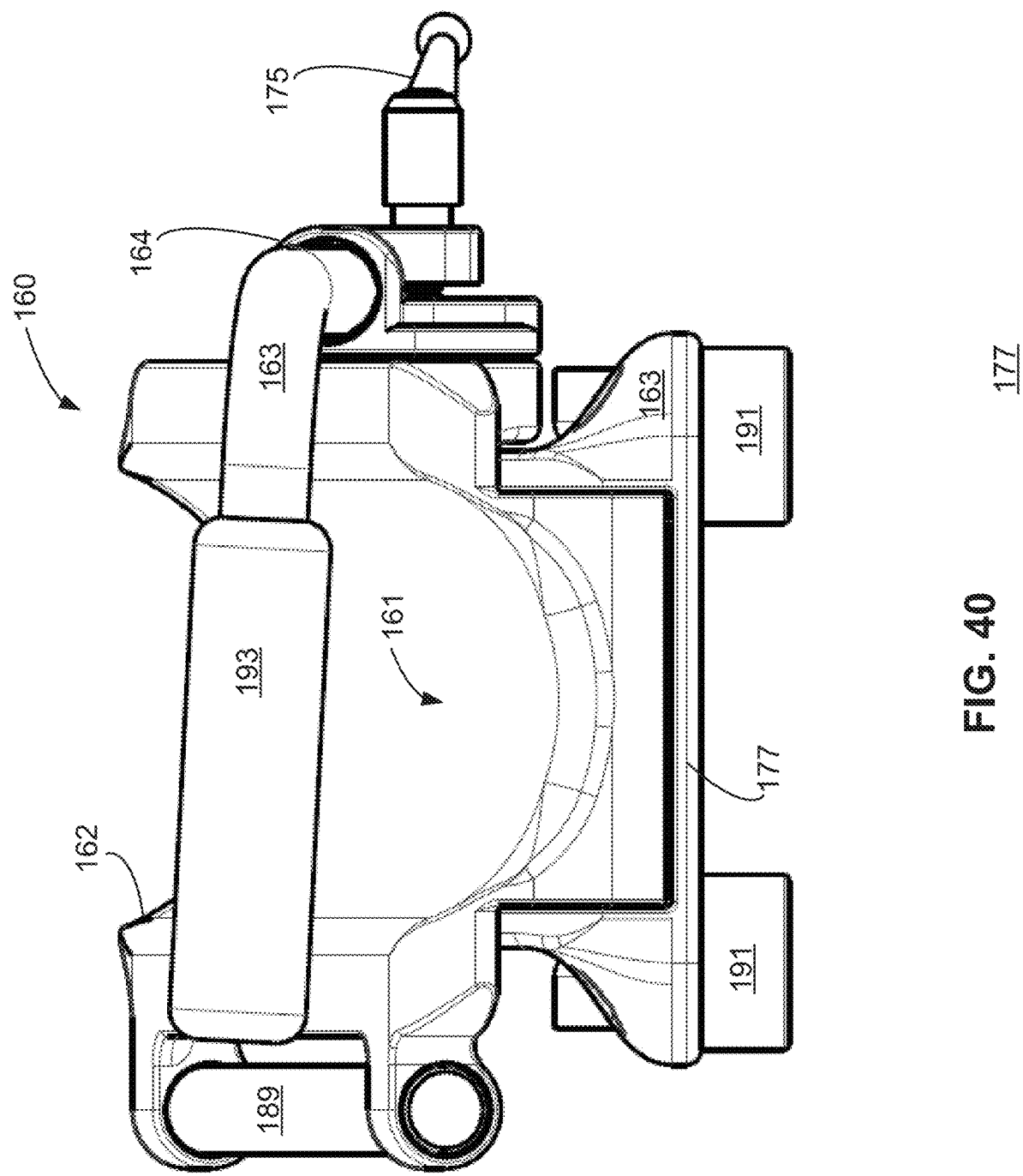
FIG. 40 is a front elevation view of the apparatus of FIG. 34.

FIG. 40 is a front elevation view of the apparatus 160 of FIG. 34, further illustrating the aspects of the apparatus 160 described above.

Figure 41:
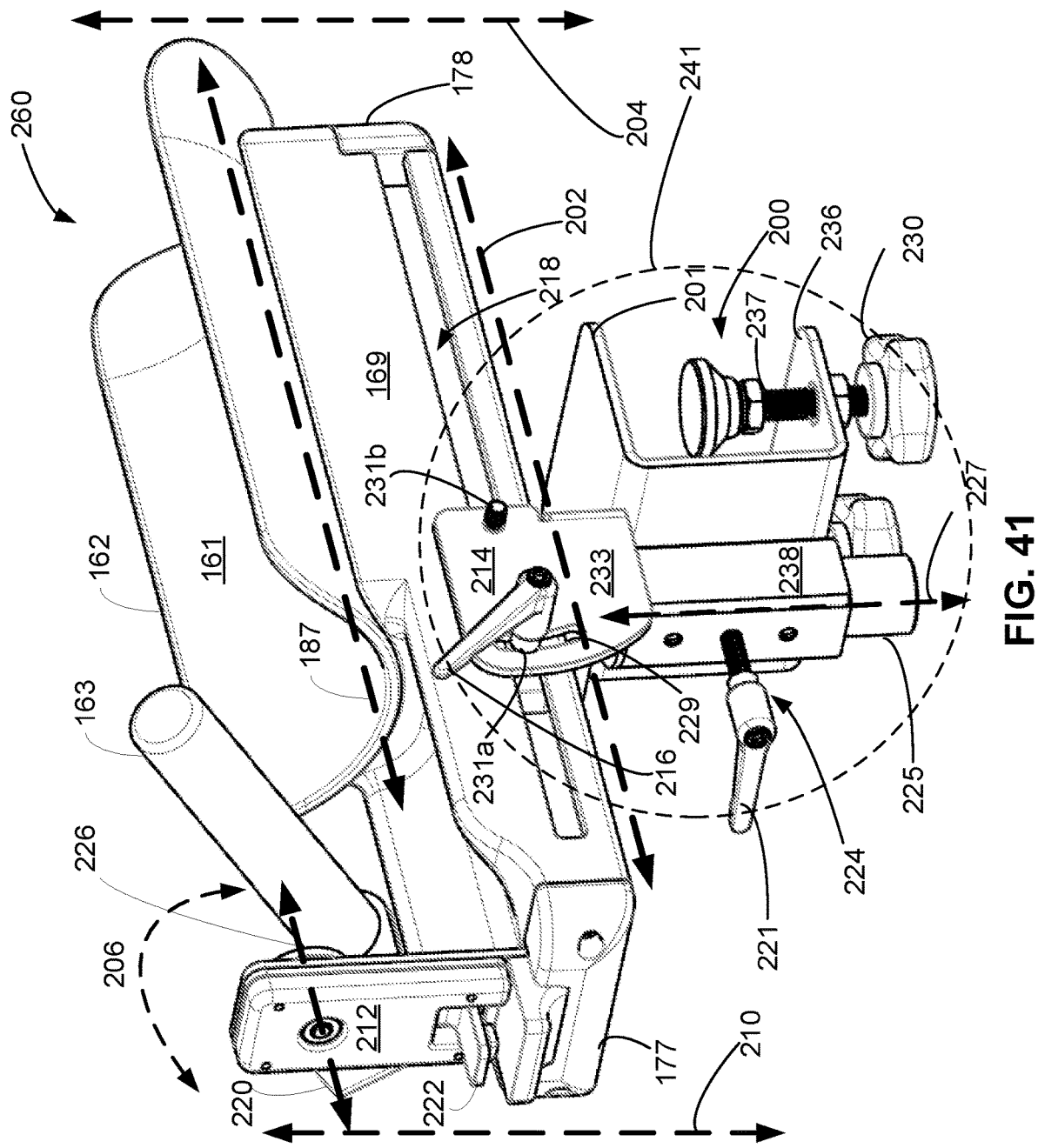
FIG. 41 is a perspective view of another embodiment of an apparatus for stabilizing an extremity which has certain similar components as the apparatus shown in FIGS. 21A and 21B.

FIG. 41 is a perspective view of another embodiment of an apparatus 260 for stabilizing an extremity. The apparatus 260 includes many of the same or similar features as the other embodiments illustrated herein (e.g., FIGS. 13-23) and that operate to provide structural support for a patient's forearm a hand, in many different positions, to securely hold the patient's arm for a variety of procedures.

In this example, apparatus 260 also includes an extremity support cuff 162 attached to a cuff base 169. The cuff 162 includes a cuff top surface 161 that may be curved as described for apparatus 160, or flat in other configurations. The cuff 162 has a front 177 and a back 178, and a longitudinal axis 187 that extends from the front 177 to the back 178 of the cuff 162. The cuff base 169 has a front 177 and a back 178. The cuff base 169 is coupled at the front 177 a rotational mechanism 212, which is coupled to a handle 163 via an L-shaped bracket 220. The rotational mechanism 212 extends from the base 169 on the same side of the base 169 as the cuff 162, such that the handle 163 is positioned in front of the cuff 162 between the rotational mechanism 212 and the cuff 162. The rotational mechanism 222 includes a lever 222 that when actuated allows the bracket 220 and the handle 163 to rotate in the direction 206 around an axis 226 running through the rotational mechanism 212, such that the handle 163 may be aligned to receive the hand of a patient when the forearm of the patient is placed in the cuff 162, in any desired position. Further description of an example of such a rotational mechanism is explained in reference to FIGS. 23A and 23B.

Still referring to FIG. 41, the apparatus 260 can be attached to various structure (e.g., a bed, a chair, a table etc.) using one or more clamping assemblies. For example, apparatus 260 includes a horizontal clamp assembly 200 and a vertical clamp assembly 224 attached to the horizontal clamp 200. The horizontal clamp assembly 200 (which also may be referred to as fixture clamp 200) is used, for example, to attach the apparatus 260 to a horizontal structure (e.g., a table, a chair). The clamp assembly 200 includes an upper clamp surface 201 and a lower clamp surface 236 through which movable clamping members 237 extend. The movable clamping members 237 are moved by rotating handles 230. The clamp assembly 200 can be, for example, similar to the clamp assembly illustrated in FIGS. 22B and 22C. A member 225 having a longitudinal axis 227, coupled to the base clamp assembly 214, extends from the base clamp assembly 214 and fits into a hole of a receiver 238 of the vertical clamp assembly 224. A mechanism of this type is further illustrated in FIG. 22C, which shows the hole 78 of a vertical clamp assembly. The member 225 and base clamp assembly 214 may be structured, and operate, similar to the rotating post 155 and the apparatus hinge 139 illustrated in FIG. 22A. The apparatus 260 may be rotated in the vertical clamp assembly 224 around the longitudinal axis 227 when placing the apparatus 260 in position for use. Also, the member 225 may be moved in the vertical clamp assembly 224 such that the apparatus 260 moves vertically along motion arrow 204, and can be secured at a desired position by tightening the vertical clamp assembly 224 using handle-221.

The apparatus 260 also includes an elevation assembly that allows the cuff 162 to be positioned at various angles and linear positions with respect to structure the apparatus 260 is attached to (e.g., via clamp assembly 200). In this example, the elevation assembly includes slot apertures 218 which are disposed in the based 169 and run nearly the length of the base 169 on both sides of the base 169 (e.g., FIG. 43). The elevation assembly also includes the base clamp assembly 214 having slot engaging members 231a, 231b that extend through the slot apertures 218. The slot aperture 218 and the slot engaging members 231a, 231b allow the base 169 to be moved to different positions along motion arrow 202, and secured at a desired position with the base clamp assembly 214. The base clamp assembly 214 includes a slot 229 in a side plate 233, the slot 229 having engaging member 231a running through the slot 229 (as well as running through the slot apertures 218). When the base clamp assembly 214 is loosened using handle 216, the front of the apparatus 260 can be moved up or down along motion arrow 210, and the back 178 of the apparatus 260 to be correspondingly moved along motion arrow 204 (in the opposite direction from the front 177), the slot engaging member 231a moving along the slot 229 while the slot engaging member 231b continues to engage the slot aperture 218, thus allowing the cuff 162 to be positioned at different angles, and then the handle 216 is used to tighten the clamp assembly 214.

In the configuration illustrated in FIG. 41, the apparatus 260 may be secured to a supporting structure by a clamp assembly 241 comprising clamp assembly 214, the pole clamp 224 and the clamp assembly 200. That is, the clamping structures 214, 224, and 200 may be referred to collectively as a clamping assembly 241. The base 169 is coupled to the clamping assembly 241 such that the cuff 162 and can be moved rotationally (e.g., around axis 227), longitudinally (e.g., translated along axis 202) and angled (e.g., the front 177 and back 178 of the cuff 162 in the respective directions 210 and 204) relative to the clamping assembly 241. For example, when the clamping assembly 241 is secured to a structure (e.g., a bed, table, chair, etc.) the cuff 162 can be rotated, translated and angled relative to the clamping assembly 241.

Figure 42:
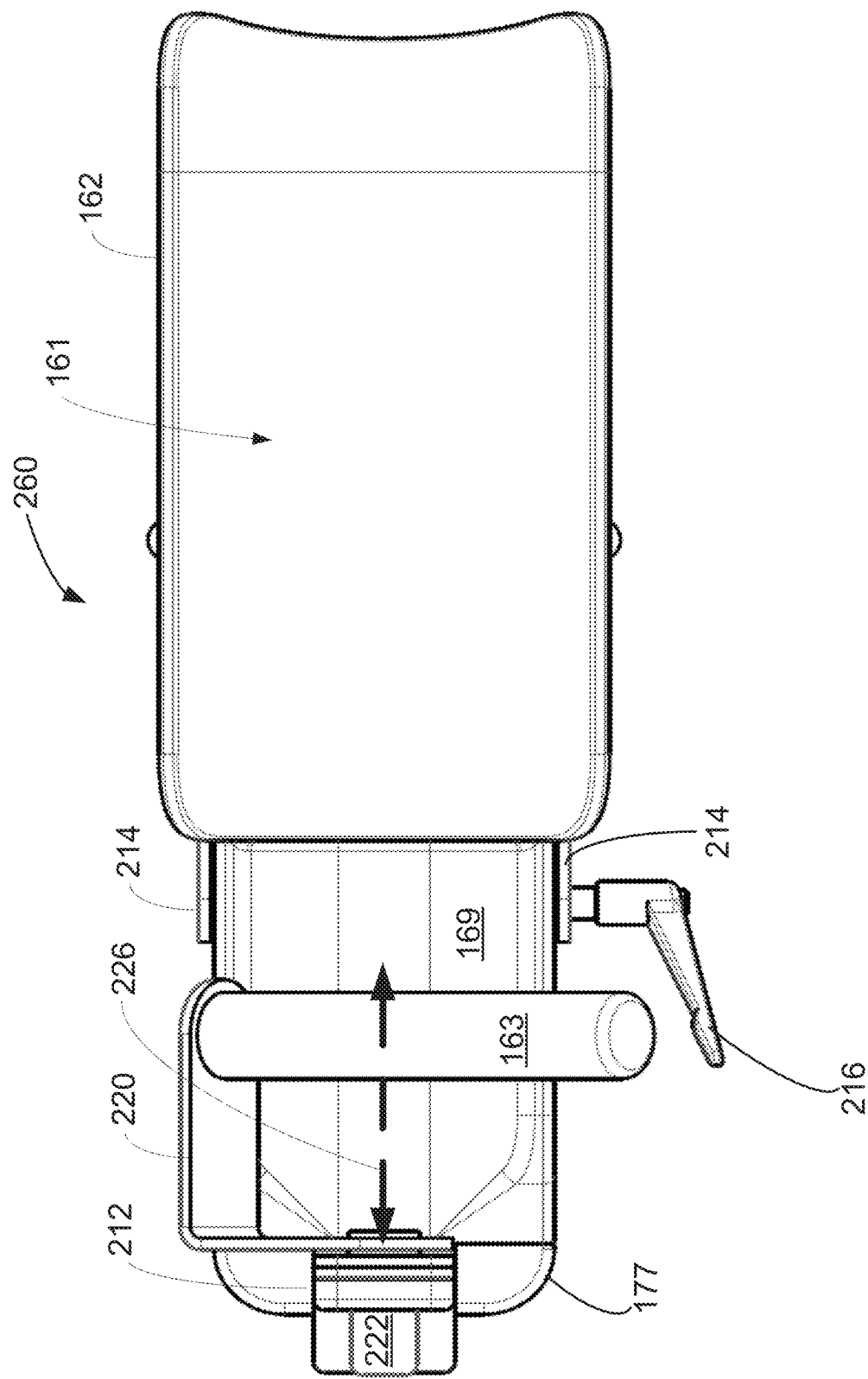
FIG. 42 is a top plan view of the apparatus of FIG. 41.

FIG. 42 is a top plan view of the apparatus 260 of FIG. 41. This view illustrates the L-shaped bracket 220 coupling the handle 163 to the rotational mechanism 212. The handle 163 extends from a portion of the bracket 220, aligned in a direction, for example, perpendicular to the axis 226 at a location between the rotational mechanism 212 and the cuff 162. As described in FIG. 41, the bracket 220 and the handle 163 are rotatable by the rotational mechanism 212 around the axis 226. The handle 163 may also be referred to as a grip, as it is configured to receive a hand of a patient whose forearm is placed in the cuff 162.

Figure 43:
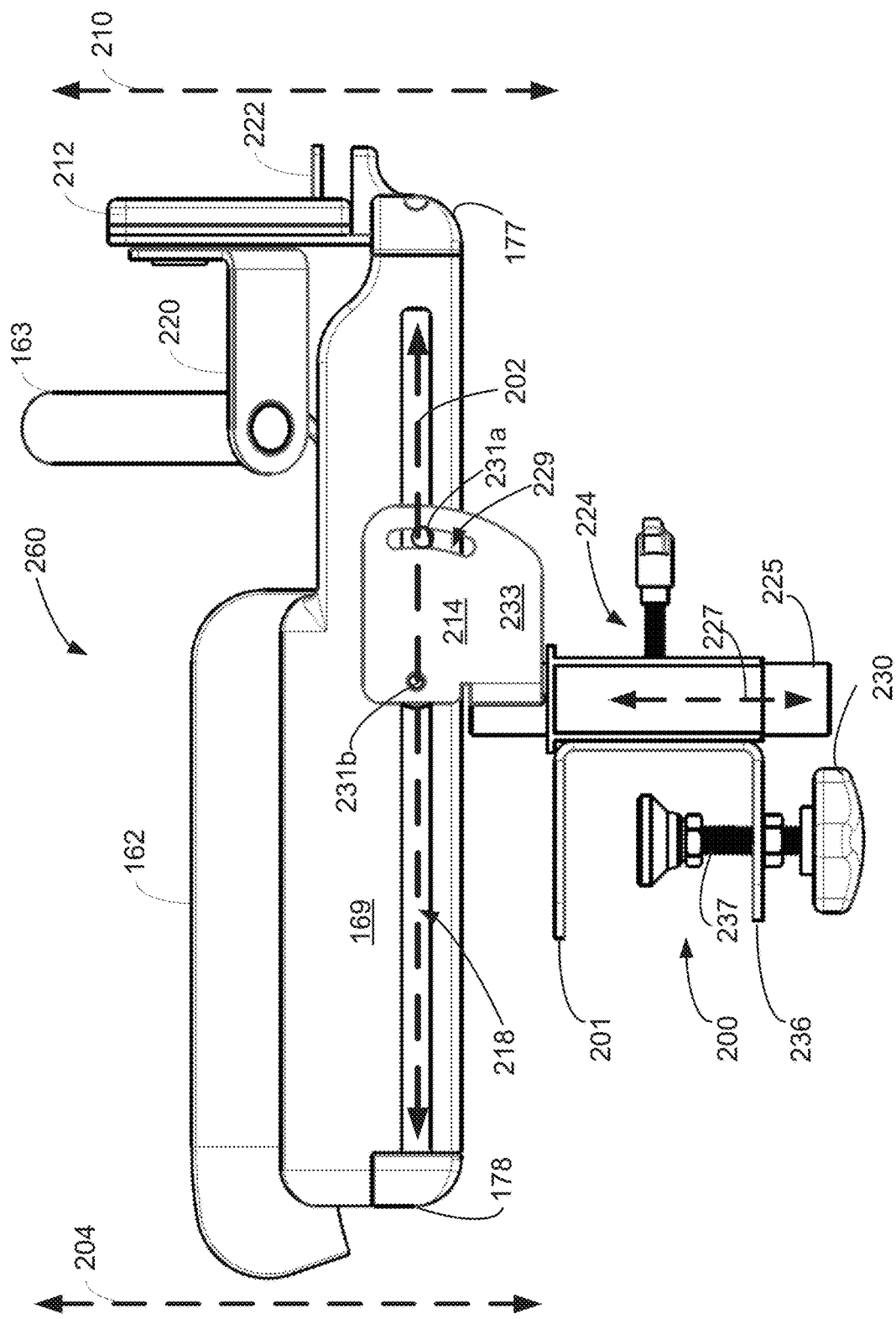
FIG. 43 is a right side elevation view of the apparatus of FIG. 41.

FIG. 43 is a right side elevation view of the apparatus of FIG. 41. In this view, the right side of base clamp assembly 214 is shown also having a slot 229 in which slot engaging member 231a moves when the front 177 of the apparatus 260 is moved up or down, e.g., in the direction if the motion arrow 210, and the back of the apparatus 178 is moved up and down 204 along motion arrow 204, to position the cuff 162 at different angles. This view also illustrates how the base 169 of the apparatus 260 can be moved along the motion vector 202, e.g., relative to the clamp assembly 214 when the clamp assembly 214 is secured in the clamp 224, which is secured to a structure (e.g., a table or chair) by the horizontal clamp assembly 200. The clamp assembly 214 can be rotated around longitudinal axis 227, correspondingly rotating the cuff 162 and the handle 163 around the longitudinal axis 227.

Figure 44:
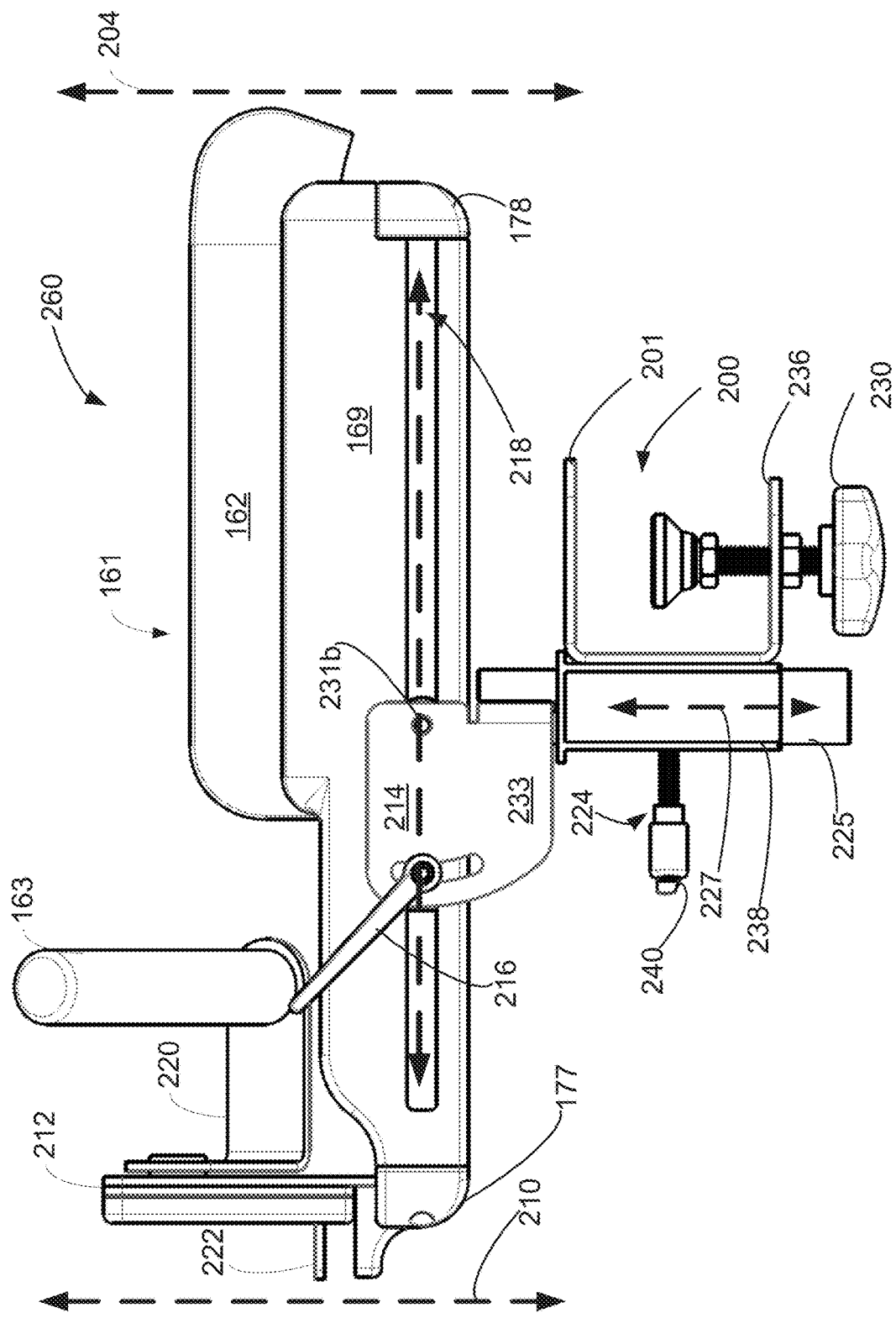
FIG. 44 is a left side elevation view of the apparatus of FIG. 41.

FIG. 44 is a left side elevation view of the apparatus 260 of FIG. 41, further illustrating components of the apparatus 260.

Figure 45:
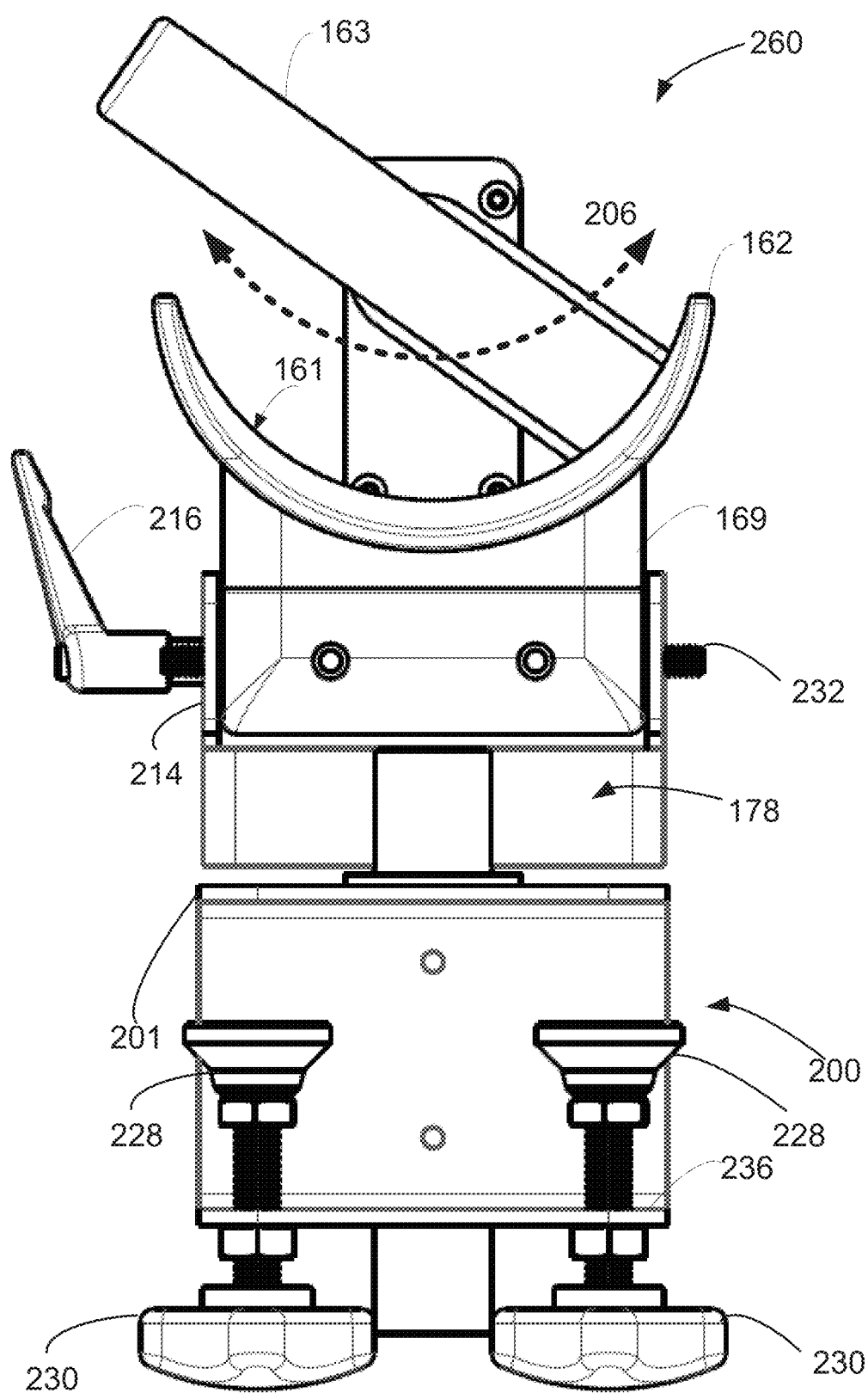
FIG. 45 is a back elevation view of the apparatus of FIG. 41.

FIG. 45 is a back elevation view of the apparatus 260 of FIG. 41, further illustrating components described above.

Figure 46:
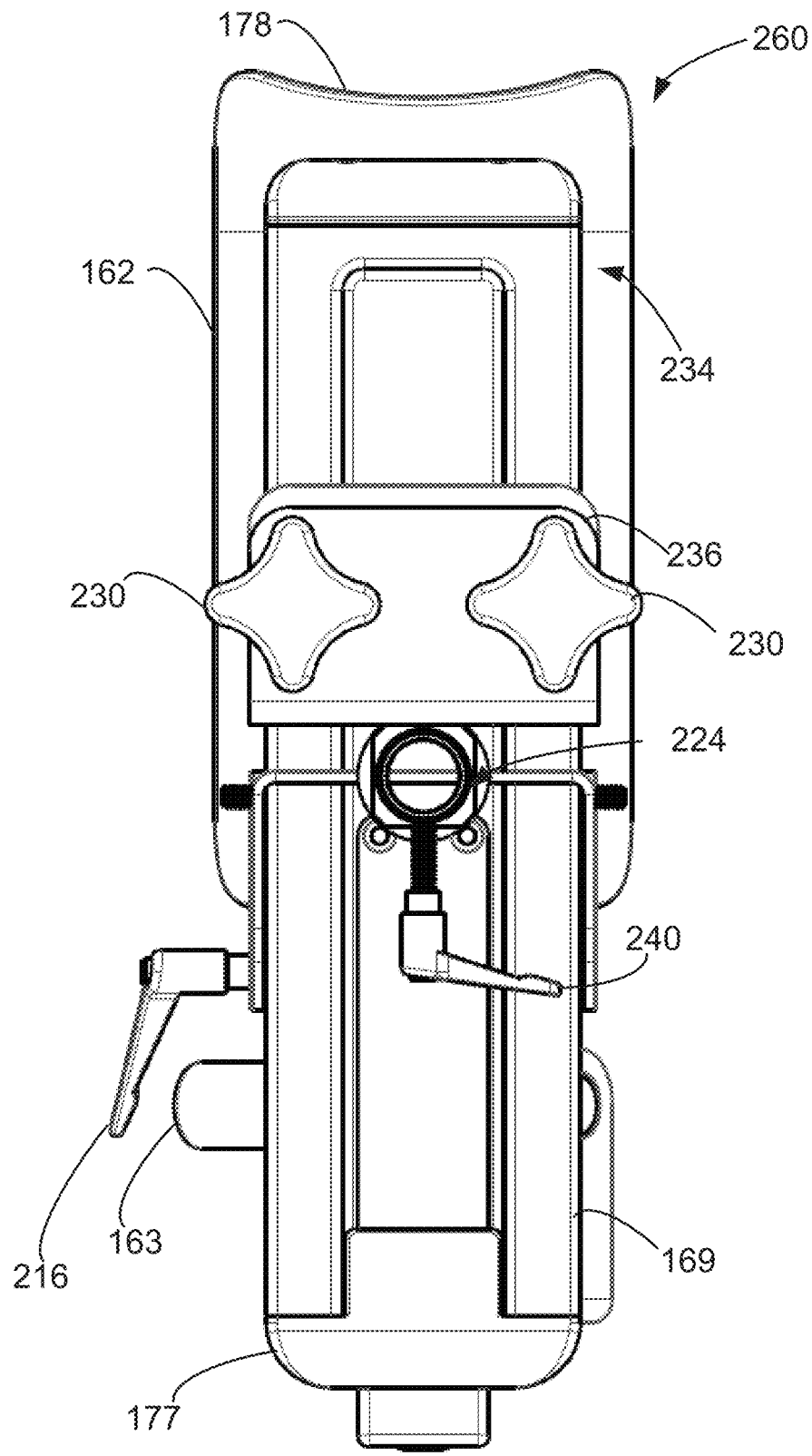
FIG. 46 is a bottom elevation view of the apparatus of FIG. 41

FIG. 46 is a bottom elevation view of the apparatus 260 of FIG. 41, showing components on the lower portion of apparatus 260, including the clamp handles 230 and the underside 234 of the cuff 162. This view further shows the (pole) clamp assembly 224 arranged in the center of the underside of the apparatus 260.

Figure 47:
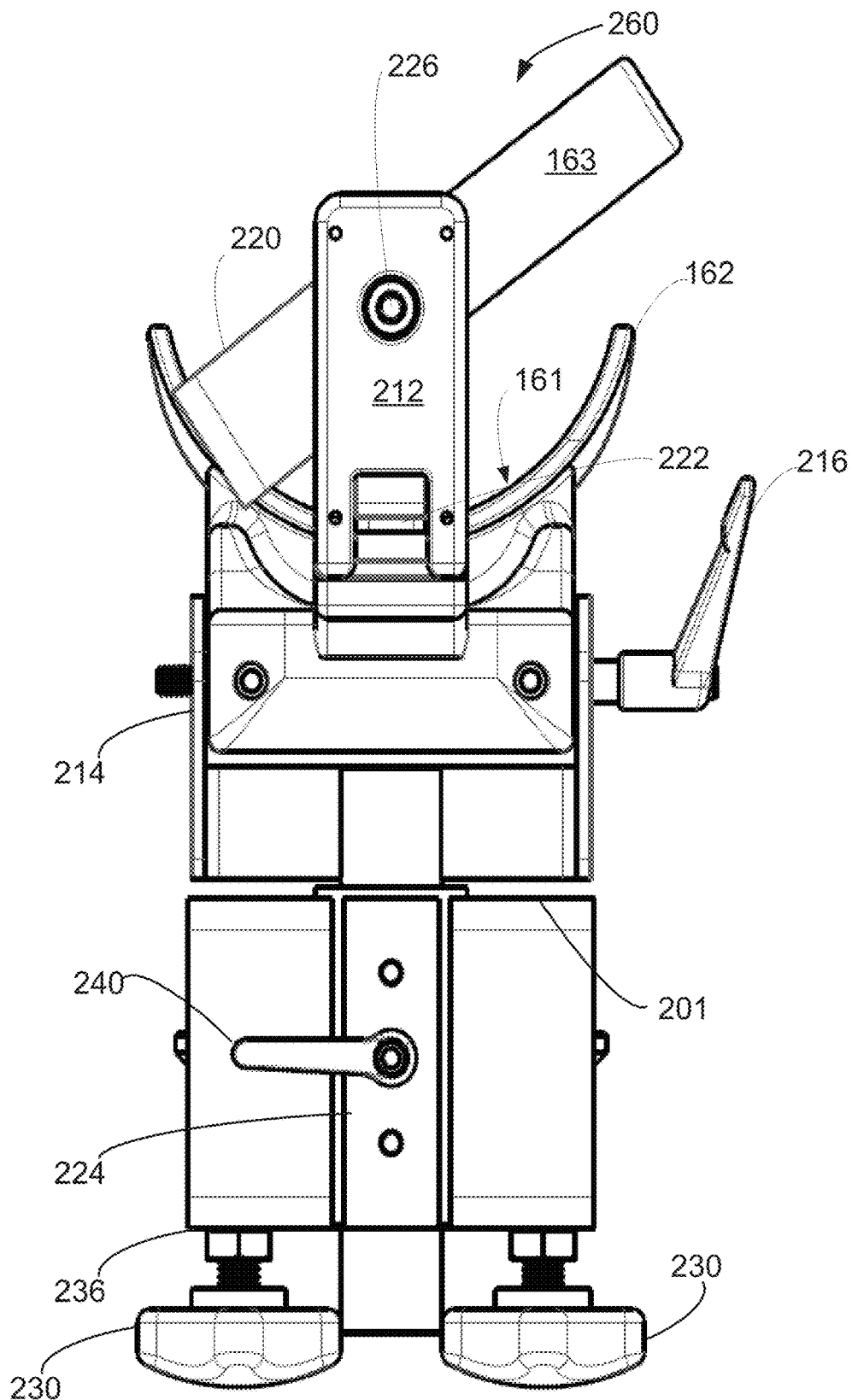
FIG. 47 is a front elevation view of the apparatus of FIG. 41.

FIG. 47 is a front elevation view of the apparatus 260 of FIG. 41, further illustrating views of the above-described components, including the rotational assembly 212, the handle 163, the bracket 220, the actuation lever 222 (which when actuated allows the rotation of the handle 163) and a rotational element 229, which defines the rotational axis 226 (FIG. 42).

Figure 48:
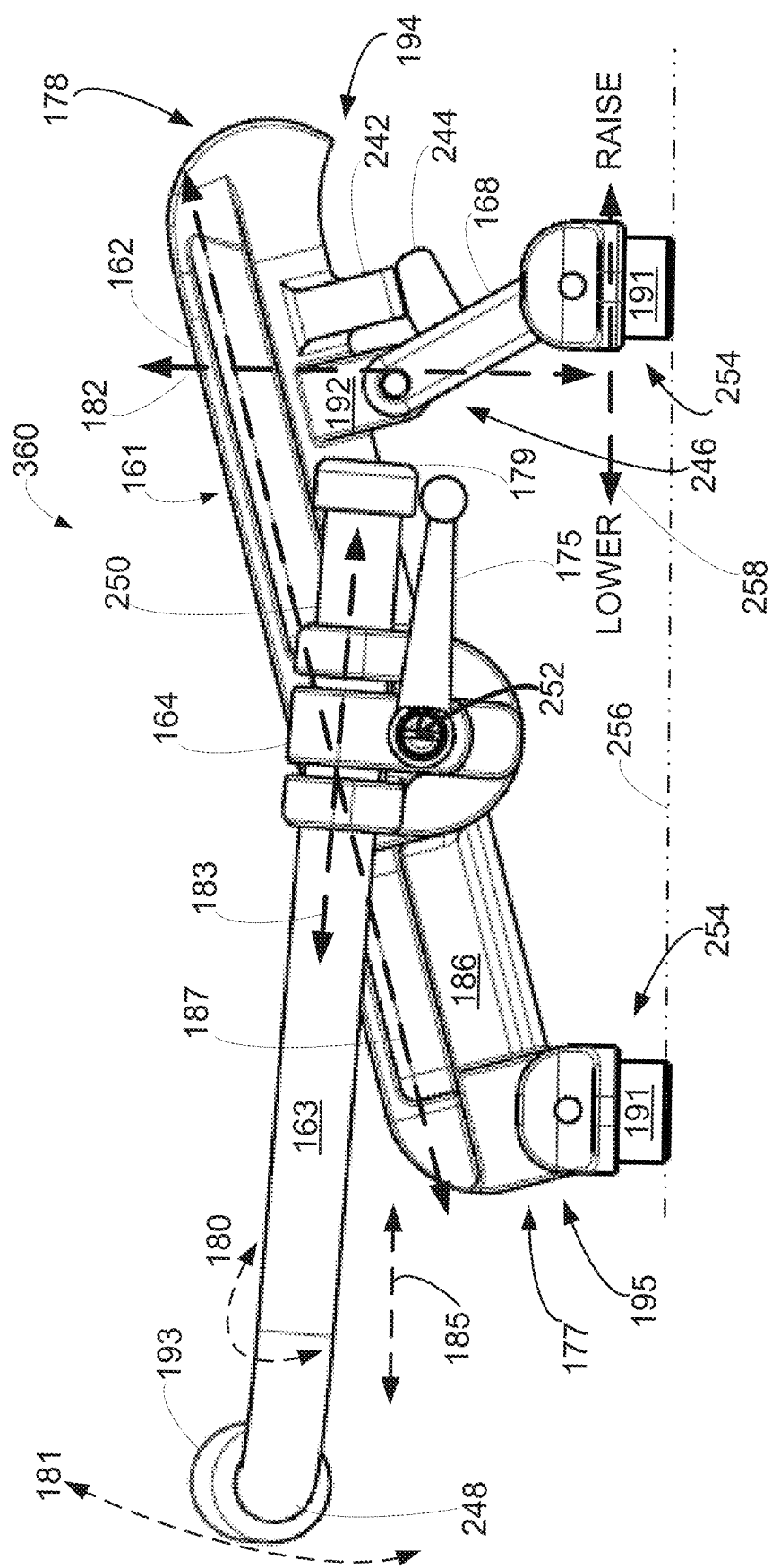
FIG. 48 is a side elevation view of another embodiment of an apparatus for stabilizing an extremity, which has certain similar components as the apparatus shown in FIG. 34. This example of an extremity stabilizing apparatus does not have a lateral base portion but includes an elevation assembly that elevates the back end of the cuff to position the cuff at different angles (e.g., inclined positions) relative to a surface supporting the apparatus.

FIG. 48 is a side elevation view of another example of an apparatus 360 for stabilizing an extremity, which is similar in some aspects to the example shown in FIG. 34 and having some of the same components as previously described in reference to FIG. 34. The apparatus 360 differs in its configuration at least by not having a base 169 like the embodiment illustrated in FIG. 34, advantageously providing a lighter weight, more mobile design. As illustrated in FIG. 48, the apparatus 360 includes a cuff 162 having a cuff surface 161 and cuff base 186. The cuff 162 has a front 177 and a back 178, and a longitudinal axis 187 that extends from the front 177 to the back 178 of the cuff 162. The cuff surface 161 is configured for receiving an extremity of a patient. The top surface 161 may be flat in some configurations. In some configurations, the top surface 161 may be similar to the curved cuff surface 161 illustrated in FIG. 35, having a lower center portion 161a extending from the back 178 to the front 177, and higher side portions 161b on opposite sides of the center portion 161a, also extending from the back 178 to the front 177 to form a c-shaped cuff surface 161 with the open portion of the "c" facing upward with respect to the apparatus 160.

Still referring to the embodiment of FIG. 48, the apparatus 360 also includes a lower portion of support structure 254. The support structure 254 may include, for example, a plurality of feet 191 that support the apparatus 360 when it is placed on a surface 256, the feet 191 aligned to engage the surface 256 and hold the apparatus 360 steady. In some embodiments, the feet 191 are adjustable to vary the height of the apparatus. For example, the feet 191 may be coupled to a bolt that winds into support structure 254 that the feet 191 are attached to.

The apparatus 360 illustrated in FIG. 48 also includes an elevation assembly 246 that operates to move the elevating end 195 of the cuff 162 away from the lower portion 254 (and a support surface 256) to position the top surface 161 at various angles relative to the support surface 256. For example, raise and lower the elevating end 194 of the cuff 162 along the direction arrow 182. In this example, elevation assembly 246 includes a hinge that comprises linkage 168 coupled to bracket 192. This example of an elevation assembly 246 has two positions, a raised position (illustrated) and a lowered position where the cuff 162 is lowered to be in a horizontal configuration (e.g., substantially parallel with surface 256. Other examples of elevations assemblies which may be implemented may have a plurality of positions, as described in the other examples in this disclosure. One advantage of this design is its minimal structure which makes it lightweight, easy to operate, and minimizes potential problems when being used in mobile situations. The elevation assembly 246 illustrated in FIG. 48 includes a lateral support member 244 coupled to the cuff linkage 168 and a vertical support member 242 coupled to the cuff base 186. When the lower portion 254 at the back 178 of the apparatus 360 is moved along the direction arrow 258 (towards "raise"), the elevation assembly 246 is extended, raising the cuff 162 away from the supporting surface 256. When the cuff 162 is raised, the hinge is in an open position (as shown in FIG. 48) with the lateral support member 244 contacting the vertical support member 242, which stops the elevation assembly 246 in the raised position. To lower the cuff 162, the elevation assembly 246 can be actuated such that the lower portion 254 at the back 178 of the apparatus 360 is moved along the direction arrow 258 (towards "lower") towards the front 177 of the apparatus 160, the lateral support member 244 disengages the bracket 242, and the hinge is in an un-extended position folding as the lower portion 254 moves forward. In this example, the elevation assembly 246 is configured to place the elevating portion 195 of the cuff 162 in two different positions (elevated and flat). In other examples, the elevation assembly 246 may be configured to include more than two positions.

The apparatus 360 illustrated in FIG. 48 also includes a clamp 164 attached to the cuff base 186. The clamp 164 moves correspondingly with the cuff 162 when the cuff 162 is elevated. The clamp 164 in FIG. 48 may be similar to the clamp 164 illustrated in FIG. 34. In other examples, various other clamps that provide the same or similar functionality may be used. The clamp 164 is tightened and released using a clamp handle 175 that is coupled to a threaded member at axis 252. The axis 252 is aligned normal to, or substantially normal to, the longitudinal orientation of the cuff 162 in FIG. 48 (that is, axis 252 extends in a direction into the page of FIG. 48). The handle 163 includes a distal portion 248 that extends in front of the apparatus 360 and a proximal portion 250 that runs through the clamp 164. In some embodiments, including as illustrated in FIG. 48, the handle 163 is "L" shaped, with the longer portion of the "L" being the proximal portion 250 and the shorter portion of the "L" being the distal portion 248, the shorter portion extending laterally in front 177 of the apparatus 160 When the clamp 164 is sufficiently loosened, the handle 163 is configured to move along the direction arrow 183, that is, along a longitudinal axis 183 of the proximal portion of the handle 163, to position the distal portion 248 at varying distances 185 from the front 177 of the cuff 162. This is one adjustment that allows the apparatus 360 to accommodate extremities of different dimensions. The handle 163 may include a grip 193 for receiving a patient's hand. The grip 193 may be similar to other grips described for other embodiments described herein (for example, the grip 193 in FIG. 34). In various implementations, the grip 193 may be part of the handle 163 or a separate component that fits over a portion of the handle 163, e.g., over a part of the distal portion 248. In some embodiments, the handle 163 and grip 193 are formed from the same material. In some embodiments, the handle 163 and grip 193 may be made from a suitable material (e.g., metal, plastic, or the like).

In addition of the movement of the handle 163 along motion arrow 183, the handle 163 may rotate in the clamp 164 around the longitudinal axis 183 of the proximal portion 250, e.g., rotate in the direction of motion arrow 180, when the clamp 164 is sufficiently loosened. The rotation of the handle 163 moves the grip 193 to different alignment positions relative to the cuff 162 to accommodate placement of a patient's arm/hand different positons as maybe needed for different procedures. The rotation 180 of the handle 163 represents a second way the grip may be positioned relative to the cuff 162. The handle 163 may also be elevated or lowered in the direction of the motion arrow 181 by sufficiently loosening the clamp 164. In other words, the handle 163 maybe rotated around the axis 252 when the clamp 164 loosened, and then secured in place at a desired location by tightening clamp 164.

In operation, a patient's forearm may be placed on the cuff 162 adjacent to the cuff top surface 161. The shape of the top surface 161 helps to hold the forearm securely in an extended position. The back 178 of the cuff 162 may be raised along the motion arrow 182, as desired. The handle 163 may be adjusted along one or more of the motion arrows 180, 181, 183, and then secured at that position, to place the grip 193 at a desired position for a patient to grasp during a procedure.

Figure 49:
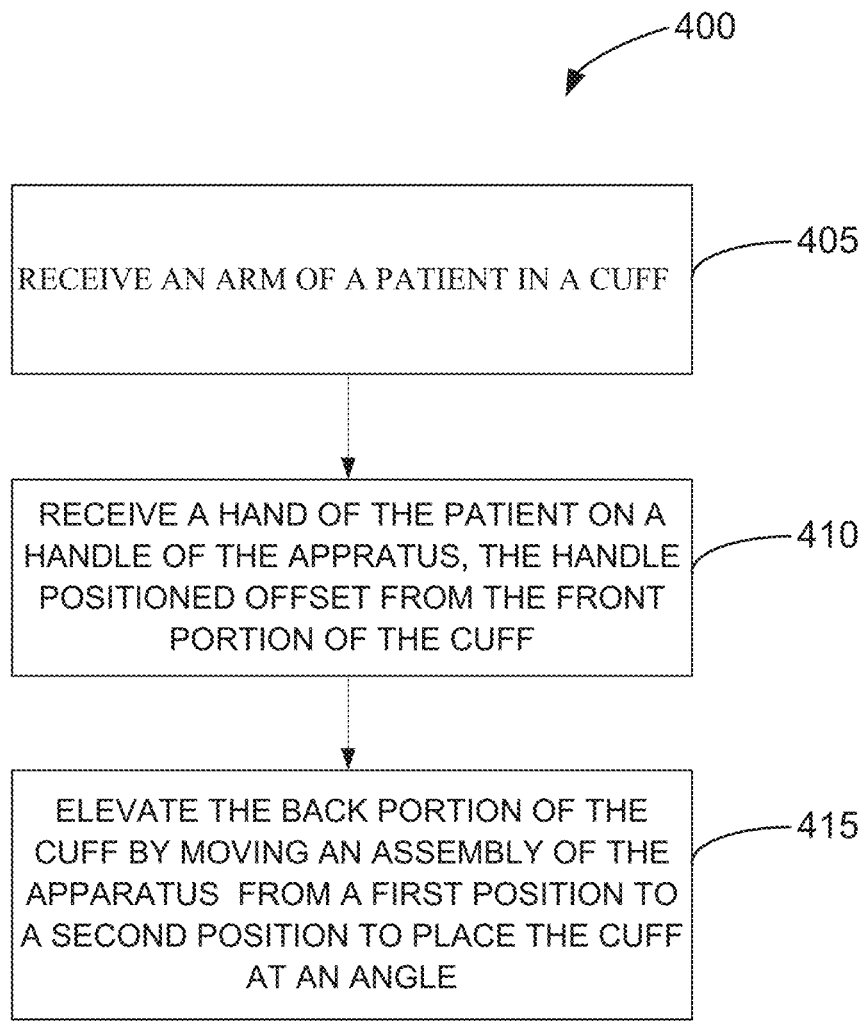
FIG. 49 is a flowchart illustrating a method of stabilizing an extremity.

FIG. 49 is a flowchart illustrating a method 400 of stabilizing an extremity. At block 405, the method 400 operates to receive an arm of a patient in a cuff. The cuff may include a curved top surface including a center portion, side portions of the cuff extending from the center portion, a front portion of the cuff and a back portion of the cuff. Some examples of cuffs are illustrated in the cuff 162 of FIGS. 34, 41, and 48. At block 410, the method operates to receive the hand of a patient on a handle of the apparatus. In some embodiments, the handle includes a grip portion that is configured to receive the hand of a patient. The handle is arranged to be offset from the front portion of the cuff at a certain distance. Some examples of handles 163 and grips 193 are illustrated in FIGS. 34, 41, and 48. At block 415 the method 400 operates to elevate the back portion of the cuff by moving an assembly of the apparatus from a first position to a second position to place the cuff at an angle. Moving the assembly from a first position to a second position correspondingly moves the back end of the cuff. Some examples of the components that may be used in methods of stabilizing an extremity are illustrated in FIGS. 34, 41, and 48. For example, in FIG. 34 the positioning mechanism 196, bracket 192 and cuff linkage 168 operate to move the back of the cuff 162 away from the base 169, elevating the back of cuff 162 to place the cuff 162 an one or several possible angles with respect to the base 169. In FIG. 41, the slot engaging member 231a can be moved to one of a plurality of positions in the slot 229 of the base clamp 214, which moves the back 178 of the cuff 162 relative to the clamp assembly 241 (e.g., along motion arrow 204) and places the cuff 162 at one of a plurality of angles with respect to the clamp assembly 241 (and for example, a horizontal plane running through the clamp assembly 241). In FIG. 48, the bracket 192 and the cuff linkage 168 form a hinge that when extended (e.g., when the lower portion 254 that is coupled to the cuff linkage 168 is moved towards the back of the cuff) the cuff 162 is moved relative to the lower portion 254 (e.g., a foot 191 at the back of the apparatus 360) from a first position (lowered) to a second position (raised), for example, in the direction of motion arrow 182, such that the cuff 162 is at an angle (e.g., relative to a surface 256 supporting the apparatus 360). In some embodiments, the method may include moving the handle 163 relative to the cuff 162 (e.g., rotating the handle 163, elevating the handle 163, and/or translating the handle 163) to change the position of the handle relative to the cuff 162. In some embodiments, the method may include rotating the apparatus, or a portion of the apparatus around a fixed point, for example, where the apparatus is configured to be attached to a fixture or other structure as in the embodiment illustrated FIGS. 41-47.

The foregoing description details certain embodiments of the systems, devices, and methods disclosed herein. It will be appreciated, however, that no matter how detailed the foregoing appears in text, the systems, devices, and methods can be practiced in many ways. As is also stated above, it should be noted that the use of particular terminology when describing certain features or aspects of the invention should not be taken to imply that the terminology is being re-defined herein to be restricted to including any specific characteristics of the features or aspects of the technology with which that terminology is associated.

The various features and processes described above may be used independently of one another, or may be combined in various ways. All possible combinations and sub-combinations are intended to fall within the scope of this disclosure. The example systems and components described herein may be configured differently than described. For example, elements may be added to, removed from, or rearranged compared to the disclosed example embodiments.

Throughout this specification, plural instances may implement components, operations, or structures described as a single instance. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Although an overview of the subject matter has been described with reference to specific example embodiments, various modifications and changes may be made to these embodiments without departing from the broader scope of embodiments of the present disclosure. Such embodiments of the subject matter may be referred to herein, individually or collectively, by the term "invention" merely for convenience and without intending to voluntarily limit the scope of this application to any single disclosure or concept if more than one is, in fact, disclosed.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

As used herein, the term "or" may be construed in either an inclusive or exclusive sense. Moreover, plural instances may be provided for resources, operations, or structures described herein as a single instance. Additionally, boundaries between various resources, operations, engines, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure. Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

Headings are included herein for reference and to aid in locating various sections. These headings are not intended to limit the scope of the concepts described with respect thereto. Such concepts may have applicability throughout the entire specification.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present. It will be appreciated by those skilled in the art that various modifications and changes may be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the figures may be combined, interchanged or excluded from other embodiments.

The phrase "based on" does not mean "based only on," unless expressly specified otherwise. In other words, the phrase "based on" describes both "based only on" and "based at least on." Unless otherwise explicitly stated, articles such as "a" or "an" should generally be interpreted to include one or more described items. Accordingly, phrases such as "a device configured to" are intended to include one or more recited devices.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims. Applicant reserves the right to submit claims directed to combinations and sub-combinations of the disclosed inventions that are believed to be novel and non-obvious. Inventions embodied in other combinations and sub-combinations of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims, are to be considered within the subject matter of the inventions described herein.

What is claimed is:

1. An extremity stabilization apparatus, comprising:
a cuff having a top surface structured for receiving a limb of a patient, the cuff having a front end, back end, and a longitudinal axis of the cuff that extends from the cuff front end to the cuff back end;
a cuff base having a top portion coupled to the cuff;
a clamp assembly coupled to the cuff base, the clamp assembly including:
a base clamp coupling the clamp assembly to the cuff base such that the cuff base is translatable along the longitudinal axis of the cuff relative to the clamp assembly, and
a pole clamp configured such that the cuff base is rotatable around a longitudinal axis of the pole clamp;
a handle positioned in front of the cuff and offset from the front end of the cuff, the handle having a grip portion configured to receive a hand, of the patient whose limb is supported by the cuff, around the grip portion of the handle such that fingers of the patient's hand can encircle and grasp the grip portion;
a rotating handle assembly coupled to the handle and coupled to the cuff base, the rotating handle assembly extending from the cuff base to a position in front of a front end of the handle and positions the handle in front of the cuff between the rotating handle assembly and the cuff, and to position an axis of rotation of the handle in front of the cuff and aligned with the longitudinal axis of the cuff, the rotating handle assembly configured to allow movement of the handle around the axis of rotation of the handle to align the handle in multiple positions, including a vertically aligned position and a horizontally aligned position.

2. The apparatus of claim 1, wherein
the cuff base further comprises a front portion and a back portion, the front portion coupled to the handle via the rotating handle assembly, and two sidewalls disposed on opposite sides of the cuff base, each of the two sidewalls including an elongated aperture aligned in a parallel with the longitudinal axis of the cuff; and
wherein the clamp assembly is coupled to the cuff base by at least one member extending through the elongated apertures such that the cuff base is translatable and rotatable to a position relative to the clamp assembly and secured in place via the base clamp.

3. The apparatus of claim 2, wherein the clamp assembly further comprises a fixture clamp configured to attach the apparatus to a horizontal surface.

4. The apparatus of claim 3, wherein the pole clamp comprises a vertical clamp including a handle and a receiver, the pole clamp configured to be secured at a desired vertical position on a member placed in the receiver by tightening the handle of the pole clamp.

5. The apparatus of claim 4, wherein the pole clamp is coupled to a side of the fixture clamp.

6. The apparatus of claim 1, wherein the rotating handle assembly is further configured to rotate the handle in a plane normal to the longitudinal axis of the cuff.

7. The apparatus of claim 6, wherein the rotating handle assembly comprises a locking mechanism to hold the handle in a fixed position.

8. The apparatus of claim 1, wherein the top surface of the cuff is curved such that sides of the cuff form a c-shaped surface with an opening facing away from the clamp assembly.

9. An extremity stabilization apparatus, comprising:
a cuff having a top surface structured for receiving a limb of a patient, the cuff having a front end, back end, and a longitudinal axis of the cuff that extends in a first direction from the cuff front end to the cuff back end;
a handle offset from the front end of the cuff extending across the front end of the cuff in a second direction that is normal to the first direction, the handle configured to receive a hand of the patient whose limb is supported by the cuff around the handle such that fingers of the patient's hand can encircle around the handle;
a rotating handle assembly coupled to the handle and coupled to the cuff and positioned in front of a front end of the handle such that the handle is between the rotating handle assembly and the cuff top surface, the rotating handle assembly configured to move the handle around an axis aligned with the longitudinal axis of the cuff, the movement of the handle around the axis aligning the handle in multiple positions, including a vertically aligned position and a horizontally aligned position; and
an assembly coupled to the cuff, the assembly movable to change a position of the top surface of the cuff from a first position to a second position, each of the first position and second positions corresponding to a different angle of the top surface of the cuff.

10. The apparatus of claim 9, wherein the first direction is perpendicular to the second direction.

11. The apparatus of claim 9, wherein the handle is cylindrically-shaped.

* * * * *